(12) United States Patent
Gupta et al.

(10) Patent No.: US 8,119,346 B2
(45) Date of Patent: Feb. 21, 2012

(54) LIGHT EMISSION MODIFIERS AND THEIR USES IN NUCLEIC ACID DETECTION, AMPLIFICATION AND ANALYSIS

(75) Inventors: Amar P. Gupta, Danville, CA (US); Stephen G. Will, Rotkreuz (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 260 days.

(21) Appl. No.: 12/551,810

(22) Filed: Sep. 1, 2009

(65) Prior Publication Data

US 2010/0015629 A1 Jan. 21, 2010

Related U.S. Application Data

(62) Division of application No. 11/474,062, filed on Jun. 23, 2006, now Pat. No. 7,919,242.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ........ 435/6.1; 435/91.2; 536/23.1; 536/24.3

(58) Field of Classification Search .................. None
See application file for complete search history.

(56) References Cited

U.S. PATENT DOCUMENTS

| 5,491,063 | A | 2/1996 | Fisher et al. |
| 6,251,581 | B1 | 6/2001 | Ullman et al. |
| 2003/0044830 | A1 | 3/2003 | Iwaki et al. |
| 2003/0136921 | A1 | 7/2003 | Reel |

FOREIGN PATENT DOCUMENTS

| EP | 0 699 768 B1 | 8/1995 |
| EP | 1 081 495 A1 | 9/1999 |
| EP | 06013330.3 | 11/2006 |
| EP | 09168656 | 10/2009 |
| WO | WO 99/28500 | 6/1999 |
| WO | WO 2004/033726 A1 | 4/2004 |
| WO | 2004057023 A1 | 7/2004 |

OTHER PUBLICATIONS

Lai, R. Y. et al., PNAS USA, vol. 103, pp. 4017-4021 (Mar. 2006).*
Boon, E.M. et al. (Nature Biotech., vol. 18, p. 1096-1100 (2000).*
Roller, S.D. et al., J. Chem. Tech. Biotechnol., vol. 34B, pp. 3-12 (1984).*
Erdem, A., et al, 2000, "Novel hybridization indicator methylene blue for the electrochemical detection of short DNA sequences related to the hepatitis B virus", *Analytica Chimica Acta*, 422: 139-149.
Kelley, S., et al, 1997, "Electrochemistry of Methylene Blue Bound to a DNA-Modified Electrode", *Bioconjugate Chem.*, 8: 31-37.
Kelley, S., et al, "Single-base mismatch detection based on charge transduction through DNA", *Nucleic Acids Research*, 27 (24): 4830-3837.
Nolan, R., et al, 2003, "A Simple Quenching Method for Fluorescence Background Reduction and Its Application to the Direct, Quantitative Detection of Specific mRNA", *Anal. Chem.*, 75: 6236-6243.
Sauer, M., et al, 1998, "Dynamics of the electron transfer reaction between an oxazine dye and DNA oligonucleotides monitored on the single-molecule level", *Chemical Physics Letters*, 284: 153-163.
Truite, E., et al, 1995, "The Interaction of Methylene Blue, Azure B, and Thionine with DNA: Formation of Complexes with Polynucleotides and Mononucleotides as Model Systems", 35: 419-433.
Yarrow, J., et al, 2004, "A high-throughput cell migration assay using scratch wound healing, a comparison of image-based readout methods", *BMC Biotechnology*, 4: 1-9.
Tanaka, Shigeyuki, et al., 1981, "Thermodynamic Studies of DNA-Dye Complex, 2 DNA-Methylene Blue and DNA-Thionine Systems", Makromol. Chem., 182(5):1475-1480.
Jain, N. C., et al., 1991, "Phagocytosis of Opsonised Fluorescent Platelets by Neutrophils to Detect Antiplatelet Antibody," Comparative Haematology International, 1:77-82.
Kutyavin, Igor V., et al., 2002, "Reduced aggregation and improved specificity of G-rich oligodeoxyribonucleotides containing pyrazolo[3,4-d]pyrimidine guanine bases", Nucleic Acids Research, 30 (22):4952-4959.
Calladine, C. R. et al., 1996, "A Useful Role for "Static" Models in Elucidating the Behavior of DNA in Solution", J. Mol. Biol., 257:479-485.
Maliwal, B. P. et al., 1995, "Flourescence Energy Transfer in One Dimension: Domain-Frequency Flouresence Study of DNA-Flourophore Complexes", Biopolymers, 35:245-255.
Stratagene Catalog, 1988, "Gene Characterization Kits", p. 39.

\* cited by examiner

*Primary Examiner* — Teresa E Strzelecka
(74) *Attorney, Agent, or Firm* — David J. Chang; Olga Kay

(57) ABSTRACT

The present invention relates to methods and reagents for modifying the emission of light from labeled nucleic acids for the purpose of real time detection, analysis, and quantitation of nucleic acid sequences, e.g., using singly labeled probes. These methods and reagents exploit advantageous properties of thiazine dyes and diazine dyes. Furthermore, the use of these light emission modifiers in background reduction, nucleic acid duplex stabilization and other uses is also described. Related kits, reaction mixtures and integrated systems are described.

14 Claims, 36 Drawing Sheets

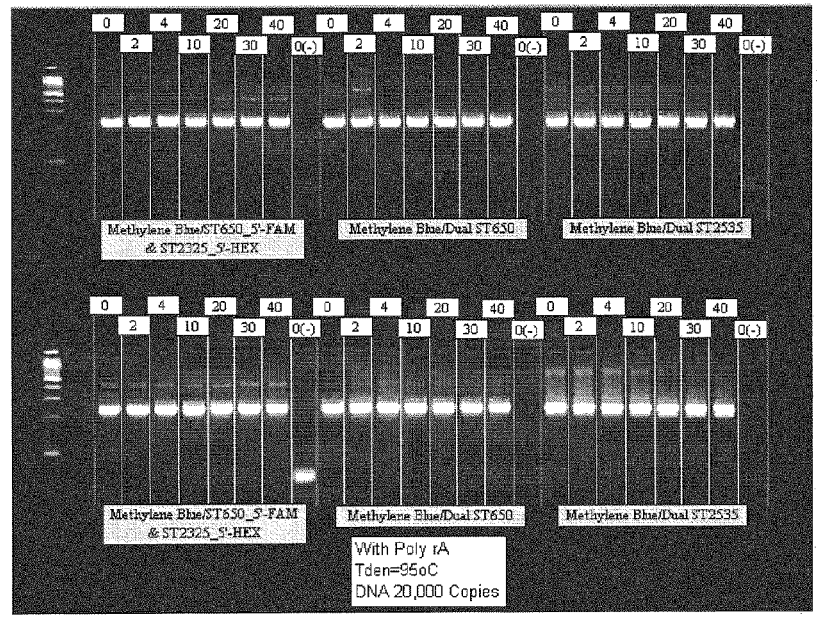
Fig. 22A
Fig. 22B
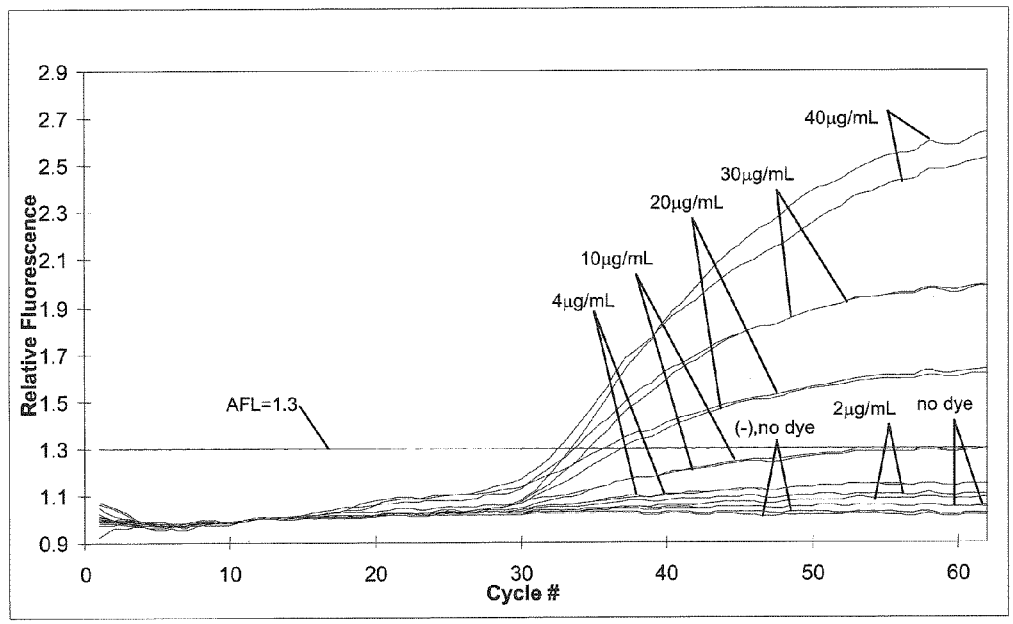
Fig. 23

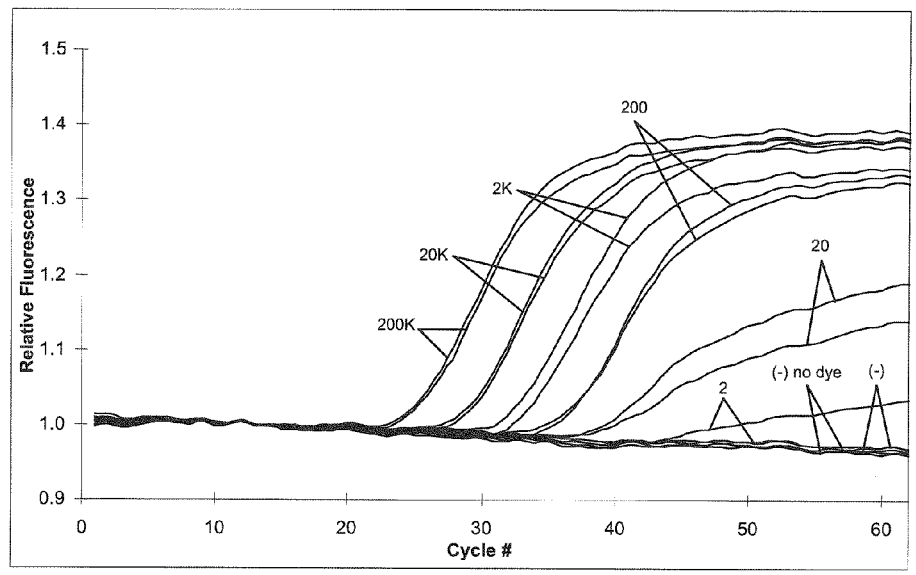
Fig. 30
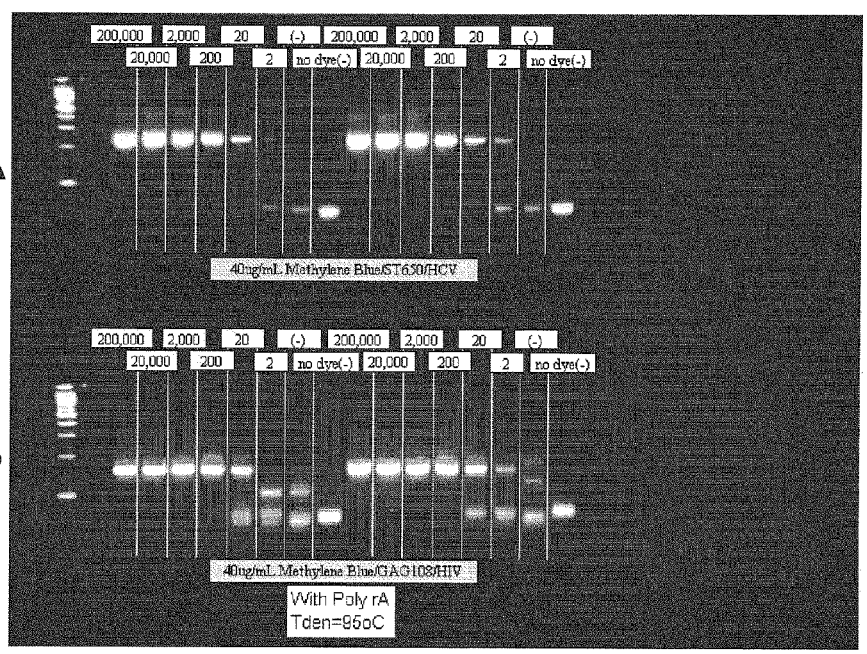
Fig. 31A
Fig. 31B

Probe: FAM-CGGAATTGCCAGGACGACCGG (SEQ ID NO: 14)

```
Forward Amplification Primer Region
        SK145         AGTGGGGGG ACATCAAGCAGCCATGCAAAT(SEQ ID No. 35)
HIV Subtype SDL101-15 ......... .....................(SEQ ID No. 36)
HIV Subtype SDL105-1  ......... .....................(SEQ ID No. 37)
HIV Subtype SDL106-1  ......... G...........T........(SEQ ID No. 38)
HIV Subtype SDL108-3  ......... ............T........(SEQ ID No. 39)
HIV Subtype SDL109-1  ......... G...........T........(SEQ ID No. 40)
HIV Subtype SDL110-5  ...A.AA.. ...C...G.....A........(SEQ ID No. 41)
HIV Subtype SDL113-1  ......... ...C...G.....T.....G..(SEQ ID No. 42)
HIV Subtype SDL114-2  .........G...C...G.....T........(SEQ ID No. 43)
HIV Subtype SDL115-2  ......... ...C...G.....T.....G..(SEQ ID No. 44)
HIV Subtype SDL156-1  ......... ...C...G.....A........(SEQ ID No. 45)
HIV Subtype G_G3-03   C........ G...........T........(SEQ ID No. 46)

Reverse Amplification Primer Region (reverse complement)
        GAG152        GGAAGTGACATAGCAGGAACTACTAGTACC(SEQ ID No. 47)
HIV Subtype SDL101-15 .............................(SEQ ID No. 48)
HIV Subtype SDL105-1  .............................(SEQ ID No. 49)
HIV Subtype SDL106-1  ........T....................(SEQ ID No. 50)
HIV Subtype SDL108-3  ........T....................(SEQ ID No. 51)
HIV Subtype SDL109-1  ........T................C...(SEQ ID No. 52)
HIV Subtype SDL110-5  .............................(SEQ ID No. 53)
HIV Subtype SDL113-1  .............................(SEQ ID No. 54)
HIV Subtype SDL114-2  ........T....................(SEQ ID No. 55)
HIV Subtype sDL115-2  ...G.....................C...(SEQ ID No. 56)
HIV Subtype SDL156-1  ............................G.(SEQ ID No. 57)
HIV Subtype G_G3-03   ........T....................(SEQ ID No. 58)

5' nuclease probe region (reverse complement)
        GAG108        TAAAAGATACCATCAATGAGGAAGCTGCAGA(SEQ ID No. 59)
HIV Subtype SDL101-15 ..............A......A...G........(SEQ ID No. 60)
HIV Subtype SDL105-1  .......G...........................(SEQ ID No. 61)
HIV Subtype SDL106-1  ....G.....T........................(SEQ ID No. 62)
HIV Subtype SDL108-3  ....G...G.T........................(SEQ ID No. 63)
HIV Subtype SDL109-1  ....G.....T........................(SEQ ID No. 64)
HIV Subtype SDL110-5  .......A...........................(SEQ ID No. 65)
HIV Subtype SDL113-1  ...................................(SEQ ID No. 66)
HIV Subtype SDL114-2  ...................................(SEQ ID No. 67)
HIV Subtype sDL115-2  ...................................(SEQ ID No. 68)
HIV Subtype SDL156-1  ....G..A..........A................(SEQ ID No. 69)
HIV Subtype G_G3-03   ........T.T..T.....A...............(SEQ ID No. 70)
```

Fig. 62

SEQUENCE LISTING

```
<160> NUMBER OF SEQ ID NOS: 70

<210> SEQ ID NO 1
<211> LENGTH: 26
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (26)..(26)
<223> OTHER INFORMATION: n is N6-t-butylbenzyl-dA

<400> SEQUENCE: 1
gcagaaagcg tctagccatg gcgttn                                          26

<210> SEQ ID NO 2
<211> LENGTH: 28
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (28)..(28)
<223> OTHER INFORMATION: n is N6-t-butylbenzyl-dA

<400> SEQUENCE: 2
gcaagcaccc tatcaggcag taccacan                                        28

<210> SEQ ID NO 3
<211> LENGTH: 31
```

```
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with FAM
<220> FEATURE:
<221> NAME/KEY: misc_feature
<222> LOCATION: (14)..(15)
<223> OTHER INFORMATION: BHQ-2 is inserted between nucleotide positions
      14 and 15
<220> FEATURE:
<221> NAME/KEY: misc_feature
<222> LOCATION: (31)..(31)
<223> OTHER INFORMATION: n is dG modified with terminal phosphate

<400> SEQUENCE: 3
nggtgtactc accgttccgc agaccactat n                                         31

<210> SEQ ID NO 4
<211> LENGTH: 32
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with CY5
<220> FEATURE:
<221> NAME/KEY: misc_feature
<222> LOCATION: (14)..(15)
<223> OTHER INFORMATION: cx-FAM is inserted between nucleotide positions
      14 and 15
<220> FEATURE:
<221> NAME/KEY: misc_feature
<222> LOCATION: (32)..(32)
<223> OTHER INFORMATION: n is dG modified with terminal phosphate

<400> SEQUENCE: 4
nggtgtactc accggttccg cagaccacta tn                                        32

<210> SEQ ID NO 5
<211> LENGTH: 31
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with FAM
<220> FEATURE:
<221> NAME/KEY: misc_feature
<222> LOCATION: (31)..(31)
<223> OTHER INFORMATION: n is dG modified with terminal phosphate

<400> SEQUENCE: 5
nggtgtactc accgttccgc agaccactat n                                         31

<210> SEQ ID NO 6
<211> LENGTH: 29
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (29)..(29)
<223> OTHER INFORMATION: n is N6-t-butylbenzyl-dA

<400> SEQUENCE: 6
```
agtgggggga catcaagcag ccatgcaan                                    29

<210> SEQ ID NO 7
<211> LENGTH: 30
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (30)..(30)
<223> OTHER INFORMATION: n is N6-t-butylbenzyl-dA

<400> SEQUENCE: 7
ggtactagta gttcctgcta tgtcacttcn                                   30

<210> SEQ ID NO 8
<211> LENGTH: 31
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (31)..(31)
<223> OTHER INFORMATION: n is dA modified with terminal phosphate

<400> SEQUENCE: 8
taaaagatac catcaatgag gaagctgcag n                                 31

<210> SEQ ID NO 9
<211> LENGTH: 31
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dT modified with FAM
<220> FEATURE:
<221> NAME/KEY: misc_feature
<222> LOCATION: (31)..(31)
<223> OTHER INFORMATION: n is dA modified with terminal phosphate

<400> SEQUENCE: 9
nctgcagctt cctcattgat ggtatctttt n                                 31

<210> SEQ ID NO 10
<211> LENGTH: 26
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (26)..(26)
<223> OTHER INFORMATION: n is N6-t-butylbenzyl-dA

<400> SEQUENCE: 10
gcagaaagcg tctagccatg gcgttn                                       26

<210> SEQ ID NO 11
<211> LENGTH: 28
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (28)..(28)
<223> OTHER INFORMATION: n is N6-t-butylbenzyl-dA

<400> SEQUENCE: 11
gcaagcaccc tatcaggcag taccacan                                              28

<210> SEQ ID NO 12
<211> LENGTH: 31
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dT modified with FAM
<220> FEATURE:
<221> NAME/KEY: misc_feature
<222> LOCATION: (31)..(31)
<223> OTHER INFORMATION: n is dT modifed with terminal phosphate

<400> SEQUENCE: 12
nggactcagt cctctggtca tctcaccttc n                                          31

<210> SEQ ID NO 13
<211> LENGTH: 31
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dT modified with FAM
<220> FEATURE:
<221> NAME/KEY: misc_feature
<222> LOCATION: (31)..(31)
<223> OTHER INFORMATION: n is dA modified with terminal phosphate

<400> SEQUENCE: 13
nctgcagctt cctcattgat ggtatctttt n                                          31

<210> SEQ ID NO 14
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with FAM

<400> SEQUENCE: 14
nggaattgcc aggacgaccg g                                                     21

<210> SEQ ID NO 15
<211> LENGTH: 31
<212> TYPE: DNA
<213> ORGANISM: Artificial
<220> FEATURE:
<223> OTHER INFORMATION: Synthetic oligonucleotide

<400> SEQUENCE: 15
aggacccggt cgtcctggca attccggtgt a                                          31

<210> SEQ ID NO 16
<211> LENGTH: 31
<212> TYPE: DNA
<213> ORGANISM: Artificial

```
<220> FEATURE:
<223> OTHER INFORMATION: Synthetic oligonucleotide

<400> SEQUENCE: 16
aggacccagt cttcccggca attccggtgt a                              31

<210> SEQ ID NO 17
<211> LENGTH: 31
<212> TYPE: DNA
<213> ORGANISM: Artificial
<220> FEATURE:
<223> OTHER INFORMATION: Synthetic oligonucleotide

<400> SEQUENCE: 17
aggacccggt catcccggcg attccggtgt a                              31

<210> SEQ ID NO 18
<211> LENGTH: 31
<212> TYPE: DNA
<213> ORGANISM: Artificial
<220> FEATURE:
<223> OTHER INFORMATION: Synthetic oligonucleotide

<400> SEQUENCE: 18
aggacccggt ctttccggta attccggtgt a                              31

<210> SEQ ID NO 19
<211> LENGTH: 31
<212> TYPE: DNA
<213> ORGANISM: Artificial
<220> FEATURE:
<223> OTHER INFORMATION: Synthetic oligonucleotide

<400> SEQUENCE: 19
aggacccggt catcccggca attccggtgt a                              31

<210> SEQ ID NO 20
<211> LENGTH: 31
<212> TYPE: DNA
<213> ORGANISM: Artificial
<220> FEATURE:
<223> OTHER INFORMATION: Synthetic oligonucleotide

<400> SEQUENCE: 20
aggacccggt catcctggca attccggtgt a                              31

<210> SEQ ID NO 21
<211> LENGTH: 31
<212> TYPE: DNA
<213> ORGANISM: Artificial
<220> FEATURE:
<223> OTHER INFORMATION: Synthetic oligonucleotide

<400> SEQUENCE: 21
aggacccggt cacccagcg attccggtgt a                               31

<210> SEQ ID NO 22
<211> LENGTH: 24
<212> TYPE: DNA
<213> ORGANISM: Artificial
<220> FEATURE:
<223> OTHER INFORMATION: Synthetic oligonucleotide

<400> SEQUENCE: 22
cggaattgcc aggacgacga ccgg                                      24
```

```
<210> SEQ ID NO 23
<211> LENGTH: 29
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (29)..(29)
<223> OTHER INFORMATION: n is N6-t-butylbenzyl-dA

<400> SEQUENCE: 23
agtgggggga catcaagcag ccatgcaan                                29

<210> SEQ ID NO 24
<211> LENGTH: 30
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (30)..(30)
<223> OTHER INFORMATION: n is N6-t-butylbenzyl-dA

<400> SEQUENCE: 24
ggtactagta gttcctgcta tgtcacttcn                               30

<210> SEQ ID NO 25
<211> LENGTH: 31
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dT modified with FAM
<220> FEATURE:
<221> NAME/KEY: misc_feature
<222> LOCATION: (9)..(10)
<223> OTHER INFORMATION: BHQ-2 is inserted between nucleotide positions
      9 and 10
<220> FEATURE:
<221> NAME/KEY: misc_feature
<222> LOCATION: (31)..(31)
<223> OTHER INFORMATION: n is dA modified with terminal phosphate

<400> SEQUENCE: 25
nctgcagctt cctcattgat ggtatctttt n                             31

<210> SEQ ID NO 26
<211> LENGTH: 21
<212> TYPE: DNA
<213> ORGANISM: Artificial
<220> FEATURE:
<223> OTHER INFORMATION: Synthetic oligonucleotide

<400> SEQUENCE: 26
ccggtcgtcc tggcaattcc g                                        21

<210> SEQ ID NO 27
<211> LENGTH: 21
<212> TYPE: DNA
<213> ORGANISM: Artificial
<220> FEATURE:
<223> OTHER INFORMATION: Synthetic oligonucleotide

<400> SEQUENCE: 27
ccggtcgtcc cggcaattcc g                                        21
```

<210> SEQ ID NO 28
<211> LENGTH: 21
<212> TYPE: DNA
<213> ORGANISM: Artificial
<220> FEATURE:
<223> OTHER INFORMATION: Synthetic oligonucleotide

<400> SEQUENCE: 28
ccggtcgtcc gggcaattcc g                                              21

<210> SEQ ID NO 29
<211> LENGTH: 21
<212> TYPE: DNA
<213> ORGANISM: Artificial
<220> FEATURE:
<223> OTHER INFORMATION: Synthetic oligonucleotide

<400> SEQUENCE: 29
ccggtcgtcc aggcaattcc g                                              21

<210> SEQ ID NO 30
<211> LENGTH: 21
<212> TYPE: DNA
<213> ORGANISM: Artificial
<220> FEATURE:
<223> OTHER INFORMATION: Synthetic oligonucleotide

<400> SEQUENCE: 30
ccggtcgtcc tggccattcc g                                              21

<210> SEQ ID NO 31
<211> LENGTH: 21
<212> TYPE: DNA
<213> ORGANISM: Artificial
<220> FEATURE:
<223> OTHER INFORMATION: Synthetic oligonucleotide

<400> SEQUENCE: 31
ccggtcgtcc tggcgattcc g                                              21

<210> SEQ ID NO 32
<211> LENGTH: 21
<212> TYPE: DNA
<213> ORGANISM: Artificial
<220> FEATURE:
<223> OTHER INFORMATION: Synthetic oligonucleotide

<400> SEQUENCE: 32
ccggtcgtcc tggctattcc g                                              21

<210> SEQ ID NO 33
<211> LENGTH: 21
<212> TYPE: DNA
<213> ORGANISM: Artificial
<220> FEATURE:
<223> OTHER INFORMATION: Synthetic oligonucleotide

<400> SEQUENCE: 33
ccggtcgtcc tcgcaattcc g                                              21

<210> SEQ ID NO 34
<211> LENGTH: 21
<212> TYPE: DNA
<213> ORGANISM: Artificial
<220> FEATURE:
<223> OTHER INFORMATION: Synthetic oligonucleotide

```
<400> SEQUENCE: 34
ccggtcgtcg tggcaattcc g                                              21

<210> SEQ ID NO 35
<211> LENGTH: 30
<212> TYPE: DNA
<213> ORGANISM: Artificial
<220> FEATURE:
<223> OTHER INFORMATION: HIV subtype consensus sequence

<400> SEQUENCE: 35
agtgggggga catcaagcag ccatgcaaat                                     30

<210> SEQ ID NO 36
<211> LENGTH: 30
<212> TYPE: DNA
<213> ORGANISM: Artificial
<220> FEATURE:
<223> OTHER INFORMATION: HIV subtype consensus sequence

<400> SEQUENCE: 36
agtgggggga catcaagcag ccatgcaaat                                     30

<210> SEQ ID NO 37
<211> LENGTH: 30
<212> TYPE: DNA
<213> ORGANISM: Artificial
<220> FEATURE:
<223> OTHER INFORMATION: HIV subtype consensus sequence

<400> SEQUENCE: 37
agtgggggga catcaagcag ccatgcaaat                                     30

<210> SEQ ID NO 38
<211> LENGTH: 30
<212> TYPE: DNA
<213> ORGANISM: Artificial
<220> FEATURE:
<223> OTHER INFORMATION: HIV subtype consensus sequence

<400> SEQUENCE: 38
agtggggggg catcaagcag ctatgcaaat                                     30

<210> SEQ ID NO 39
<211> LENGTH: 30
<212> TYPE: DNA
<213> ORGANISM: Artificial
<220> FEATURE:
<223> OTHER INFORMATION: HIV subtype consensus sequence

<400> SEQUENCE: 39
agtgggggga catcaagcag ctatgcaaat                                     30

<210> SEQ ID NO 40
<211> LENGTH: 30
<212> TYPE: DNA
<213> ORGANISM: Artificial
<220> FEATURE:
<223> OTHER INFORMATION: HIV subtype consensus sequence

<400> SEQUENCE: 40
agtggggggg catcaagcag ctatgcaaat                                     30

<210> SEQ ID NO 41
<211> LENGTH: 30
<212> TYPE: DNA
```

-continued

```
<213> ORGANISM: Artificial
<220> FEATURE:
<223> OTHER INFORMATION: HIV subtype consensus sequence

<400> SEQUENCE: 41
agtagaagga caccaggcag caatgcaaat                                    30

<210> SEQ ID NO 42
<211> LENGTH: 30
<212> TYPE: DNA
<213> ORGANISM: Artificial
<220> FEATURE:
<223> OTHER INFORMATION: HIV subtype consensus sequence

<400> SEQUENCE: 42
agtgggggga caccaggcag ctatgcagat                                    30

<210> SEQ ID NO 43
<211> LENGTH: 31
<212> TYPE: DNA
<213> ORGANISM: Artificial
<220> FEATURE:
<223> OTHER INFORMATION: HIV subtype consensus sequence

<400> SEQUENCE: 43
agtggggggg acaccaggca gctatgcaaa t                                  31

<210> SEQ ID NO 44
<211> LENGTH: 30
<212> TYPE: DNA
<213> ORGANISM: Artificial
<220> FEATURE:
<223> OTHER INFORMATION: HIV subtype consensus sequence

<400> SEQUENCE: 44
agtgggggga caccaggcag ctatgcagat                                    30

<210> SEQ ID NO 45
<211> LENGTH: 30
<212> TYPE: DNA
<213> ORGANISM: Artificial
<220> FEATURE:
<223> OTHER INFORMATION: HIV subtype consensus sequence

<400> SEQUENCE: 45
agtgggggga caccaggcag caatgcaaat                                    30

<210> SEQ ID NO 46
<211> LENGTH: 30
<212> TYPE: DNA
<213> ORGANISM: Artificial
<220> FEATURE:
<223> OTHER INFORMATION: HIV subtype consensus sequence

<400> SEQUENCE: 46 cgtgggggggg catcaagcag ctatgcaaat                                   30

<210> SEQ ID NO 47
<211> LENGTH: 30
<212> TYPE: DNA
<213> ORGANISM: Artificial
<220> FEATURE:
<223> OTHER INFORMATION: HIV subtype consensus sequence

<400> SEQUENCE: 47
ggaagtgaca tagcaggaac tactagtacc                                    30
```

```
<210> SEQ ID NO 48
<211> LENGTH: 30
<212> TYPE: DNA
<213> ORGANISM: Artificial
<220> FEATURE:
<223> OTHER INFORMATION: HIV subtype consensus sequence

<400> SEQUENCE: 48
ggaagtgaca tagcaggaac tactagtacc                                    30

<210> SEQ ID NO 49
<211> LENGTH: 30
<212> TYPE: DNA
<213> ORGANISM: Artificial
<220> FEATURE:
<223> OTHER INFORMATION: HIV subtype consensus sequence

<400> SEQUENCE: 49
ggaagtgaca tagcaggaac tactagtacc                                    30

<210> SEQ ID NO 50
<211> LENGTH: 30
<212> TYPE: DNA
<213> ORGANISM: Artificial
<220> FEATURE:
<223> OTHER INFORMATION: HIV subtype consensus sequence

<400> SEQUENCE: 50
ggaagtgata tagcaggaac tactagtacc                                    30

<210> SEQ ID NO 51
<211> LENGTH: 30
<212> TYPE: DNA
<213> ORGANISM: Artificial
<220> FEATURE:
<223> OTHER INFORMATION: HIV subtype consensus sequence

<400> SEQUENCE: 51
ggaagtgata tagcaggaac tactagtacc                                    30

<210> SEQ ID NO 52
<211> LENGTH: 30
<212> TYPE: DNA
<213> ORGANISM: Artificial
<220> FEATURE:
<223> OTHER INFORMATION: HIV subtype consensus sequence

<400> SEQUENCE: 52
ggaagtgata tagcaggaac taccagtacc                                    30

<210> SEQ ID NO 53
<211> LENGTH: 30
<212> TYPE: DNA
<213> ORGANISM: Artificial
<220> FEATURE:
<223> OTHER INFORMATION: HIV subtype consensus sequence

<400> SEQUENCE: 53
ggaagtgaca tagcaggaac tactagtacc                                    30

<210> SEQ ID NO 54
<211> LENGTH: 30
<212> TYPE: DNA
<213> ORGANISM: Artificial
<220> FEATURE:
<223> OTHER INFORMATION: HIV subtype consensus sequence
```

```
<400> SEQUENCE: 54
ggaagtgaca tagcaggaac tactagtacc                                    30

<210> SEQ ID NO 55
<211> LENGTH: 30
<212> TYPE: DNA
<213> ORGANISM: Artificial
<220> FEATURE:
<223> OTHER INFORMATION: HIV subtype consensus sequence

<400> SEQUENCE: 55
ggaagtgata tagcaggaac tactagtacc                                    30

<210> SEQ ID NO 56
<211> LENGTH: 30
<212> TYPE: DNA
<213> ORGANISM: Artificial
<220> FEATURE:
<223> OTHER INFORMATION: HIV subtype consensus sequence

<400> SEQUENCE: 56
ggaggtgaca tagcaggaac cactagtacc                                    30

<210> SEQ ID NO 57
<211> LENGTH: 30
<212> TYPE: DNA
<213> ORGANISM: Artificial
<220> FEATURE:
<223> OTHER INFORMATION: HIV subtype consensus sequence

<400> SEQUENCE: 57
ggaagtgaca tagcaggaac tactagtagc                                    30

<210> SEQ ID NO 58
<211> LENGTH: 30
<212> TYPE: DNA
<213> ORGANISM: Artificial
<220> FEATURE:
<223> OTHER INFORMATION: HIV subtype consensus sequence

<400> SEQUENCE: 58
ggaagtgata tagcaggaac tactagtacc                                    30

<210> SEQ ID NO 59
<211> LENGTH: 31
<212> TYPE: DNA
<213> ORGANISM: Artificial
<220> FEATURE:
<223> OTHER INFORMATION: HIV subtype consensus sequence

<400> SEQUENCE: 59
taaaagatac catcaatgag gaagctgcag a                                  31

<210> SEQ ID NO 60
<211> LENGTH: 31
<212> TYPE: DNA
<213> ORGANISM: Artificial
<220> FEATURE:
<223> OTHER INFORMATION: HIV subtype consensus sequence

<400> SEQUENCE: 60
taaaagatac cataaatgaa gaggctgcag a                                  31

<210> SEQ ID NO 61
<211> LENGTH: 31
<212> TYPE: DNA
```

```
<213> ORGANISM: Artificial
<220> FEATURE:
<223> OTHER INFORMATION: HIV subtype consensus sequence

<400> SEQUENCE: 61
taaaagagac catcaatgag gaagctgcag a                                    31

<210> SEQ ID NO 62
<211> LENGTH: 31
<212> TYPE: DNA
<213> ORGANISM: Artificial
<220> FEATURE:
<223> OTHER INFORMATION: HIV subtype consensus sequence

<400> SEQUENCE: 62
taaaggatac tatcaatgag gaagctgcag a                                    31

<210> SEQ ID NO 63
<211> LENGTH: 31
<212> TYPE: DNA
<213> ORGANISM: Artificial
<220> FEATURE:
<223> OTHER INFORMATION: HIV subtype consensus sequence

<400> SEQUENCE: 63
taaaggatgc tatcaatgag gaagctgcag a                                    31

<210> SEQ ID NO 64
<211> LENGTH: 31
<212> TYPE: DNA
<213> ORGANISM: Artificial
<220> FEATURE:
<223> OTHER INFORMATION: HIV subtype consensus sequence

<400> SEQUENCE: 64
taaaggatac tatcaatgag gaagctgcag a                                    31

<210> SEQ ID NO 65
<211> LENGTH: 31
<212> TYPE: DNA
<213> ORGANISM: Artificial
<220> FEATURE:
<223> OTHER INFORMATION: HIV subtype consensus sequence

<400> SEQUENCE: 65
taaaagaaac catcaatgag gaagctgcag a                                    31

<210> SEQ ID NO 66
<211> LENGTH: 31
<212> TYPE: DNA
<213> ORGANISM: Artificial
<220> FEATURE:
<223> OTHER INFORMATION: HIV subtype consensus sequence

<400> SEQUENCE: 66
taaaagatac catcaatgag gaagctgcag a                                    31

<210> SEQ ID NO 67
<211> LENGTH: 31
<212> TYPE: DNA
<213> ORGANISM: Artificial
<220> FEATURE:
<223> OTHER INFORMATION: HIV subtype consensus sequence

<400> SEQUENCE: 67
taaaagatac catcaatgag gaagctgcag a                                    31
```

```
<210> SEQ ID NO 68
<211> LENGTH: 31
<212> TYPE: DNA
<213> ORGANISM: Artificial
<220> FEATURE:
<223> OTHER INFORMATION: HIV subtype consensus sequence

<400> SEQUENCE: 68
taaaagatac catcaatgag gaagctgcag a                              31

<210> SEQ ID NO 69
<211> LENGTH: 31
<212> TYPE: DNA
<213> ORGANISM: Artificial
<220> FEATURE:
<223> OTHER INFORMATION: HIV subtype consensus sequence

<400> SEQUENCE: 69
taaaggaaac catcaatgaa gaagctgcag a                              31

<210> SEQ ID NO 70
<211> LENGTH: 31
<212> TYPE: DNA
<213> ORGANISM: Artificial
<220> FEATURE:
<223> OTHER INFORMATION: HIV subtype consensus sequence

<400> SEQUENCE: 70
taaaagattc tattaatgaa gaagctgcag a                              31
```

LIGHT EMISSION MODIFIERS AND THEIR USES IN NUCLEIC ACID DETECTION, AMPLIFICATION AND ANALYSIS

CROSS-REFERENCE TO RELATED APPLICATIONS

This application is a division of a pending application Ser. No. 11/474,062, filed on Jun. 23, 2006, which claims priority to and benefit of the following United States Provisional Patent Applications: Application Ser. No. 60/695,991, filed Jun. 30, 2005; Application Ser. No. 60/696,253, filed Jun. 30, 2005; Application Ser. No. 60/696,293, filed Jun. 30, 2005; and Application Ser. No. 60/696,303, filed Jun. 30, 2005.

FIELD OF THE INVENTION

The present invention relates to the fields of molecular biology and nucleic acid chemistry. In certain embodiments, methods and reagents for modifying the emission of light from labeled nucleic acids are provided for the purpose of real time homogeneous detection, analysis, and quantitation of nucleic acid sequences using singly labeled probes. Furthermore, the use of these light emission modifiers in background reduction and other uses is also described.

BACKGROUND OF THE INVENTION

The development of nucleic acid amplification technology (NAT) has revolutionized genetic analysis and engineering science. For example, the polymerase chain reaction (PCR) is commonly utilized to amplify specific target nucleic acids using selected primer nucleic acids, e.g., to facilitate the detection of the target nucleic acid as part of a diagnostic, forensic, or other application. Primers typically function in pairs that are designed for extension towards each other to cover the selected target region. A typical PCR cycle includes a high temperature (e.g., 85° C. or more) denaturation step during which the strands of double-stranded nucleic acids separate from one another, a low temperature (e.g., 45-65° C.) annealing step during which the primers hybridize to the separated single strands, and an intermediate temperature (e.g., around 72° C.) extension step during which a nucleic acid polymerase extends the primers. Two-temperature thermocycling procedures are also utilized. These generally include a high temperature denaturation step and a low temperature anneal-extend step. To produce a detectable amount of the particular PCR product or amplicon, these cycles are generally repeated between about 25-45 times.

PCRs are also described in many different U.S. patents including, e.g., U.S. Pat. No. 4,683,195, entitled "PROCESS FOR AMPLIFYING, DETECTING, AND/OR-CLONING NUCLEIC ACID SEQUENCES," which issued to Mullis et al. Jul. 28, 1987, U.S. Pat. No. 4,683,202, entitled "PROCESS FOR AMPLIFYING NUCLEIC ACID SEQUENCES," which issued to Mullis Jul. 28, 1987, and U.S. Pat. No. 4,965,188, entitled "PROCESS FOR AMPLIFYING, DETECTING, AND/OR CLONING NUCLEIC ACID SEQUENCES USING A THERMOSTABLE ENZYME," which issued to Mullis et al. Oct. 23, 1990, which are each incorporated by reference. Further, PCR-related techniques are also described in various other publications, such as Innis et al. (Eds.) *PCR Protocols: A Guide to Methods and Applications*, Elsevier Science & Technology Books (1990), Innis et al. (Eds.) *PCR Applications: Protocols for Functional Genomics*, Academic Press (1999), Edwards et al., *Real-Time PCR*, Taylor & Francis, Inc. (2004), and Rapley et al., *Molecular Analysis and Genome Discovery*, John Wiley & Sons, Inc. (2004), which are each incorporated by reference.

Many variations of the PCR as well as other nucleic acid amplification techniques have also been developed. Examples of these include reverse-transcription PCR (RT-PCR) (Joyce (2002) "Quantitative RT-PCR. A review of current methodologies" *Methods Mol. Biol.* 193:83-92 and Emrich et al. (2002) "Quantitative detection of telomerase components by real-time, online RT-PCR analysis with the LightCycler," *Methods Mol. Biol.* 191:99-108), the ligase chain reaction (LCR) (Lee (1996) "Ligase chain reaction," *Biologicals* 24(3):197-9), the polymerase ligase chain reaction (Barany et al. (1991) "The ligase chain reaction in a PCR world," *PCR Methods Appl.* 1(1):5-16), the Gap-LCR (Abravaya et al. (1995) "Detection of point mutations with a modified ligase chain reaction (Gap-LCR)," *Nucleic Acids Res.* 23(4):675-82), strand displacement amplification (Walker (1993) "Empirical aspects of strand displacement amplification," *PCR Methods Appl.* 3(1):1-6), linked linear amplification (LLA) (Killeen et al. (2003) "Linked linear amplification for simultaneous analysis of the two most common hemochromatosis mutations," *Clin Chem.* 49(7):1050-7), rolling circle amplification (RCA) (Nilsson et al. (2002) "Real-time monitoring of rolling-circle amplification using a modified molecular beacon design," *Nucleic Acids Res.* 30(14):e66), transcription-mediated amplification (TMA) (Emery et al. (2000) "Evaluation of performance of the Gen-Probe human immunodeficiency virus type 1 viral load assay using primary subtype A, C, and D isolates from Kenya," *J Clin Microbiol* 38:2688-2695), nucleic-acid-sequence-based amplification (NASBA) (Mani et al. (1999) "Plasma RNA viral load as measured by the branched DNA and nucleic acid sequence-based amplification assays of HIV-1," *J Acquir Immune Defic Syndr* 22:208-209 and Berndt et al. (2000) "Comparison between a nucleic acid sequence-based amplification and branched DNA test for quantifying HIV RNA load in blood plasma," *J Virol Methods* 89:177-181), and self-sustaining sequence replication (3SR) (Mueller et al. (1997) "Self-sustained sequence replication (3SR): an alternative to PCR," *Histochem Cell Biol* 108:431-7), which are each incorporated by reference.

Various strategies for detecting amplification products have been developed, including those involving 5' nuclease probes, molecular beacons, or SCORPION® primers, among many others. To illustrate, a 5' nuclease assay typically utilizes the 5' to 3' nuclease activity of certain DNA polymerases to cleave 5' nuclease probes during the course of a polymerase chain reaction (PCR). These assays allow for both the amplification of a target and the release of labels for detection, generally without resort to multiple handling steps of amplified products. Certain 5' nuclease probes include labeling moieties, such as a fluorescent reporter dye and a quencher dye. When the probe is intact, the proximity of the reporter dye to the quencher dye generally results in the suppression of the reporter fluorescence. In many cases, however, an intact probe produces a certain amount of residual or baseline fluorescence. During a 5' nuclease reaction, cleavage of the probe separates the reporter dye and the quencher dye from one another, resulting in a detectable increase in fluorescence from the reporter. The accumulation of PCR products or amplicons is typically detected indirectly by monitoring this increase in fluorescence in real-time.

Although many pre-existing nucleic acid amplification detection formats are simple and robust, certain challenges remain. For example, many of these detection formats utilize dual labeled probes (e.g., a probe that includes donor and acceptor moieties). The manufacture of these dual labeled probes generally involves synthesis, purification, and quality control processes that are complex, labor intensive, and expensive. In addition, the baseline fluorescence of dual labeled probes typically must fall within a specified range for optimum performance. Further, certain dual labeled probes may suffer from instability that results in baseline drift, which negatively impacts shelf-life. Moreover, the insertion of an internal label typically leads to duplex destabilization upon hybridization, which must generally be compensated for.

All of these problems can be circumvented if unquenched single-labeled probes are used for detecting the products of nucleic acid amplification reactions. For example, the use of ethidium bromide and several other DNA binding dyes to quench the fluorescence of oligonucleotides in a length dependent manner has been described. However, these dyes generally cannot be used for real time detection, e.g., due to their low DNA binding affinity at higher temperatures. Accordingly, there exists a need for nucleic acid amplification reaction mixture additives that have the ability to bind and quench single-labeled probes at higher temperatures typically utilized for real time detection.

In addition, multiplex nucleic acid amplification detection using 5' nuclease probes, molecular beacons, or FRET probes, among other detection methods, typically includes the pooling of quenched or unquenched fluorescent probes, e.g., to improve assay throughput relative to protocols that utilize single probes in a given reaction. To illustrate, multiplex assays are commonly used to detect multiple genotype markers or pathogens in samples obtained from patients as part of diagnostic procedures. In these formats, the overall baseline or background fluorescence from the pooled probes increases additively as the number of probes increases in the reaction mixture. This baseline fluorescence also increases in essentially any assay system when the amount of a single probe is increased. Baseline fluorescence generally adversely affects the performance of a given assay by, for example, reducing the detection sensitivity and dynamic range of the assay. Accordingly, baseline fluorescence effectively limits the total number of fluorescent probes and/or the amount of a given probe that can be added to a particular assay.

Although a wide variety of DNA hybridization and amplification strategies are known in the art, certain challenges remain. For example, the high levels of sequence divergence (i.e., sequence heterogeneity) in RNA/DNA viruses such as HIV, HCV and HPV make it particularly difficult to standardize methods for nucleic acid amplification, genotyping and/or detection. This viral sequence heterogeneity prevents the development of assays that have uniformly high sensitivity for all different viral genotypes and subtypes. Sequence differences between the experimental target and the primers and/or probes (e.g., probes for viral detection and/or genotyping) that result in duplex mismatches compromise assay performance, and can result in false negative results or misclassification. Failure to detect the multitude of relevant viral genotypes can have significant negative consequences, particularly in applications such as screening of clinical samples.

Quantitative assays (e.g., assays for assessing viral load) are even more vulnerable to sequence heterogeneity of the analytes, as the lower amplification/detection efficiencies might be falsely attributed to lower amounts of target present in a sample (in the absence of definitive genotype information). Because nucleic acid-based assays depend on hybridization, primer/probe mismatches can significantly reduce the accuracy of the quantitation.

In order to minimize these differences, primers and probes are preferably selected from conserved regions of viral genomes. However, this is becoming increasingly difficult in view of two primary factors, (i) many viruses, e.g., HIV and influenza, display rapid rates of mutagenesis and genome evolution, and (ii) the number of known viral genotypes and subtypes continues to grow, where the newly discovered isolates continue to expand the scope of known genomic diversity. In some cases, assigning viral genotype information is critical for patient stratification and therapy decisions, as differences are observed in the response to therapy based on the viral genotype. In these cases, it is more desirable to amplify and detect relatively less conserved regions of the viral genome in order to adequately differentiate between the various genotypes.

Primer/probe mismatches can be overcome to a limited extent by including a multiplicity of genotype specific primers and probes, or alternatively, by incorporating base analogs that increase the stability of DNA-DNA or RNA-RNA duplexes. However, these solutions are of limited utility and result in vastly increased assay complexity and cost. Although sequencing provides the highest resolution in genotype assignment, its application in a high-throughput clinical setting remains unfeasible.

As illustrated above, there is a need in the art for improved methods for nucleic acid analysis. For example, there is a need in the art for improved methods for nucleic acid detection, identification, amplification, characterization (e.g., Tm determination) and quantitation, especially where sequence heterogeneity and duplex mismatches can interfere with currently used methods. In the discussion above, the challenges of nucleic acid analysis are illustrated in the context of amplification, detection and genotyping of viral targets. However, these challenges are not unique to viral targets, and indeed, find relevance to a wide variety of nucleic acid analysis applications, such as microbial pathogen testing, genetic testing, and environmental testing.

SUMMARY OF THE INVENTION

The present invention provides methods of modulating the emission of light (e.g., baseline light emissions) from labeled nucleic acids, including 5'-nuclease probes. For example, certain light emission modifiers described herein reduce light emissions from labeled probes in solution at elevated temperatures and under other reaction conditions typically used for real-time detection. Moreover, unlike various other previously known solution quenchers, the light emission modifiers of the invention are not detrimental to the performance of nucleic acid amplification reactions and retain sufficient nucleic acid binding affinity at the elevated temperatures commonly utilized in these reactions such that real-time detection can be effected. The approaches to real-time detection described herein include the use of single-labeled probes, multi-labeled probes, or both types of probes together in a given reaction mixture. In addition to reaction mixtures and methods of modifying light emissions from labeled probes, related kits and systems are also provided.

In one aspect, the invention provides a reaction mixture that includes at least one labeled oligonucleotide. The oligonucleotide (e.g., a single-stranded oligonucleotide, etc.) is labeled with at least one light-emitting moiety (e.g., a fluorescent dye or the like). The reaction mixture also includes at least one soluble light emission modifier that modifies (e.g., reduces, etc.) a light emission from the labeled oligonucleotide. In some embodiments, the labeled oligonucleotide comprises a 5'-nuclease probe.

In another aspect, the invention provides a reaction mixture that includes at least one oligonucleotide that comprises at least two labeling moieties in which at least one of the labeling moieties is light-emitting. In some embodiments, for example, the oligonucleotide comprises a 5'-nuclease probe. The reaction mixture also includes at least one light emission modifier (e.g., a soluble light emission modifier, etc.) that modifies a baseline emission of light from the oligonucleotide at a temperature of at least about 40° C. In certain embodiments, the light emission modifier reduces the baseline emission of light from the oligonucleotide.

In another aspect, the invention relates to a reaction mixture that includes at least one oligonucleotide (e.g., a 5'-nuclease probe, etc.) that comprises at least two labeling moieties in which at least one of the labeling moieties is light-emitting. This reaction mixture also includes at least one diazine dye and/or thiazine dye that reduces a baseline emission of light from the oligonucleotide. Typically, the diazine dye and/or thiazine dye reduces the baseline emission of light from the oligonucleotide at a temperature of at least about 40° C.

In some embodiments, the reaction mixtures described herein comprise a plurality of oligonucleotides that are used, e.g., as part of a multiplexed 5'-nuclease reaction or other application. In these embodiments, at least one of the oligonucleotides generally comprises at least one labeling moiety that differs from a labeling moiety of another oligonucleotide. Typically, the different labeling moieties comprise different light-emitting labeling moieties (e.g., different fluorescent dyes, etc.) and the light emission modifier (e.g., a diazine dye, a thiazine dye, and/or the like) modifies (e.g., reduces) baseline emissions of light from each of the oligonucleotides. In some embodiments, the reaction mixtures of the invention are packaged in kits.

The reaction mixtures described herein optionally include various other components. In some embodiments, for example, reaction mixtures include components that are useful in performing nucleic acid amplification/detection assays, such as one or more of: a buffer, a salt, a metal ion, a nucleotide incorporating biocatalyst having a 5' to 3' nuclease activity (e.g., a Taq DNA polymerase, etc.), a pyrophosphatase, a primer nucleic acid, a template nucleic acid, an amplicon, a nucleotide, glycerol, dimethyl sulfoxide, poly rA (or another carrier nucleic acid), or the like. The reaction mixtures and other related aspects of the invention typically substantially lack ethidium bromide.

In one aspect, the invention provides a method of detecting a target nucleic acid in a sample. The method includes (a) providing at least one labeled oligonucleotide (e.g., a 5'-nuclease probe, etc.). The oligonucleotide is labeled with at least one light emitting moiety. In addition, at least a subsequence of the labeled oligonucleotide is sufficiently complementary to at least a subsequence of at least one target nucleic acid and/or to at least a subsequence of an amplicon of the target nucleic acid such that the labeled oligonucleotide hybridizes with the target nucleic acid and/or the amplicon of the target nucleic acid under at least one selected condition (e.g., an annealing temperature, an extension temperature, and/or the like). The method also includes (b) providing at least one soluble light emission modifier that modifies a light emission from the labeled oligonucleotide to a greater extent than from a labeled fragment of the oligonucleotide. In addition, the method includes (c) amplifying the nucleic acid in the sample in the presence of the labeled oligonucleotide and the soluble light emission modifier in an amplification reaction that comprises the selected condition such that the labeled oligonucleotide, hybridized with the target nucleic acid or the amplicon of the target nucleic acid, is cleaved to produce at least one labeled oligonucleotide fragment. The method further includes (d) detecting light emission at least from the labeled oligonucleotide fragment during (c), e.g., as a part of a real-time monitoring process.

In another aspect, the invention provides a method of modifying a baseline emission of light from a labeled oligonucleotide. The method includes (a) providing at least one oligonucleotide that comprises at least two labeling moieties in which at least one of the labeling moieties is light-emitting. The method also includes (b) contacting the oligonucleotide with at least one light emission modifier (e.g., a diazine dye, a thiazine dye, and the like) that modifies a baseline emission of light from the oligonucleotide at a temperature of at least about 40° C. (e.g., under conditions of real-time detection, etc.). In certain embodiments, (b) comprises contacting the oligonucleotide and the light emission modifier in solution. Typically, the method also includes detecting light emission from the labeled oligonucleotide before, during, and/or after (b).

In still another aspect, the invention provides a method of reducing a baseline emission of light from a labeled oligonucleotide. The method includes (a) providing at least one oligonucleotide that comprises at least two labeling moieties in which at least one of the labeling moieties is light-emitting. The method further includes (b) contacting the oligonucleotide with at least one diazine dye and/or thiazine dye, thereby reducing the baseline emission of light from the labeled oligonucleotide. In some embodiments, the oligonucleotide and the diazine dye and/or thiazine dye are contacted at a temperature of at least about 40° C. Typically, (b) includes contacting the oligonucleotide and the diazine dye and/or thiazine dye in solution. Moreover, the method generally includes detecting light emission from the labeled oligonucleotide before, during, and/or after (b).

In certain embodiments of the methods described herein, the methods comprise amplifying at least one target nucleic acid. Typically, at least a subsequence of the oligonucleotide is sufficiently complementary to at least a subsequence of the target nucleic acid and/or to at least a subsequence of an amplicon of the target nucleic acid such that the oligonucleotide hybridizes with the target nucleic acid and/or the amplicon of the target nucleic acid. In some of the embodiments, for example, the oligonucleotide comprises a 5'-nuclease probe and the method comprises amplifying the target nucleic acid under conditions whereby the 5'-nuclease probe is cleaved. In these embodiments, the method generally includes detecting cleavage of the 5'-nuclease probe. The target nucleic acid typically correlates with a diagnosis of at least one genetic disorder and/or at least one disease state for a subject that comprises a copy of the target nucleic acid.

In some multiplexing embodiments of the methods described herein, the methods include contacting a plurality of oligonucleotides with the light emission modifier (e.g., a diazine dye, a thiazine dye, and/or the like). In these embodiments, at least one of the oligonucleotides typically comprises at least one labeling moiety that differs from a labeling moiety of another oligonucleotide. The different labeling moieties generally comprise different light-emitting labeling moieties and the light emission modifier modifies (e.g., reduces) baseline emissions of light from each of the oligonucleotides.

To further illustrate, some embodiments of the methods described herein comprise contacting one or more single-labeled oligonucleotides (e.g., a 5'-nuclease probe, etc.) with the light emission modifier (e.g., a diazine dye, a thiazine dye, and/or the like). Typically, a labeling moiety of at least one of the single-labeled oligonucleotides is light-emitting and the light emission modifier modifies (e.g., reduces) an emission of light from the light-emitting single-labeled oligonucleotide.

In another aspect, the invention provides a kit that includes (a) at least one light emission modifier (e.g., one or more dyes selected from a diazine dye, a thiazine dye, and the like) that modifies baseline emissions of light from labeled oligonucleotides at a temperature of at least about 40° C. The kit also includes (b) instructions for modifying a light emission (e.g., a baseline emission of light, etc.) from at least one oligonucleotide that comprises at least one light-emitting labeling moiety with the light emission modifier. Generally, the kit includes at least one container for packaging the light emission modifier and/or the instructions.

In still another aspect, the invention provides a kit that includes (a) at least one diazine dye and/or thiazine dye. The kit also includes (b) instructions for reducing a light emission from at least one oligonucleotide that comprises at least one light-emitting labeling moiety with the diazine dye and/or thiazine dye. The kit also typically includes at least one container for packaging the diazine dye and/or thiazine dye and/or the instructions.

In some embodiments, the kits described herein also include various other components. To illustrate, these kits optionally include at least one primer nucleic acid that is at least partially complementary to at least one subsequence of a target nucleic acid. In certain embodiments, the kits include the oligonucleotide. Optionally, the oligonucleotide comprises a 5'-nuclease probe. In some embodiments, the kits include at least one single-labeled oligonucleotide that comprises a light-emitting labeling moiety. For example, the single-labeled oligonucleotide optionally comprises a primer nucleic acid that is at least partially complementary to at least one subsequence of at least one target nucleic acid. In embodiments of these kits that include primer nucleic acids, the kits also typically include instructions for amplifying one or more segments of the target nucleic acid with the primer nucleic acid, at least one nucleotide incorporating biocatalyst having a 5' to 3' nuclease activity, and one or more nucleotides. In these embodiments, the kits also generally include at least one nucleotide incorporating biocatalyst having a 5' to 3' nuclease activity and/or one or more nucleotides.

In another aspect, the invention relates to a system that includes (a) at least one oligonucleotide (e.g., a 5'-nuclease probe, etc.) that comprises at least one light-emitting labeling moiety. The system also includes (b) at least one light emission modifier (e.g., at least one diazine dye, thiazine dye, and/or the like) that modifies a baseline emission of light from the oligonucleotide at a temperature of at least about 40° C. In addition, the system also includes (c) at least one detector that detects light emitted from the oligonucleotide and/or at least one fragment of the oligonucleotide.

In yet another aspect, the invention provides a system that includes (a) at least one oligonucleotide (e.g., a 5'-nuclease probe, etc.) that comprises at least one light-emitting labeling moiety. In addition, the system also includes (b) at least one diazine dye and/or thiazine dye, and (c) at least one detector that detects light emitted from the oligonucleotide and/or at least one fragment of the oligonucleotide.

In certain embodiments, the systems described herein include certain other components. For example, the systems optionally include at least one logic device operably connected to the detector. The logic device generally includes one or more instruction sets that scale detected light emissions relative to one another. In some embodiments of these systems, at least one container comprises the oligonucleotide and the light emission modifier (e.g., at least one diazine dye, thiazine dye, and/or the like). In these embodiments, the systems typically include (d) at least one thermal modulator that thermally communicates with the container to modulate temperature in the container, and/or (e) at least one fluid transfer component that transfers fluid to and/or from the container. Generally, the oligonucleotide and the light-emitting labeling moiety are present in solution. In some embodiments, the container also includes components that can be used to perform various nucleic acid amplification-based assays, such as one or more of, e.g., a buffer, a salt, a metal ion, a nucleotide incorporating biocatalyst having a 5' to 3' nuclease activity, a pyrophosphatase, a primer nucleic acid, a template nucleic acid, an amplicon, a nucleotide, glycerol, dimethyl sulfoxide, poly rA, or the like.

The light emission modifiers utilized in the reaction mixtures, methods, kits, and systems described herein generally include soluble quencher moieties. In some embodiments, light emission modifiers substantially lack intrinsic fluorescence at least under selected light emission detection conditions (e.g., at detection wavelengths of 600 nm or less, etc.). Typically, the light emission modifiers described herein associate (e.g., intercalate, bind to, or the like) with oligonucleotides, such as the 5'-nuclease probes described herein. In certain embodiments, for example, a light emission modifier comprises one or more dyes selected from, e.g., a diazine dye, a thiazine dye, and the like. Exemplary diazine dyes include an azocarmine dye, a phenazine dye, diethylsafraninazodimethylaniline chloride (i.e., Janus Green B), and the like. Examples of suitable thiazine dyes include methylene blue, methylene green, thionin, 1,9-dimethylmethylene blue, sym-dimethylthionin, toluidine blue O, new methylene blue, methylene violet bernthsen, azure A, azure B, azure C, and the like.

The invention provides a variety of compositions and methods that find use in the detection, amplification and analysis of nucleic acids. More specifically, these methods utilize advantageous and previously unidentified properties of thiazine and diazine dyes.

In some embodiments, the methods of the invention take advantage of the previously unidentified ability of thiazine dyes to stabilize nucleic acid duplexes. This method is broadly applicable to any nucleic acid manipulation that uses duplex nucleic acid molecules and/or hybridization methodologies. Essentially, the methods for producing a stabilized nucleic acid duplex use the steps of (a) providing a sample containing or suspected of containing a target nucleic acid molecule; an oligonucleotide complementary or partially complementary to the target nucleic acid molecule; and at least one thiazine dye present at a concentration effective to stabilize a duplex formed between the target nucleic acid molecule and the oligonucleotide; and (b) alternatively (i) annealing the target nucleic acid and the oligonucleotide in the presence of the thiazine dye; or (ii) annealing the target nucleic acid and the oligonucleotide, followed by admixing with the thiazine dye; under conditions where a duplex can form to produce at least one stabilized nucleic acid duplex. In these methods, stability of the nucleic acid duplex of (b) is improved compared to the stability of the same nucleic acid duplex comprising the target nucleic acid and the oligonucleotide in the absence of the thiazine dye or a reduced concentration of the thiazine dye. These methods optionally include the demonstration of stability of the nucleic acid duplexes in the presence and absence or reduced concentration of the thiazine dye, which can be accomplished by any suitable method, for example, including (i) a melting temperature ($T_m$ analysis); (ii) a $C_T$ determination; or (iii) a 5'-nuclease assay.

In some aspects, the methods optionally include detecting the stabilized nucleic acid duplex under the conditions that provide improved stability.

It is not intended that the type, nature, configuration, structure or sequence of the duplex that is stabilized be limited in any respect. For example, in these methods, the stabilized nucleic acid duplex can comprise one or more, two or more, or three or more nucleobase mismatches. Perfect match duplexes can also be stabilized. In some aspects, the oligonucleotide in the stabilized duplex is effective to prime a nucleic acid extension reaction when annealed to the target nucleic acid. In some embodiments, the hybridization reactions are part of a PCR amplification reactions, where a pair of oligonucleotides are used in the hybridization with the target nucleic acid molecule, where each of the oligonucleotide primers is effective to prime a nucleic acid extension reaction when annealed to the target nucleic acid. In some aspects, the hybridization reaction includes a labeled oligonucleotide probe that is complementary or partially complementary to the target nucleic acid molecule. In some aspects, the target nucleic acid molecule is an amplicon.

The nucleic acids used in the methods of the invention are not limited to naturally occurring oligomeric structures or naturally occurring bases. For example, one or more of the molecules in the duplex can comprises one or more naturally-occurring nucleotides, modified nucleotides, nucleotide analogs, one or more unnatural bases, unnatural internucleotide linkages, unnatural nucleotide backbones, or any combination thereof.

Typically, in the methods for stabilizing nucleic acid duplexes, the stabilized hybridization complex is an intermolecular hybridization complex, where the antiparallel hybridizing strands are two separate nucleic acid molecules. However, in some adaptations of the methods for stabilizing nucleic acid duplexes, the stabilized hybridization complex is an intramolecular hybridization complex, where the antiparallel hybridizing strands are actually on a single nucleic acid molecule, such as in the case of a molecular beacon type configuration.

A requirement for these methods for duplex stabilization is the presence of a thiazine dye. Any thiazine dye can be used, for example but not limited to, methylene blue, methylene green, thionin, sym-dimethylthionin, toluidine blue O, new methylene blue, methylene violet bernthsen, azure A, azure B, azure C and 1,9-dimethylmethylene blue. The concentration of the dye that is used to improve the stability of the duplex is not particularly limited. In some aspects, at least one thiazine dye is present at a concentration of at least 10 µg/mL. In some aspects, the annealing comprises annealing in the presence of a thiazine dye at a concentration between about 10 µg/mL and 50 µg/mL, or alternatively, at a concentration between about 20 µg/mL and 40 µg/mL. In some embodiments, the thiazine dye is sued at a concentration of about 40 µg/mL.

In some embodiments, the invention provides kits for the execution of the methods for stabilizing nucleic acid duplexes. These kits can contain any reagents or other components that are required for or simplify any of the methods for duplex stabilization. In some aspects, these kits can contain an oligonucleotide complementary or partially complementary to a target nucleic acid molecule of interest; and at least one thiazine dye present at a concentration effective to stabilize a duplex formed between the target nucleic acid molecule and the oligonucleotide. The kits of the invention can include instructions to the kit user, and can also include one or more containers for holding all or any subset of components of the kit.

In some aspects, the invention provides integrated systems for the execution of the methods for stabilizing nucleic acid duplexes. The systems can include instrumentation and means for interpreting and analyzing collected data, especially where the collected data is subject to subsequent analysis using algorithms and/or electronically stored information (e.g., analysis of collected fluorescence data, etc). Each part of an integrated system is functionally interconnected, and in some cases, physically connected. In some embodiments, the integrated system is automated, where there is no requirement for any manipulation of the sample or instrumentation by an operator following initiation of the methods. A system of the invention can include instrumentation. For example, the invention can include a detector such as a fluorescence detector (e.g., a fluorescence spectrophotometer), and a thermal cycling device, or thermocycler. In some embodiments, the thermal cycling device and the detector are an integrated instrument, where the thermal cycling and emission detection (e.g., fluorescence detection) are done in the same device. A detector, e.g., a fluorescence spectrophotometer, can be connected to a computer for controlling the spectrophotometer operational parameters and/or for storage of data collected from the detector. The computer may also be operably connected to the thermal cycling device to control the temperature, timing, and/or rate of temperature change in the system. The integrated computer can also contain the "correlation module" where the data collected from the detector is analyzed. In some embodiments, the correlation module comprises a computer program that calculates.

A variety of uses of the thiazine dyes and diazine dyes as soluble light emission modifiers are provided herein. In one aspect, the methods of the invention take advantage of the previously unidentified light emission modifying properties of thiazine and diazine dyes by employing the dyes as soluble quenchers in a donor/quencher pair. In traditional FRET configurations, the FRET quencher moiety is typically integrated into the same nucleic acid molecule as the FRET donor, or alternatively, is integrated into a separate nucleic acid molecule. The invention provides methods that are a simplification over the methods used in the art, where the invention provides methods where the quencher moiety is replaced by a soluble quencher molecule that can be a thiazine dye or a diazine dye, or any molecule that is structurally related thereto that retains the required light-quenching property. The range of uses of the thiazine dyes and diazine dyes as soluble quenchers is not limited, and indeed, can be adapted for use in most instances where a traditional quenching moiety is used.

For example, in some aspects, the invention provides methods for determining the melting temperature ($T_m$) of a hybridization complex, the method comprising the steps:
(a) providing, (i) a probe comprising a light emitting moiety; (ii) a hybridization target that is complementary or partially complementary to the probe; and (iii) a soluble light emission modifier comprising a thiazine dye or a diazine dye, where the soluble light emission modifier is capable of quenching the light emitting moiety;
(b) annealing the probe with the hybridization target under conditions where base-pairing can occur to form a target hybridization complex;
(c) altering the temperature of the target hybridization complex in the presence of the soluble light emission modifier and measuring an emission of the light emitting moiety;
(d) correlating the measured emission of the light emitting moiety with the presence of the target hybridization complex as a function of temperature, thereby determining Tm of the target hybridization complex based on the measured emission.

In these Tm determination methods, the light emitting moiety can be a donor moiety, and the light emission modifier can be a quencher. In these methods, altering the temperature can be raising the temperature (melting curve) or lowering the temperature (annealing curve). In some aspects, a range of temperatures is used in the measuring step, for example, a range of temperatures of about 20° C. to about 95° C.

In some aspects, the hybridization target is an amplicon corresponding to a nucleic acid target, where the amplicon is typically generated by a polymerase chain reaction (e.g., in an asymmetric PCR amplification). In most instances where PCR is used, the PCR amplification uses an amplification primer pair specific for a target nucleic acid of interest, a thermostable DNA-dependent DNA polymerase, free deoxyribonucleotide triphosphates and a suitable DNA polymerase reaction buffer. In some embodiments, the amplicon generation is by reverse transcribing an RNA nucleic acid target and amplifying by a polymerase chain reaction (RT-PCR).

The targets for the Tm analysis are not limited in any aspect. In some embodiments, the nucleic acid target is a viral genome. The nucleic acid target can optionally be provided in a sample, which can be, for example, human blood, serum or plasma.

The methods for Tm determination contain at least one soluble quencher which can be a diazine dye or a thiazin dye; for example but not limited to, methylene blue, methylene green, thionin, sym-dimethylthionin, toluidine blue O, new methylene blue, methylene violet bernthsen, azure A, azure B, azure C, 1,9-dimethylmethylene blue, azocarmine dye, a phenazine dye, and diethylsafraninazodimethylaniline chloride.

The nucleic acids used in the methods of the invention for Tm determination are not limited to naturally occurring oligomeric structures or naturally occurring bases. For example, one or more of the molecules in the duplex can comprises one or more naturally-occurring nucleotides, modified nucleotides, nucleotide analogs, one or more unnatural bases, unnatural internucleotide linkages, unnatural nucleotide backbones, or any combination thereof.

In some embodiments, the invention provides kits for the execution of the methods for Tm determination. These kits can contain any reagents that are required for or simplify use of the methods for Tm determination. In some aspects, these methods can contain (a) at least one probe comprising a light emitting moiety, where the probe is complementary or partially complementary to a hybridization target of interest; (b) at least one soluble light emission modifier comprising a thiazine dye or a diazine dye, where the soluble light emission modifier is capable of quenching the light emitting moiety; and (c) one or more containers comprising the probe, the soluble light emission modifier, or both the probe and light emission modifier. In some aspects, the light emitting moiety is a FRET donor moiety. In some aspects, the light emission modifier is a FRET quencher. In some embodiments, the kits also contain instructions for determining the $T_m$ of a hybridization complex comprising the probe and the hybridization target.

Optionally, the kits of the invention for determining Tm can include one or more additional components selected from a reverse transcriptase, at least one primer suitable for reverse transcriptase initiation from an RNA target, a thermostable DNA-dependent DNA polymerase and/or a enzyme having both DNA-dependent and RNA-dependent (i.e., reverse transcriptase) polymerase activities, free deoxyribonucleotide triphosphates, standardization samples, positive control samples, negative control samples, buffers suitable for enzymatic reactions, sample collection tubes and amplification reaction tubes.

In some aspects, the invention provides integrated systems for the execution of the methods for Tm determination. The systems can include instrumentation and means for interpreting and analyzing collected data, especially where the collected data is subject to subsequent analysis using algorithms and/or electronically stored information (e.g., collected fluorescence data is translated into a Tm value). Each part of an integrated system is functionally interconnected, and in some cases, physically connected. The systems of the invention for conducting Tm determination of a hybridization complex include:

(a) a sample or reaction mixture comprising (i) a nucleic acid probe comprising a light emitting moiety that emits a signal; (ii) a target nucleic acid that is complementary or partially complementary to the nucleic acid probe; and (iii) a thiazine dye or a diazine dye;

(b) a thermal control device for regulating the temperature of the sample or reaction mixture over a range of temperatures, where the range includes: (i) a temperature where essentially all probe molecules anneal with the hybridization target at a given set of hybridization conditions; (ii) a temperature where 50% of the target hybridization complexes are dissociated at the hybridization conditions, and (iii) a temperature where essentially no probe molecules anneal with the hybridization target and essentially no hybridization complexes are present at the hybridization conditions;

(c) a detector for measuring the signal from the sample over the range of temperatures; and (d) a correlation module that is operably coupled to the detector and receives signal measurements over the range of temperatures, where the correlation module correlates the signal intensity with the presence of a hybridization complex comprising the probe and the hybridization target in admixture with the thiazine dye or diazine dye as a function of temperature, thereby determining the $T_m$ of the target hybridization complex.

In some aspects, the light emitting moiety is a FRET donor moiety.

DEFINITIONS

Before describing the present invention in detail, it is to be understood that this invention is not limited to particular oligonucleotides, methods, compositions, kits, systems, computers, or computer readable media, which can, of course, vary. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the present invention, the following terminology and grammatical variants will be used in accordance with the definitions set forth below.

The term "5' to 3' nuclease activity" refers to a 5' to 3' exonuclease activity associated with some nucleotide incorporating biocatalysts, such as nucleic acid polymerases in which nucleotides are sequentially removed from the 5' end of an oligonucleotide, a 5' to 3' endonuclease activity in which cleavage occurs more than one phosphodiester bond (nucleotide) from the 5' end, or both activities. An exemplary substrate for 5' to 3' endonuclease activity-dependent cleavage on a probe-template hybridization complex is a displaced single-stranded nucleic acid, a fork-like structure, with hydrolysis occurring at the phosphodiester bond joining the displaced region with the base-paired portion of the strand, as discussed in, e.g., Holland et al. (1991) *Proc. Natl. Acad. Sci. USA* 88:7276-80, which is incorporated by reference.

A "5'-nuclease probe" refers to an oligonucleotide that comprises at least one light emitting labeling moiety and that is used in a 5'-nuclease reaction to effect target nucleic acid detection. In some embodiments, for example, a 5'-nuclease probe includes only a single light-emitting moiety (e.g., a fluorescent dye, etc.). In certain embodiments, 5'-nuclease probes include regions of self-complementarity such that the probes are capable of forming hairpin structures under selected conditions. Typically, the light emission modifiers described herein modify light emission from intact, full-length 5'-nuclease probes to a greater extent than from labeled fragments of such probes, which fragments are generated from the full-length probes during exo- and/or endonucleolytic cleavage steps of 5'-nuclease reactions. To further illustrate, in some embodiments a 5'-nuclease probe comprises at least two labeling moieties and emits radiation of increased intensity after one of the two labels is cleaved or otherwise separated from the oligonucleotide. In certain embodiments, for example, a 5'-nuclease probe is labeled with two different fluorescent dyes, e.g., a 5' terminus reporter dye and the 3' terminus quencher dye or moiety. In some embodiments, 5'-nuclease probes are labeled at one or more positions other than, or in addition to, terminal positions. When the probe is intact, energy transfer typically occurs between the two fluorophores such that fluorescent emission from the reporter dye is quenched at least in part. During an extension step of a polymerase chain reaction, for example, a 5'-nuclease probe bound to a template nucleic acid is cleaved by the 5' to 3' nuclease activity of, e.g., a Taq polymerase or another polymerase having this activity such that the fluorescent emission of the reporter dye is no longer quenched. Exemplary 5'-nuclease probes are also described in, e.g., U.S. Pat. No. 5,210,015, entitled "HOMOGENEOUS ASSAY SYSTEM USING THE NUCLEASE ACTIVITY OF A NUCLEIC ACID POLYMERASE," issued May 11, 1993 to Gelfand et al., U.S. Pat. No. 5,994,056, entitled "HOMOGENEOUS METHODS FOR NUCLEIC ACID AMPLIFICATION AND DETECTION," issued Nov. 30, 1999 to Higuchi, and U.S. Pat. No. 6,171,785, entitled "METHODS AND DEVICES FOR HEMOGENEOUS NUCLEIC ACID AMPLIFICATION AND DETECTOR," issued Jan. 9, 2001 to Higuchi, which are each incorporated by reference. In other embodiments, two different probes are used, one labeled with a reporter dye and the other with a quencher dye, in an arrangement such that fluorescent resonance energy transfer can occur when both are hybridized to the target nucleic acid. In still other embodiments, a 5' nuclease probe may be labeled with two or more different reporter dyes and the 3' terminus quencher dye or moiety.

A "5' nuclease reaction" or "5' nuclease assay" of target or template, primer, and probe (e.g., 5'-nuclease probes, etc.) nucleic acids refers to the degradation of a probe hybridized to the template nucleic acid when the primer is extended by a nucleotide incorporating biocatalyst having 5' to 3' nuclease activity, as described further below. 5' nuclease reactions are also described in, e.g., U.S. Pat. No. 6,214,979, entitled "HOMOGENEOUS ASSAY SYSTEM," issued Apr. 10, 2001 to Gelfand et al., U.S. Pat. No. 5,804,375, entitled "REACTION MIXTURES FOR DETECTION OF TARGET NUCLEIC ACIDS," issued Sep. 8, 1998 to Gelfand et al., U.S. Pat. No. 5,487,972, entitled "NUCLEIC ACID DETECTION BY THE 5'-3' EXONUCLEASE ACTIVITY OF POLYMERASES ACTING ON ADJACENTLY HYBRIDIZED OLIGONUCLEOTIDES," issued Jan. 30, 1996 to Gelfand et al., and U.S. Pat. No. 5,210,015, supra, which are each incorporated by reference.

An "amplicon" refers to a molecule made by amplifying a nucleic acid molecule, e.g., as occurs in a nucleic acid amplification reaction, such as a polymerase chain reaction ("PCR"), a strand displacement amplification (SDA), transcription mediated amplification (TMA), ligase chain reaction (LCR), or other nucleic acid amplification technique. Typically, an amplicon is a copy of a selected nucleic acid (e.g., a template or target nucleic acid) or is complementary thereto.

An "amplification reaction" refers to a reaction involving the replication of one or more target nucleic acid sequences or complements thereto. Exemplary amplification reactions include PCR, ligase chain reactions (LCR), among many others.

The term "baseline emission of light" in the context of a labeled oligonucleotide refers a detectable emission of light from the oligonucleotide prior to being contacted with a light emission modifier. Certain 5'-nuclease probes, for example, emit detectable amounts of residual light despite the presence of one or more quencher moieties incorporated into the probe design. This baseline or background light emission tends to limit the signal to noise ratio of 5'-nuclease reactions. Moreover, this baseline emission of light generally increases additively in multiplexed detection formats where multiple labeled probes are pooled with one another. This additive increase in the baseline emission of light also occurs when the amount of a single probe is increased in a given application.

The term "cleavage" in the context of 5'-nuclease reactions refers to the degradation or fragmentation (hydrolysis) of 5'-nuclease probes by the 5' to 3' nuclease activity associated with various polymerases typically utilized in those reactions.

A "complement" of a nucleic acid refers to at least a nucleic acid segment that can combine in an antiparallel association or hybridize with at least a subsequence of that nucleic acid. The antiparallel association can be intramolecular, e.g., in the form of a hairpin loop within a nucleic acid, or intermolecular, such as when two or more single-stranded nucleic acids hydridize with one another. Certain bases not commonly found in natural nucleic acids may be included in the nucleic acids referred to herein and include, for example, inosine, 7-deazaguanine and those discussed below. Complementarity need not be perfect; stable duplexes, for example, may contain mismatched base pairs or unmatched bases. Those skilled in the art of nucleic acid technology can determine duplex stability by empirically considering a number of variables including, for example, the length of a region of complementarity, base composition and sequence of nucleotides in a region of complementarity, ionic strength, and incidence of mismatched base pairs.

"Corresponding" means identical to or complementary to a designated sequence of nucleotides in a nucleic acid. The exact application of the term will be evident to one of skill in the art by the context in which the term is used.

A "diazine dye" refers to any of a class of organic chemical compounds containing a benzene ring in which two of the carbon atoms have been replaced by nitrogen atoms. Exemplary diazine dyes include an azocarmine dye, a phenazine dye, and diethylsafraninazodimethylaniline chloride (Janus Green B or Diazine Green 5).

Nucleic acids "hybridize" when complementary single strands of nucleic acid pair to give a double-stranded nucleic acid sequence. Hybridization occurs due to a variety of well-characterized forces, including hydrogen bonding, solvent exclusion, and base stacking. An extensive guide to nucleic hybridization may be found in Tijssen, *Laboratory Techniques in Biochemistry and Molecular Biology—Hybridization with Nucleic Acid Probes*, part I, chapter 2, "Overview of principles of hybridization and the strategy of nucleic acid probe assays," Elsevier (1993).

The phrase "in solution" refers to an assay or reaction condition in which the components of the assay or reaction are not attached to a solid support in a fluid medium.

A "label" or "labeling moiety" refers to a moiety attached (covalently or non-covalently), or capable of being attached, to a molecule, which moiety provides or is capable of providing information about the molecule (e.g., descriptive, identifying, etc. information about the molecule) or another molecule with which the labeled molecule interacts (e.g., hybridizes, etc.). Exemplary labels include fluorescent labels (including, e.g., quenchers or absorbers), non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like. To further illustrate, fluorescent labels may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include, e.g., FAM, HEX, TET, JOE, NAN and ZOE. Dyes of the rhodamine family include, e.g., Texas Red, ROX, R110, R6G, and TAMRA. FAM, HEX, TET, JOE, NAN, ZOE, ROX, R110, R6G, and TAMRA are commercially available from, e.g., Perkin-Elmer, Inc. (Wellesley, Mass., USA), and Texas Red is commercially available from, e.g., Molecular Probes, Inc. (Eugene, Oreg.). Dyes of the cyanine family include, e.g., Cy2, Cy3, Cy5, and Cy7, and are commercially available from, e.g., Amersham Biosciences Corp. (Piscataway, N.J., USA). Additional labels are referred to herein or are otherwise known in the art.

A "light emission modifier" refers to a substance that non-covalently associates with a nucleic acid in a mixture and that changes the detectable emission of radiation from a radiation source associated with the nucleic acid when the substance is proximal to the radiation source. In some embodiments, for example, certain light emission modifiers described herein reduce or quench the emission of light that would otherwise be emitted (e.g., a baseline emission of light) from oligonucleotides that include at least one light-emitting moiety (e.g., 5'-nuclease probes, etc.) when the light emission modifiers are contacted with those oligonucleotides. Light emission modifiers are typically soluble and in these embodiments are also referred to as "soluble quenchers" or "soluble light emission modifiers". In addition, without being bound by any particular theory, it is believed that a light emission modifier generally binds to nucleic acids in a length dependent manner. That is, light emission modifiers typically bind to longer nucleic acids to a greater extent than to relatively shorter nucleic acids. Accordingly, the extent to which a light emission modifier modifies the emission of light from a given labeled nucleic acid is typically proportional to the length of that nucleic acid. For example, if a labeled oligonucleotide is cleaved in a 5'-nuclease reaction, a particular light emission modifier will generally modify (e.g., quench, etc.) the emission of light from labeled fragments of the oligonucleotide to a lesser extent than from the intact oligonucleotide. Exemplary light emission modifiers include various diazine and thiazines dyes, which are described further herein.

A "light-emitting labeling moiety" refers to a labeling moiety that generates or is capable of generating detectable radiation or light. Certain light-emitting labeling moieties generate light, e.g., by fluorescence, chemiluminescence, bioluminescence, or the like.

A "mixture" refers to a combination of two or more different components. A "reaction mixture" refers a mixture that comprises molecules that can participate in and/or facilitate a given reaction. To illustrate, a amplification reaction mixture generally includes a solution containing reagents necessary to carry out an amplification reaction, and typically contains primers, a nucleic acid polymerase, dNTPs, and a divalent metal cation in a suitable buffer. A reaction mixture is referred to as complete if it contains all reagents necessary to carry out the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Reaction components may also be formulated in a dry form, e.g., tablets, and may then be reconstituted prior to use. Furthermore, it will be understood by one of skill in the art that reaction components are packaged separately for commercialization and that useful commercial kits may contain any subset of the reaction components which includes the modified primers of the invention.

A "moiety" or "group" refers to one of the portions into which something, such as a molecule, is divided (e.g., a functional group, substituent group, or the like). For example, a probe may be considered an oligonucleotide that optionally comprises a quencher moiety, a labeling moiety, or the like.

The term "nucleic acid" refers to a polymer of monomers that can be corresponded to a ribose nucleic acid (RNA) or deoxyribose nucleic acid (DNA) polymer, or analog thereof. This includes polymers of nucleotides such as RNA and DNA, as well as modified forms thereof, peptide nucleic acids (PNAs), locked nucleic acids (LNA™s), and the like. In certain applications, the nucleic acid can be a polymer that includes multiple monomer types, e.g., both RNA and DNA subunits. A nucleic acid can be or include, e.g., a chromosome or chromosomal segment, a vector (e.g., an expression vector), an expression cassette, a naked DNA or RNA polymer, an amplicon, an oligonucleotide, a primer, a probe, etc. A nucleic acid can be e.g., single-stranded or double-stranded. Unless otherwise indicated, a particular nucleic acid sequence optionally comprises or encodes complementary sequences, in addition to any sequence explicitly indicated.

A nucleic acid is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) *Tetrahedron* 49(10):1925 and the references therein; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26:1419), phosphorothioate (Mag et al. (1991) *Nucleic Acids Res.* 19:1437 and U.S. Pat. No. 5,644,048), phosphorodithioate (Briu et al. (1989) *J. Am. Chem. Soc.* 111:2321), O-methylphosphoroamidite linkages (Eckstein, *Oligonucleotides and Analogues: A Practical Approach*, Oxford University Press (1992)), and peptide nucleic acid backbones and linkages (Egholm (1992) *J. Am. Chem. Soc.* 114:1895; Meier et al. (1992) *Chem. Int. Ed. Engl.* 31:1008; Nielsen (1993) *Nature* 365:566; and Carlsson et al. (1996) *Nature* 380:207), which references are each incorporated by reference. Other analog nucleic acids include those with positively charged backbones (Denpcy et al. (1995) *Proc. Natl. Acad. Sci. USA* 92:6097); non-ionic backbones (U.S. Pat. Nos. 5,386,023, 5,637,684, 5,602,240, 5,216,141 and 4,469,863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (Jenkins et al. (1995) *Chem. Soc. Rev.* pp 169-176, which is incorporated by reference). Several nucleic acid analogs are also described in, e.g., Rawls, *C & E News* Jun. 2, 1997 page 35, which is incorporated by reference. These modifications of the ribose-phosphate backbone may be done to facilitate the addition of additional moieties such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified bases, many of which are described, or otherwise referred to, herein. In particular, many non-naturally occurring bases are described further in, e.g., Seela et al. (1991) *Helv. Chim. Acta* 74:1790, Grein et al. (1994) *Bioorg. Med. Chem. Lett.* 4:971-976, and Seela et al. (1999) *Helv. Chim. Acta* 82:1640, which are each incorporated by reference. To further illustrate, certain bases used in nucleotides that act as melting temperature ($T_m$) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

Additional examples of modified bases and nucleotides are also described in, e.g., U.S. Pat. No. 5,484,908, entitled "OLIGONUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDINES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

A "nucleotide" refers to an ester of a nucleoside, e.g., a phosphate ester of a nucleoside. To illustrate, a nucleotide can include 1, 2, 3, or more phosphate groups covalently linked to a 5' position of a sugar moiety of the nucleoside.

A "nucleotide incorporating biocatalyst" refers to a catalyst that catalyzes the incorporation of nucleotides into a nucleic acid. Nucleotide incorporating biocatalysts are typically enzymes. An "enzyme" is a protein-based catalyst that acts to reduce the activation energy of a chemical reaction involving other compounds or "substrates." A "nucleotide incorporating enzyme" refers to an enzyme that catalyzes the incorporation of nucleotides into a nucleic acid. Exemplary nucleotide incorporating enzymes include, e.g., DNA polymerases, RNA polymerases, terminal transferases, reverse transcriptases, telomerases, polynucleotide phosphorylases, and the like. Other biocatalysts may be DNA-based ("DNAzymes") or RNA-based ("ribozymes"). A "thermostable enzyme" refers to an enzyme that is stable to heat, is heat resistant and retains sufficient catalytic activity when subjected to elevated temperatures for selected periods of time. For example, a thermostable polymerase retains sufficient activity to effect subsequent primer extension reactions when subjected to elevated temperatures for the time necessary to effect denaturation of double-stranded nucleic acids. Heating conditions necessary for nucleic acid denaturation are well known in the art and are exemplified in U.S. Pat. No. 4,683,202, entitled "PROCESS FOR AMPLIFYING NUCLEIC ACID SEQUENCES," issued Jul. 28, 1987 to Mullis and U.S. Pat. No. 4,683,195, entitled "PROCESS FOR AMPLIFYING, DETECTING, AND/OR-CLONING NUCLEIC ACID SEQUENCES," issued Jul. 28, 1987 to Mullis et al., which are both incorporated by reference. As used herein, a thermostable polymerase is typically suitable for use in a temperature cycling reaction such as a PCR or a 5'-nuclease reaction. For a thermostable polymerase, enzymatic activity refers to the catalysis of the polymerization of the nucleotides in the proper manner to form primer extension products that are complementary to a template nucleic acid.

An "oligonucleotide" or a "polynucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) *Meth. Enzymol.* 68:90-99; the phosphodiester method of Brown et al. (1979) *Meth. Enzymol.* 68:109-151; the diethylphosphoramidite method of Beaucage et al. (1981) *Tetrahedron Lett.* 22:1859-1862; the triester method of Matteucci et al. (1981) *J. Am. Chem. Soc.* 103:3185-3191; automated synthesis methods; or the solid support method of U.S. Pat.

No. 4,458,066, entitled "PROCESS FOR PREPARING POLYNUCLEOTIDES," issued Jul. 3, 1984 to Caruthers et al., or other methods known in the art. All of these references are incorporated by reference.

The term "probe nucleic acid" or "probe" refers to a labeled or unlabeled oligonucleotide capable of selectively hybridizing to a target or template nucleic acid under suitable conditions. Typically, a probe is sufficiently complementary to a specific target sequence contained in a nucleic acid sample to form a stable hybridization duplex with the target sequence under a selected hybridization condition, such as, but not limited to, a stringent hybridization condition. A hybridization assay carried out using the probe under sufficiently stringent hybridization conditions permits the selective detection of a specific target sequence. The term "hybridizing region" refers to that region of a nucleic acid that is exactly or substantially complementary to, and therefore hybridizes to, the target sequence. For use in a hybridization assay for the discrimination of single nucleotide differences in sequence, the hybridizing region is typically from about 8 to about 100 nucleotides in length. Although the hybridizing region generally refers to the entire oligonucleotide, the probe may include additional nucleotide sequences that function, for example, as linker binding sites to provide a site for attaching the probe sequence to a solid support or the like, as sites for hybridization of other oligonucleotides, as restriction enzymes sites or binding sites for other nucleic acid binding enzymes, etc. In certain embodiments, a probe of the invention is included in a nucleic acid that comprises one or more labels (e.g., a reporter dye, a quencher moiety, etc.), such as a 5'-nuclease probe, a FRET probe, a molecular beacon, or the like, which can also be utilized to detect hybridization between the probe and target nucleic acids in a sample. In some embodiments, the hybridizing region of the probe is completely complementary to the target sequence. However, in general, complete complementarity is not necessary (i.e., nucleic acids can be partially complementary to one another); stable duplexes may contain mismatched bases or unmatched bases. Modification of the stringent conditions may be necessary to permit a stable hybridization duplex with one or more base pair mismatches or unmatched bases. Sambrook et al., *Molecular Cloning: A Laboratory Manual*, 3rd Ed., Cold Spring Harbor Laboratory Press, Cold Spring Harbor, N.Y. (2001), which is incorporated by reference, provides guidance for suitable modification. Stability of the target/probe duplex depends on a number of variables including length of the oligonucleotide, base composition and sequence of the oligonucleotide, temperature, and ionic conditions. One of skill in the art will recognize that, in general, the exact complement of a given probe is similarly useful as a probe. One of skill in the art will also recognize that, in certain embodiments, probe nucleic acids can also be used as primer nucleic acids. Exemplary probe nucleic acids include 5'-nuclease probes, molecular beacons, among many others known to persons of skill in the art.

A "primer nucleic acid" or "primer" is a nucleic acid that can hybridize to a target or template nucleic acid and permit chain extension or elongation using, e.g., a nucleotide incorporating biocatalyst, such as a polymerase under appropriate reaction conditions. A primer nucleic acid is typically a natural or synthetic oligonucleotide (e.g., a single-stranded oligodeoxyribonucleotide, etc.). Although other primer nucleic acid lengths are optionally utilized, they typically comprise hybridizing regions that range from about 8 to about 100 nucleotides in length. Short primer nucleic acids generally utilize cooler temperatures to form sufficiently stable hybrid complexes with template nucleic acids. A primer nucleic acid that is at least partially complementary to a subsequence of a template nucleic acid is typically sufficient to hybridize with the template for extension to occur. A primer nucleic acid can be labeled (e.g., a SCORPION® primer, etc.), if desired, by incorporating a label detectable by, e.g., spectroscopic, photochemical, biochemical, immunochemical, chemical, or other techniques. To illustrate, useful labels include radioisotopes, fluorescent dyes, electron-dense reagents, enzymes (as commonly used in ELISAs), biotin, or haptens and proteins for which antisera or monoclonal antibodies are available. Many of these and other labels are described further herein and/or otherwise known in the art. One of skill in the art will recognize that, in certain embodiments, primer nucleic acids can also be used as probe nucleic acids.

A "quencher moiety" or "quencher" refers to a moiety that reduces and/or is capable of reducing the detectable emission of radiation, e.g., fluorescent or luminescent radiation, from a source ("donor") that would otherwise have emitted this radiation at a particular $\lambda_{max}$. A quencher typically reduces the detectable radiation emitted by the source by at least 50%, typically by at least 80%, and more typically by at least 90%. Certain quenchers may re-emit the energy absorbed from, e.g., a fluorescent dye in a signal characteristic for that quencher and thus a quencher can also be a "label." This phenomenon is generally known as fluorescent resonance energy transfer or FRET. Alternatively, a quencher may dissipate the energy absorbed from a fluorescent dye in a form other than light, e.g., as heat. Molecules commonly used in FRET include, for example, fluorescein, FAM, JOE, rhodamine, R6G, TAMRA, ROX, DABCYL, and EDANS. Whether a fluorescent dye is a donor or an acceptor is defined by its excitation and emission spectra, and the fluorescent dye with which it is paired. For example, FAM is most efficiently excited by light with a wavelength of 488 nm, and emits light with a spectrum of 500 to 650 nm, and an emission maximum of 525 nm. FAM is a suitable donor label for use with, e.g., TAMRA as a quencher, which has at its excitation maximum 514 m-n. Exemplary non-fluorescent or dark quenchers that dissipate energy absorbed from a fluorescent dye include the Black Hole Quenchers™ marketed by Biosearch Technologies, Inc. (Novato, Calif., USA), and the ECLIPSE® Dark Quenchers (Epoch Biosciences, Bothell, Wash., USA). The Black Hole Quenchers™ (BHQ) are structures comprising at least three radicals selected from substituted or unsubstituted aryl or heteroaryl compounds, or combinations thereof, wherein at least two of the residues are linked via an exocyclic diazo bond (see, e.g., International Publication No. WO 01/86001, entitled "DARK QUENCHERS FOR DONOR-ACCEPTOR ENERGY TRANSFER," published Nov. 15, 2001 by Cook et al., which is incorporated by reference). Exemplary quenchers are also provided in, e.g., U.S. Pat. No. 6,465,175, entitled "OLIGONUCLEOTIDE PROBES BEARING QUENCHABLE FLUORESCENT LABELS, AND METHODS OF USE THEREOF," which issued Oct. 15, 2002 to Horn et al., which is incorporated by reference. Quenchers apply both to molecules that do not re-emit absorbed light as light of a longer wavelength (non-fluorescent) or by re-emitting light at a wavelength that is outside the range that is detected (fluorescent).

In its broadest sense, a quencher refers to any molecule that is capable of reducing a light emission. It is noted that there are instances where a quencher in not necessarily a FRET quencher. There is not a requirement that a quencher work by a strict "FRET" mechanism, and indeed, a quencher can function by any mechanism. There is no requirement for a spectral overlap between the fluorophore and the quencher. It is noted that quenching can include dynamic quenching (Forster, Dexter etc.), and static quenching (ground state complex). Quenching mechanisms can involve energy transfer, photoelectron transfer, proton coupled electron transfer, dimer formation between closely situated fluorophores, transient excited state interactions, collisional quenching, or formation of non-fluorescent ground state species. See, e.g., *Principles of Fluorescence Spectroscopy*, by Joseph Lakowicz; and *Handbook of Fluorescent Probes* by Richard Haugland.

A "sequence" of a nucleic acid refers to the order and identity of nucleotides in the nucleic acid. A sequence is typically read in the 5' to 3' direction.

A "single-labeled oligonucleotide" refers to an oligonucleotide that includes only one labeling moiety. In certain embodiments, the labeling moiety is light emitting.

A substance is "soluble" when it is capable of being free in solution. For example, soluble light emission modifiers typically interact non-covalently with nucleic acids when they are free in solution.

The terms "stringent" or "stringent conditions", as used herein, denote hybridization conditions of low ionic strength and high temperature, as is well known in the art. See, e.g., Sambrook et al., *Molecular Cloning: A Laboratory Manual*, $3^{rd}$ Ed., Cold Spring Harbor Laboratory Press, Cold Spring Harbor, N.Y. (2001); *Current Protocols in Molecular Biology* (Ausubel et al., ed., J. Wiley & Sons Inc., New York, 1997); Tijssen (1993), supra, each of which is incorporated by reference. Generally, stringent conditions are selected to be about 5-30° C. lower than the thermal melting point ($T_m$) for the specified sequence at a defined ionic strength and pH. Alternatively, stringent conditions are selected to be about 5-15° C. lower than the $T_m$ for the specified sequence at a defined ionic strength and pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are hybridized at equilibrium).

A "subject" refers to an organism. Typically, the organism is a mammalian organism, particularly a human organism. In certain embodiments, for example, a subject is a patient suspected of having a genetic disorder, disease state, or other condition.

A "subsequence," "segment," or "fragment" refers to any portion of an entire nucleic acid sequence.

A "thiazine dye" refers to any of a class of organic chemical compounds containing a tricyclic aromatic fused ring system, where two of the carbons in the middle ring are replaced by a nitrogen atom and a sulfur atom. Exemplary thiazine dyes include methylene blue, methylene green, thionin, 1,9-dimethylmethylene blue, sym-dimethylthionin, toluidine blue O, new methylene blue, methylene violet bernthsen, azure A, azure B, and azure C.

The term "template nucleic acid" or "target nucleic acid" refers to a nucleic acid that is to be amplified, detected, or otherwise analyzed.

Objects "thermally communicate" with one another when thermal energy is transferred or capable of being transferred between the objects. In certain embodiments of the systems described herein, for example, thermal modulators thermally communicate with containers to modulate temperature in the containers.

As used herein, the term "$T_m$" is used in reference to the "melting temperature." The melting temperature is the temperature at which one half of a population of double-stranded polynucleotides or nucleobase oligomers (e.g., hybridization complexes), in homoduplexes or heteroduplexes, become dissociated into single strands. The prediction of a $T_m$ of a duplex polynucleotide takes into account the base sequence as well as other factors including structural and sequence characteristics and nature of the oligomeric linkages. Methods for predicting and experimentally determining $T_m$ are known in the art.

For example, a $T_m$ is traditionally determined by a melting curve, where a duplex nucleic acid molecule is heated in a controlled temperature program, and the state of association/dissociation of the two single strands in the duplex is monitored and plotted until reaching a temperature where the two strands are completely dissociated. The $T_m$ is read from this melting curve. Alternatively, a $T_m$ can be determined by an annealing curve, where a duplex nucleic acid molecule is heated to a temperature where the two strands are completely dissociated. The temperature is then lowered in a controlled temperature program, and the state of association/dissociation of the two single strands in the duplex is monitored and plotted until reaching a temperature where the two strands are completely annealed. The $T_m$ is read from this annealing curve.

It is not intended that the invention be limited to any particular method for the determination of Tm. Methods for the experimental determination of $T_m$ are widely known in the art and are described in a variety of sources, e.g., Liew et al., "Genotyping of Single-Nucleotide Polymorphism by High-Resolution Melting of Small Amplicons," Clinical Chemistry 50(7):1156-1164 (2004); Reed and Wittwer "Sensitivity and Specificity of Single-Nucleotide Polymorphism Scanning by High-Resolution Melting Analysis," Clinical Chemistry 50(10):1748-1754 (2004); Zhou et al., "Closed-Tube Genotyping with Unlabeled Oligonucleotide Probes and a Saturating DNA Dye," Clinical Chemistry 50(8):1328-1335 (2004); and Zhou et al., "High-resolution DNA melting curve analysis to establish HLA genotypic identity," Tissue Antigens 64:156-164 (2004). Melting/annealing curve analysis instrumentation is commercially available from a variety of manufacturers.

As used herein, the term "sample" is used in its broadest sense, and refers to any material subject to analysis. The term "sample" refers typically to any type of material of biological origin, for example, any type of material obtained from animals or plants. A sample can be, for example, any fluid or tissue such as blood or serum, and furthermore, can be human blood or human serum. A sample can be cultured cells or tissues, cultures of microorganisms (prokaryotic or eukaryotic), or any fraction or products produced from or derived from biological materials (living or once living). Optionally, a sample can be purified, partially purified, unpurified, enriched or amplified. Where a sample is purified or enriched, the sample can comprise principally one component, e.g., nucleic acid. More specifically, for example, a purified or amplified sample can comprise total cellular RNA, total cellular mRNA, cDNA, cRNA, or an amplified product derived there from.

The sample used in the methods of the invention can be from any source, and is not limited. Such sample can be an amount of tissue or fluid isolated from an individual or individuals, including, but not limited to, for example, skin, plasma, serum, whole blood, blood products, spinal fluid, saliva, peritoneal fluid, lymphatic fluid, aqueous or vitreous humor, synovial fluid, urine, tears, blood cells, blood products, semen, seminal fluid, vaginal fluids, pulmonary effusion, serosal fluid, organs, bronchio-alveolar lavage, tumors, paraffin embedded tissues, etc. Samples also can include constituents and components of in vitro cell cultures, including, but not limited to, conditioned medium resulting from the growth of cells in the cell culture medium, recombinant cells, cell components, etc.

As used herein, the expression "hepatitis C virus type" refers to the categorization of a hepatitis C virus (HCV) based on its genomic organization. The categorization of an HCV isolate into a particular type category reflects its genomic relatedness to other HCV isolates and its relatively lesser relatedness to other HCV isolates. As used herein, HCV typing nomenclature is consistent with the widely adopted nomenclature proposed by Simmonds et al (1994) Letter, Hepatology 19:1321-1324. See, also, Zein (2000) "Clinical Significance of Hepatitis C Virus Genotypes," Clinical Microbiol. Reviews 13(2):223-235; Maertens and Stuyver (1997) "Genotypes and Genetic Variation of Hepatitis C Virus," p. 182-233, In Harrison, and Zuckerman (eds.), *The Molecular Medicine of Viral Hepatitis*, John Wiley & Sons, Ltd., Chichester, England.). The system of Simmonds et al (1994) places the known HCV isolates into one of eleven (11) HCV genotypes, namely genotypes 1 through 11. Each genotype is further subdivided into groupings termed subtypes that reflect relatedness among strains of the same genotype. An HCV subtype is written by a lowercase roman letter following the genotype, e.g., subtype 1a, subtype 1c, subtype 6a, etc. Genetic variants found within an individual isolate are termed quasispecies. Approximately 78 HCV subtypes encompassing all 11 genotypes are known worldwide; the number of subtypes is not static; as more HCV isolates are studied and sequenced, it is likely that additional subtypes (and possibly genotypes) may be recognized. As used herein, the term "virus types" can refer to either genotypes or subtypes.

Some reports (see, e.g., Robertson et al., (1998) Arch. Virol., 143(12):2493-2503) suggest that viral genomic organization is best represented by the creation of viral clades, reflecting the observation that some HCV genotypes are more closely related to each other than to other HCV genotypes. In this system, clades 1, 2, 4 and 5 correspond to genotypes 1, 2, 4 and 5, while lade 3 comprises genotypes 3 and 10, and clade 6 comprises genotypes 6, 7, 8, 9 and 11. The description of the present invention does not use the lade nomenclature.

Additional detailed description of HCV genotypes and genotyping methodologies is found in cofiled U.S. patent application Ser. No. 11/474,125, filed on Jun. 23, 2006, entitled "PROBES AND METHODS FOR HEPATITIS C VIRUS TYPING USING SINGLE PROBE ANALYSIS," by Gupta and Will; and also in cofiled U.S. patent application Ser. No. 11/474,092, filed on Jun. 23, 2006, entitled "PROBES AND METHODS FOR HEPATITIS C VIRUS TYPING USING MULTIDIMENSIONAL PROBE ANALYSIS," by Gupta and Will. The entire content of these two cofiled applications are hereby incorporated by reference in their entirety for all purposes.

As used herein, the expression "derived from" refers to a component that is isolated from or made using a specified sample, molecule, organism or information from the specified molecule or organism. For example, a nucleic acid molecule that is derived from a hepatitis C virus can be, for example, a molecule of the HCV genome, or alternatively, a transcript from the HCV genome, or alternatively, a synthetic nucleic acid comprising a polynucleotide sequence that corresponds to an HCV polynucleotide sequence.

As used herein, the term "monitor" refers to periodic or continuous surveillance, testing, data collecting and/or quantitation. Monitoring can be automated, and the information (e.g., a dataset) gathered during the monitoring can be printed or can be compiled as a computer readable and/or computer storable format.

As used herein, the term "correlate" refers to making a relationship between two or more variables, values or entities. If two variables correlate, the identification of one of those variables can be used to determine the value of the remaining variable.

As used herein, the term "kit" is used in reference to a combination of articles that facilitate a process, method, assay, analysis or manipulation of a sample. Kits can contain written instructions describing how to use the kit (e.g., instructions describing the methods of the present invention), chemical reagents or enzymes required for the method, primers and probes, as well as any other components.

As used herein, the expression "asymmetric PCR" refers to the preferential PCR amplification of one strand of a DNA target by adjusting the molar concentration of the primers in a primer pair so that they are unequal. An asymmetric PCR reaction produces a predominantly single-stranded product and a smaller quantity of a double-stranded product as a result of the unequal primer concentrations. As asymmetric PCR proceeds, the lower concentration primer is quantitatively incorporated into a double-stranded DNA amplicon, but the higher concentration primer continues to prime DNA synthesis, resulting in continued accumulation of a single stranded product.

BRIEF DESCRIPTION OF THE DRAWINGS

FIG. 22 is a photograph of a polyacrylamide gel that shows an analysis of HCV PCR reactions with 20,000 copies of HCV DNA, various probes, and various amounts of methylene blue. Panels A and B represent duplicate reactions.

FIG. 23 is an amplification plot (ordinate represents relative fluorescence, abscissa represents the cycle number) that shows PCR detection of IQS (internal quantitation standard) DNA with a HEX labeled single-labeled probe in the presence of various concentrations of methylene blue.

FIG. 30 is an amplification plot (ordinate represents relative fluorescence, abscissa represents the cycle number) that shows a comparison of signals obtained from a single-labeled probe and a dual-labeled probe in the presence of 40 µg/mL of a light emission modifier, methylene blue in the detection of 2-200,000 input copies of HIV DNA.

FIG. 31 is a photograph of a polyacrylamide gel that shows an analysis of HCV and HIV PCR reactions with 2-200,000 input copies of DNA, in the presence of 40 µg/mL methylene blue. Panels A and B represent HCV and HIV reactions, respectively.

The results of the four separate experiments are overlaid on the same graph. A representative set of data is shown.

Figure 59:
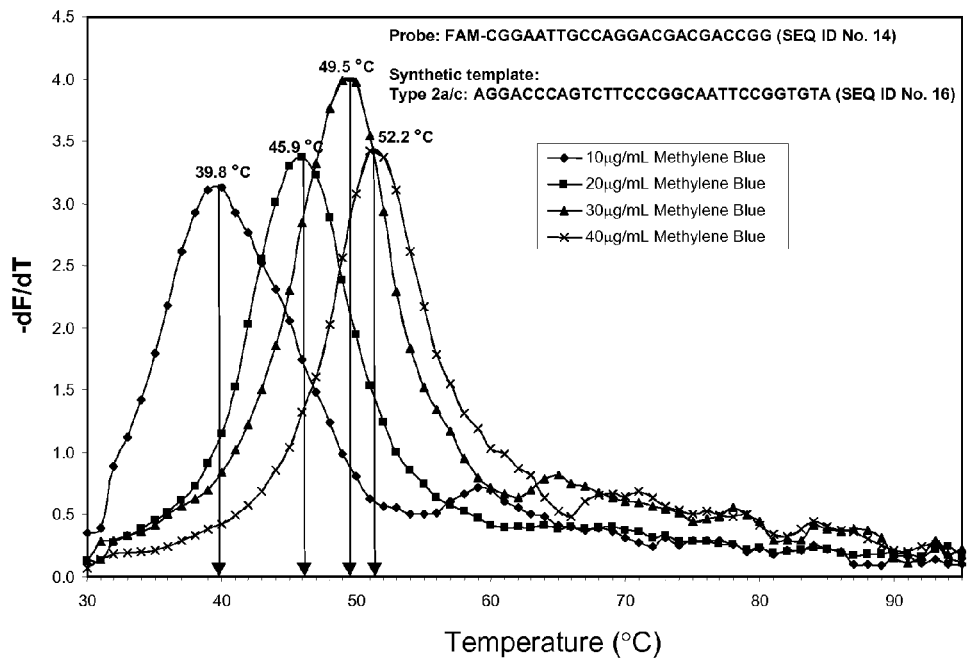

FIG. 59 provides first derivative plot of a melting curve (Tm) analysis using a FAM single-labeled HCV genotyping probe, a synthetic nucleic acid target corresponding to HCV genotype 2a/c and four increasing concentrations of methylene blue. The sequences of the probe and synthetic template are shown, which form a duplex with three mismatch positions. The results of the four separate experiments are overlaid on the same graph. A representative set of data is shown.

Figure 60:
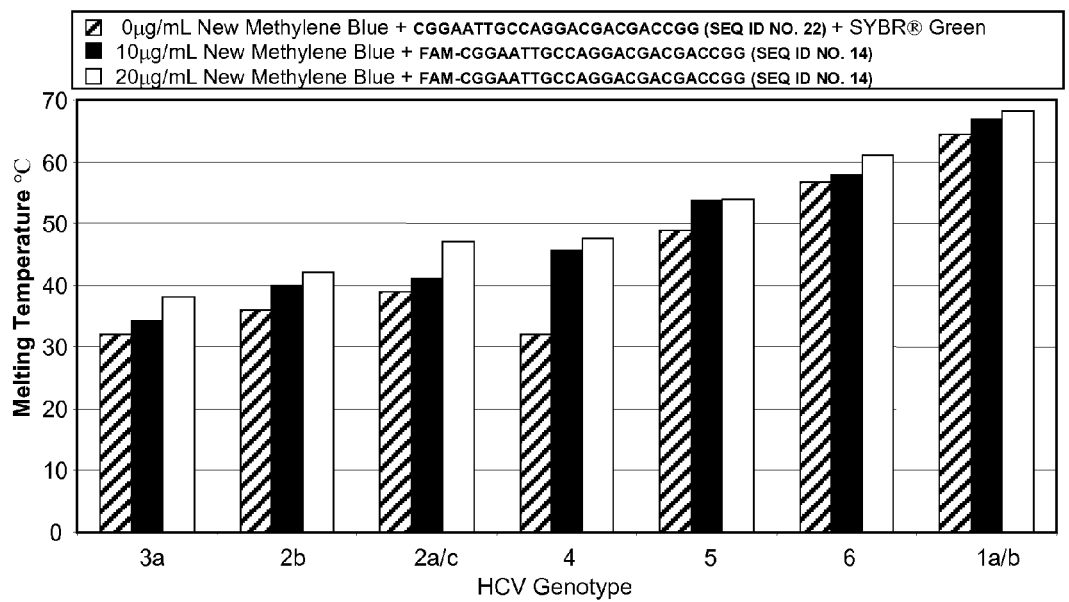

FIG. 60 provides a bar graph summary of Tm determinations using the HCV probes indicated with the various HCV synthetic templates shown. The Tm determinations were made using various concentrations of new methylene blue soluble quencher, as indicated. In one set of Tm determinations, a non-labeled probe was used in conjunction with SYBR® Green indicator. A representative set of data is shown.

Figures 52A, 52B:
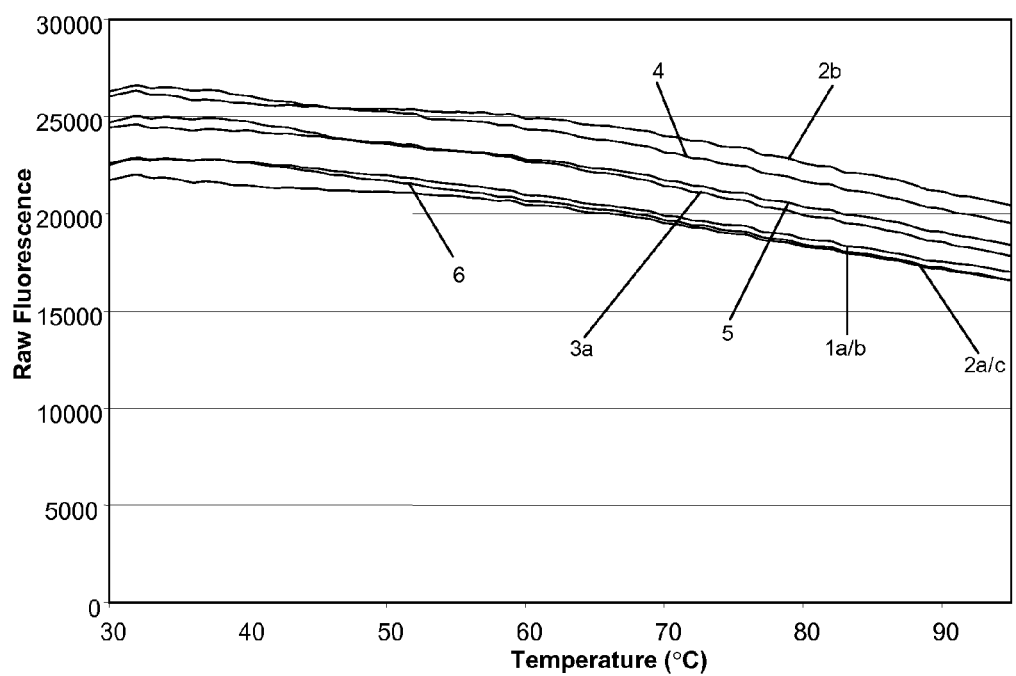
FIG. 52A provides the nucleotide sequence of a FAM-labeled HCV-specific probe.
FIG. 52B provides a melting curve (Tm) analysis showing raw fluorescence plotted as a function of temperature using the single-labeled HCV genotyping probe shown in FIG. 52A and synthetic nucleic acid targets. The melting reaction does not include a soluble quencher. Fluorescence was measured using an excitation filter at 485 nm with a 20 nm bandwidth, and an emission filter at 520 nm with a 10 nm bandwidth. The results of the seven separate experiments are overlaid on the same graph. A representative set of data is shown.
Figure 61:
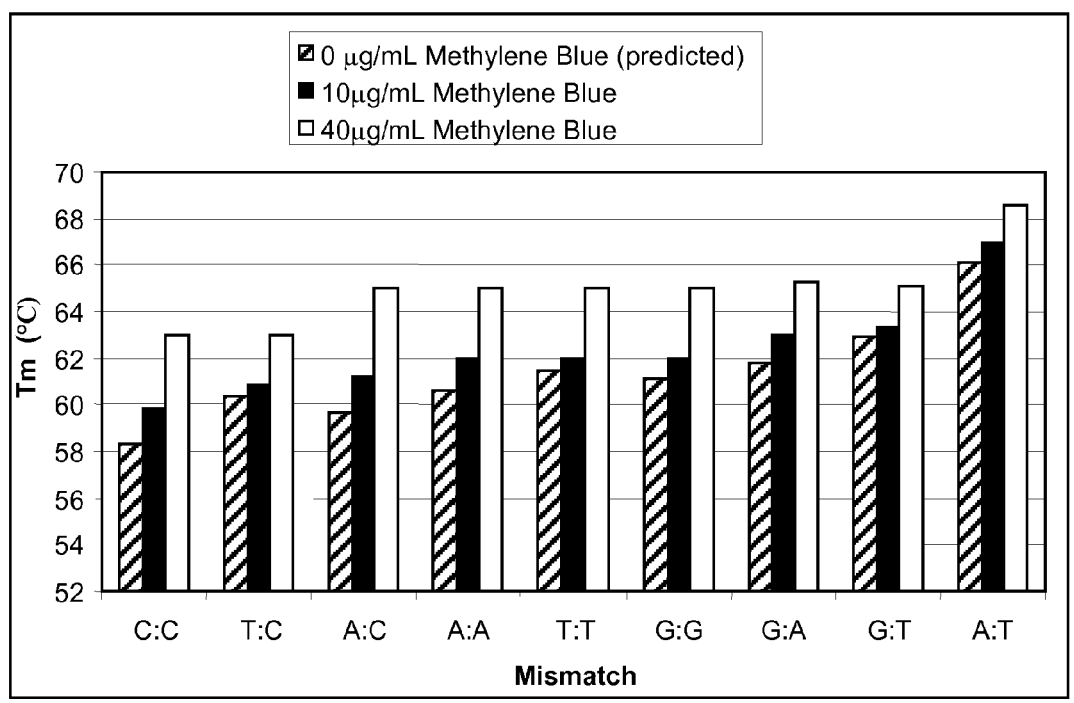

FIG. 61 provides a bar graph summary of Tm determinations using the HCV probe provided in FIG. 52A and engineered synthetic templates that contain single base mismatches in various mismatch combinations. The Tm determinations were made using two different concentrations of methylene blue soluble quencher, as indicated. Also shown in the bar graph are the predicted Tm values of the various duplexes (in the absence of methylene blue) generated by Visual OMP software (DNA Software, Inc., Ann Arbor, Mich.).

FIG. 62 provides nucleotide sequences corresponding to or derived from the HIV genome that find use with the invention. The sequences include the SK145 forward HIV amplification primer region, the reverse complement of the GAG152 reverse amplification primer region, and the reverse complement of the HIV GAG108FBHQ29I 5'-nuclease quantitation probe region. Beneath these sequences are the corresponding homologous domains from known HIV subtype isolates. Variable positions are indicated.

Figure 63:
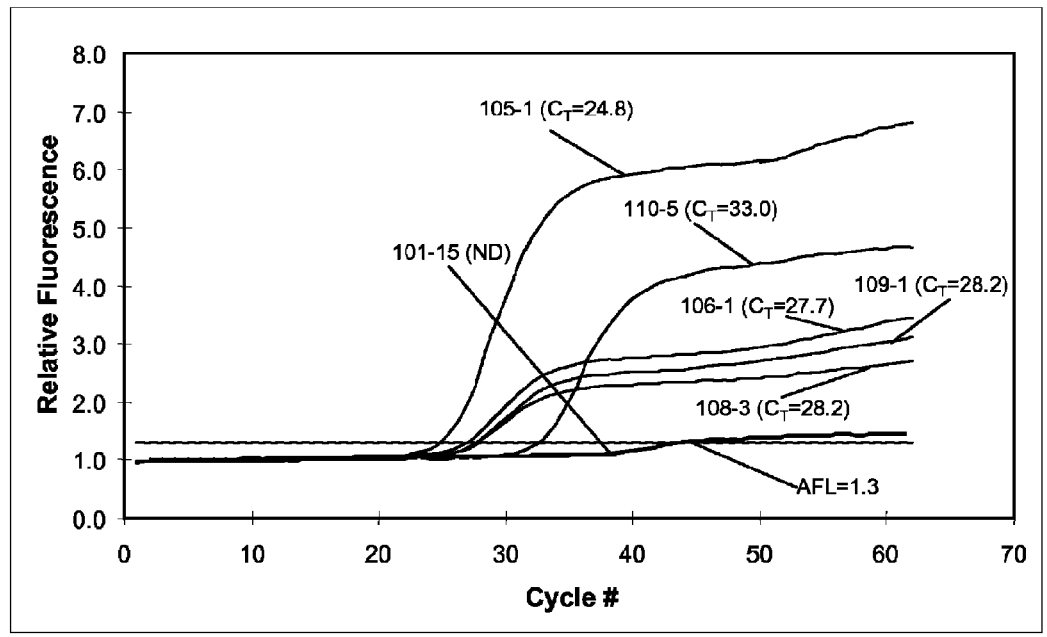

FIG. 63 provides a graph with the results of HIV RNA amplification (RT-PCR) quantitation using the SK145BU and GAG152BU amplification primers and the GAG108FBHQ29I 5'-nuclease quantitation probe. Various HIV RNA templates (106 copies each) are used in the amplification reactions, as shown. No thiazine dye is present in the reactions. The results of each genotype analysis are overlaid on the same graph. A representative set of data is shown. The $C_T$ number for the various HIV genotypes tested is provided.

Figure 64:
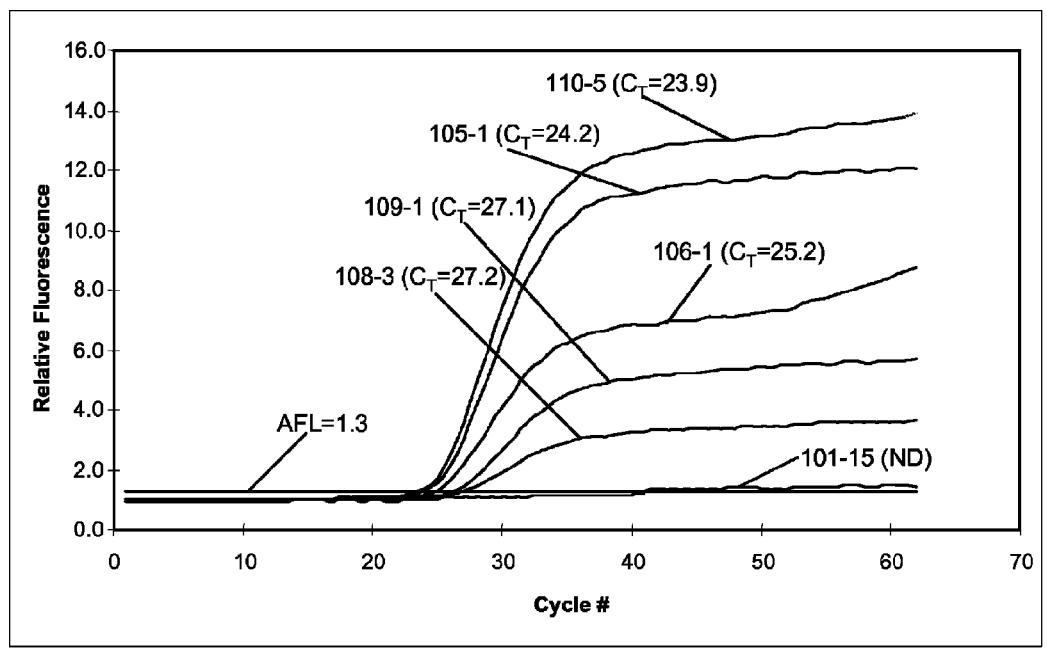

FIG. 64 provides a graph with the results of an HIV RNA amplification quantitation analysis identical to that described in FIG. 63, except that each of the reactions also contains 50 µg/mL of new methylene blue.

Figure 65:
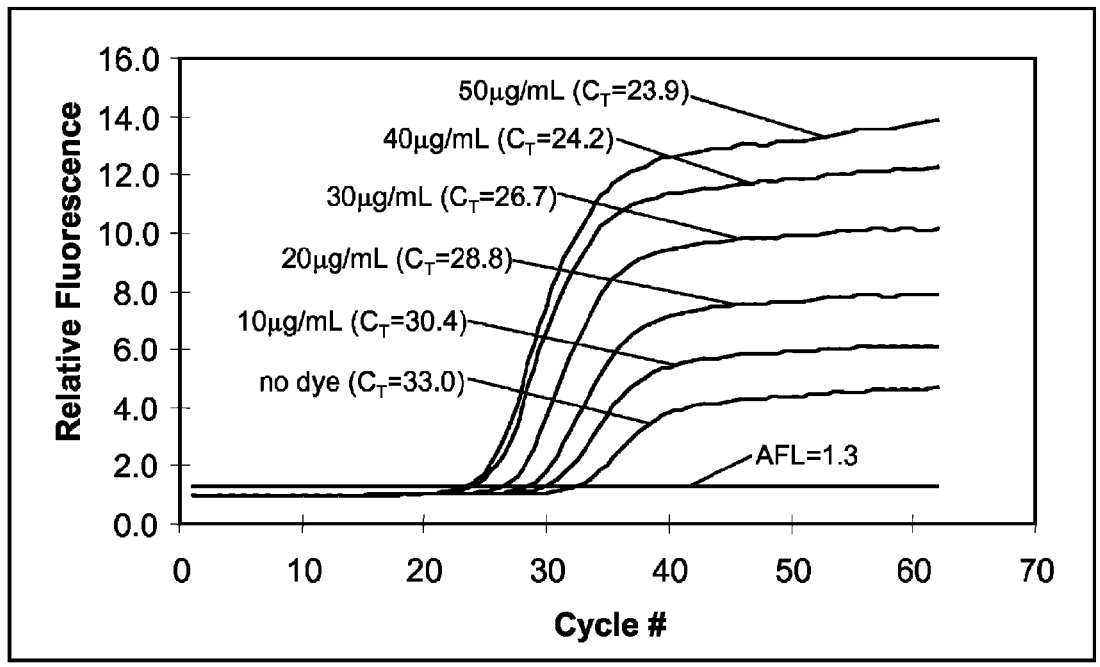

FIG. 65 provides a graph with the results of HIV RNA amplification (RT-PCR) quantitation using the SK145BU and GAG152BU amplification primers and the GAG108FBHQ29I 5'-nuclease quantitation probe. An RNA template corresponding to HIV genotype 110-5 is used in the amplification reaction ($10^6$ copies). This genotype results in a total of six mismatches under the forward primer and one mismatch under the 5'-nuclease quantitation probe. Increasing concentrations of new methylene blue are used in the reactions. The results of each analysis are overlaid on the same graph. A representative set of data is shown. The $C_T$ number for each of the various amplification reactions is provided.

Figure 66:
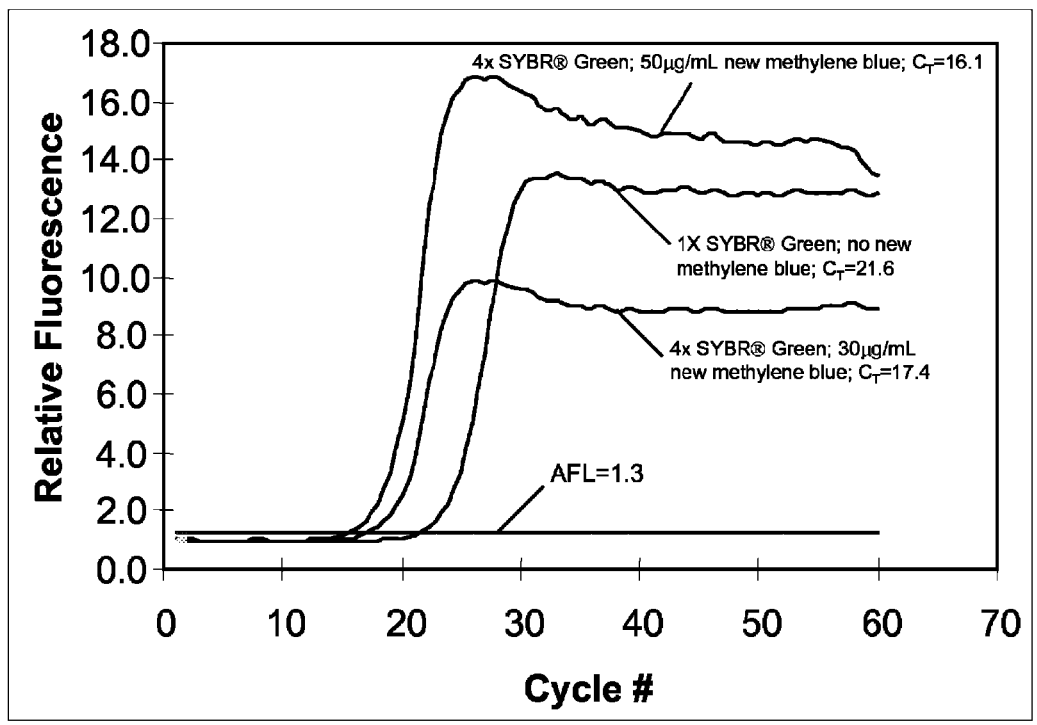

FIG. 66 provides a graph with the results of HIV RNA amplification (RT-PCR) quantitation using the SK145BU and GAG152BU amplification primers. An RNA template corresponding to HIV genotype 110-5 is used in the amplification reaction ($10^6$ copies). Amplicon detection and quantitation is made by the addition of SYBR® Green to the reaction. Different concentrations of Molecular Probes SYBR® Green (1× which is a 1:10,000 dilution of the stock SYBR® dye solution, and 4× which is a 1:2500 dilution of the stock dye solution) and new methylene blue (0-50 µg/mL) are used in the reactions. The results of each analysis are overlaid on the same graph. A representative set of data is shown. The $C_T$ number observed for each reaction is indicated.

DETAILED DESCRIPTION

Introduction

The present invention provides simple and robust methods and other aspects related to the modulation of light emissions from labeled nucleic acids. To illustrate, labeled nucleic acids, such as 5'-nuclease probes, molecular beacons, SCORPIONS primers, fluorescence resonance energy transfer (FRET) probes, etc. are commonly used to detect nucleic acids in various applications, including genotyping, diagnostics, forensics, among many others well known to those of skill in the art. Many of these probes include light-emitting labeling moieties, such as fluorescent reporter dyes, and quencher moieties that reduce the detectable emission of light from the light-emitting moieties when the two moieties are in suitable proximity to one another. Although these quencher moieties reduce detectable light emissions, this reduction is often incomplete. That is, these multiply labeled probes frequently have an associated residual or baseline emission of light. As the amount of probe is increased in a reaction mixture, whether due to the use of multiple sets of different probes in multiplexing applications, or higher amounts of a given probe in essentially any application, this baseline light emission also tends to increase. Baseline light emissions such as these typically negatively impact the performance of assays involving these probes by, e.g., limiting the sensitivity (i.e., the ability of the assay to discriminate between small differences in analyte concentration) and dynamic range (i.e., the useful range of the assay which extends from the lowest concentration at which quantitative measurements can be made (limit of quantitation, or LOQ) to the concentration at which the calibration curve departs from linearity (limit of linearity, LOL) of detection). Thus, certain light emission modifiers described herein are used to further reduce, if not eliminate, these baseline light emissions in some embodiments, to improve the performance of assays involving these types of labeled probes.

In addition to providing approaches to modulating light emissions from probes that comprise multiple labels, such as those having pairs of reporter and quencher moieties, the invention also provides for the modulation of light emissions from probes that each include only a single light-emitting moiety. These approaches can also be used to effect the real-time detection of target nucleic acids, including real-time reverse transcription-polymerase chain reaction-based (kinetic RT-PCR) assays with signal dynamic ranges that are suitable for highly sensitive detection. Similar to other multiplexing approaches described herein, in certain embodiments a single type of light emission modifier can be used to quench multiple single-labeled probes that have different light-emitting moieties in the same reaction mixture to effect the simultaneous detection of multiple target nucleic acids. Moreover, single-labeled probes are typically easier to synthesize and less costly to produce than multi-labeled probes.

In overview, the invention provides reaction mixtures that include light-emitting labeled oligonucleotides (e.g., 5'-nuclease probes, etc.) and light emission modifiers (e.g., soluble light emission modifiers) that modify the emission of light from the oligonucleotides. Exemplary light emission modifiers include a variety of diazine and thiazine dyes. In certain embodiments, these reaction mixtures, or components thereof, are included in kits. Methods of modifying the emission of light from labeled oligonucleotides, e.g., as part of nucleic acid amplification assays in which target nucleic acids are detected in real-time are also provided. In addition, systems for detecting light emitted from the labeled oligonucleotides in the reaction mixtures described herein are also provided. These and a variety of other aspects and features of the present invention will be apparent upon a complete review of this disclosure.

Figure 1A:
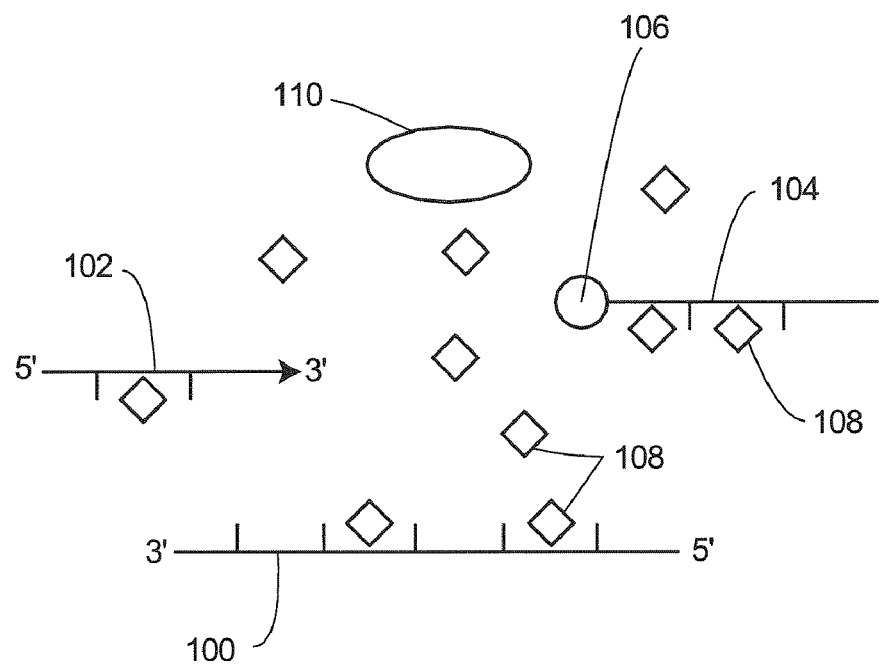
FIGS. 1A and B schematically illustrate an assay that includes light emission modifiers according to one embodiment of the invention.
Figure 1B:
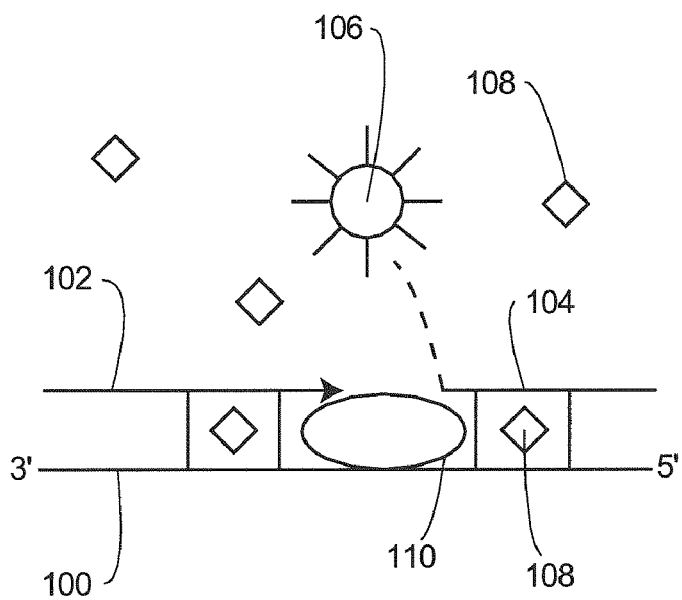

To illustrate, FIGS. 1A and B schematically show an assay in which light emission modifiers are used to substantially quench light emissions from a 5'-nuclease probe that is labeled with a single light-emitting moiety (e.g., a fluorescent dye, etc.). As shown in FIG. 1A, a reaction mixture includes target nucleic acid 100, primer 102, probe 104, and polymerase 110 (having a 5' to 3' nuclease activity). Fluorophore 106 is covalently attached at or near a 5' terminus of probe 104. As further shown, the reaction mixture also includes light emission modifier 108, which non-covalently associates with target nucleic acid 100 and primer 102. Light emission modifier 108 also non-covalently associates with probe 104 to substantially quench fluorescence emitted from probe 104. As shown in FIG. 1B, as the assay proceeds, polymerase 110 cleaves fragments from probe 104, which is bound to target nucleic acid 100. In this process, a fragment that comprises fluorophore 106 is released from the remaining portion of probe 104. As a consequence, a detectable increase in fluorescence results, since the fluorescence emitted by fluorophore 106 from the fragment is less quenched than from probe 104 prior to cleavage. That is, the light emission modifiers described herein typically quench or reduce light emissions from labeled nucleic acids in a length dependent manner.

Figure 2A:
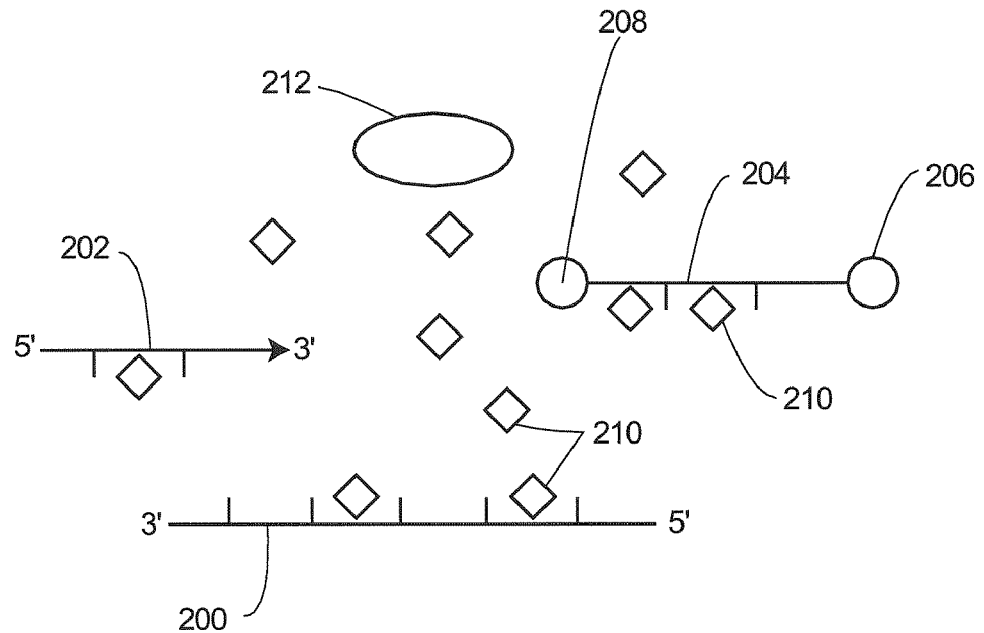
FIGS. 2A and B schematically illustrate another assay that includes light emission modifiers according to one embodiment of the invention.
Figure 2B:
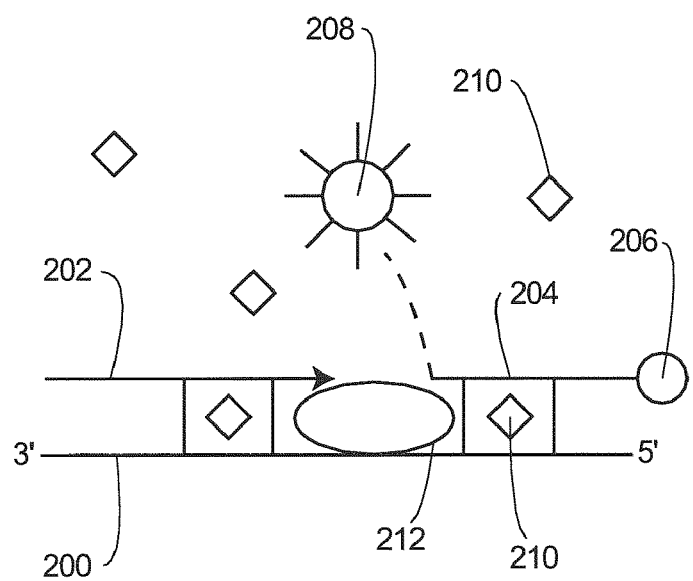

To further illustrate, FIGS. 2 A and B schematically depict an assay in which light emission modifiers are used to reduce baseline light emissions from a dual labeled 5'-nuclease probe. As shown in FIG. 2A, a reaction mixture includes target nucleic acid 200, primer 202, probe 204, and polymerase 212 (having a 5' to 3' nuclease activity). Fluorophore 208 is covalently attached at a 5' terminus of probe 204 and quencher 206 is covalently attached at a 3' terminus of probe 204. Although not shown here, fluorophore 208 or quencher 206 may optionally be attached to internal residues of probe 204. As further shown, the reaction mixture also includes light emission modifier 210, which non-covalently associates with target nucleic acid 200 and primer 202. Light emission modifier 210 also non-covalently associates with probe 204 to reduce baseline fluorescence emitted from probe 204. As shown in FIG. 2B, as the assay proceeds, polymerase 212 cleaves fragments from probe 204, which is bound to target nucleic acid 200. Similar to the process described above with respect to FIGS. 1A and B, a fragment that comprises fluorophore 208 is released and a detectable increase in fluorescence results.

Reaction Mixtures

The reaction mixtures of the invention can be used in a wide variety of applications where it is desirable to modify the emission of light from labeled nucleic acids. In some embodiments, for example, the reaction mixtures described herein are utilized in performing homogeneous amplification/detection assays (e.g., real-time PCR, etc.), particularly in multiplex formats in which multiple labeled probes are pooled together. Certain of the light emission modifiers described herein reduce the baseline emission of light from labeled probes under the varied temperature and other reaction conditions typically used in these types of assays unlike many previously known compounds. In addition to light emission modifiers and labeled oligonucleotides, other reagents that are optionally included in the reaction mixtures of the invention are described in greater detail below.

Light Emission Modifiers

The light emission modifiers used in the reaction mixtures and other aspects of the invention typically include a variety of properties that make them well suited to modulate or modify emissions of light from labeled probes in various types of nucleic acid amplification reactions and assays. To illustrate, these light emission modifiers typically bind to both single-stranded nucleic acids (e.g., single-stranded probes) and to double-stranded nucleic acids (e.g., single-stranded probes hybridized to target nucleic acids). Further, without being bound by any particular theory, it is believed that the light emission modifiers described herein generally bind to nucleic acids and modify light emission from labels associated with the nucleic acids in a length dependent manner. That is, the extent that a light emission modifier modifies the emission of light from a given labeled oligonucleotide is typically proportional to the length of that oligonucleotide. For example, a particular light emission modifier will generally modify the emission of light from labeled fragments of the oligonucleotide to a lesser extent than from the intact or full-length oligonucleotide, e.g., prior to cleavage in a 5'-nuclease reaction. A given light emission modifier is also typically able to effectively modify the emission of light from a variety of different light-emitting moieties. In other words, the modifications (e.g., quenching) effected by these light emission modifiers are generally spectral overlap independent or universal and without being bound to any particular theory of operation, likely occur by way of ground state complex formation. This is an important property, for example, in multiplexing assays in which multiple probes labeled with different fluorophores or other labeling moieties are commonly utilized.

To further illustrate, the light emission modifiers of the invention generally remain bound to, and modify light emissions from, e.g., full-length probes at temperatures commonly used in, e.g., kinetic PCR monitoring (e.g., annealing temperatures of between about 35° C. to about 60° C., extension temperatures of between about 65° C. to about 80° C., anneal-extend step temperatures of between about 35° C. to about 80° C. for two-step PCRs, etc.). Suitable PCR reaction conditions are also described below and in, e.g., Gelfand et al. (Eds.), *PCR Applications: Protocols for Functional Genomics*, Elsevier Science & Technology Books (1999), which is incorporated by reference. Moreover, the light emission modifiers of the invention have the ability to bind to, and modify light emissions from, full-length probes in reaction mixtures that include various other PCR components, such as buffers, salts, metal ions, primers, dNTPs, ddNTPs or other terminator nucleotides, glycerol, DMSO, poly rA, and the like. The light emission modifiers described herein also generally do not appreciably interfere with any of the steps used in PCR (e.g., annealing, extension, denaturing). In RT-PCR applications, the light emission modifiers described herein also typically do not significantly inhibit reverse transcription steps. An additional advantage of these light emission modifiers is that they continue to modify the emission of light from full-length probes even in the presence of large amounts of accumulating amplicons with little partitioning to these PCR products. To further exemplify, the light emission modifiers described herein also do not have sufficient, if any, intrinsic fluorescence in certain regions of visible spectrum that might otherwise interfere with or bias assay detection. Many of these attributes are also illustrated in the examples provided below or otherwise referred to herein.

Many different light emission modifiers are suitable for use in the reaction mixtures and other aspects of the invention. Typically, light emission modifiers are soluble nucleic acid binding compounds that are capable of modifying the emission of light from labeled oligonucleotides, such as 5'-nuclease probes, molecular beacons, or the like, at reaction temperatures commonly used in performing real-time PCR reaction steps, such as at annealing temperatures of at least about 40° C., etc. In some embodiments, for example, the light emission modifiers of the invention include various diazine and thiazine dyes. Exemplary diazine dyes that can be used as light emission modifiers include, e.g., azocarmine dyes (e.g., azocarmine A, azocarmine B ($C_{28}H_{17}N_3O_9S_3Na_2$), azocarmine G ($C_{28}H_{18}N_3O_6S_2Na$), etc.), phenazine dyes, diethylsafraninazodimethylaniline chloride (i.e., Janus Green B or Diazine Green 5 ($C_{30}H_{31}N_6Cl$)), and the like. The chemical structures of some of these diazine dyes are presented in Table I.

To further illustrate, exemplary thiazine dyes that can be used as light emission modifiers include, e.g., methylene blue ($C_{16}H_{18}ClN_3S$), methylene green ($C_{16}H_{17}ClN_4O_2S$), thionin ($C_{12}H_{10}ClN_3S$), sym-dimethylthionin, toluidine blue O ($C_{15}H_{16}N_3SCl$), new methylene blue ($C_{18}H_{22}ClN_3S$), methylene violet bernthsen, azure A ($C_{14}H_{14}ClN_3S$), azure B ($C_{15}H_{16}ClN_3S$), azure C($C_{13}H_{12}ClN_3S$), and the like. The chemical structures of some of these thiazine dyes are presented in Table II.

TABLE I

AZOCARMINE G

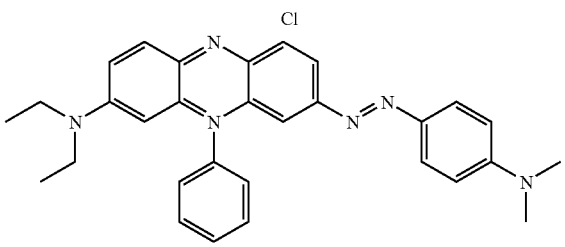

CELESTINE BLUE

JANUS GREEN B

TABLE II

THIONIN

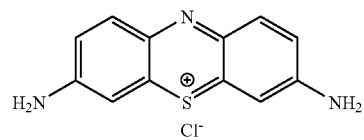

AZURE C

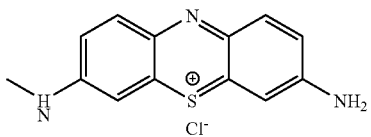

AZURE A

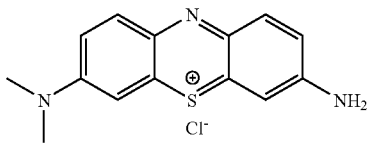

AZURE B

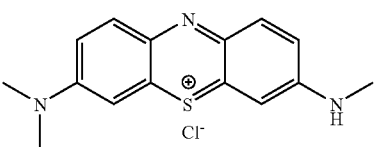

SYM-DIMETHYLTHIONIN

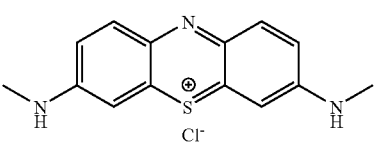

METHYLENE VIOLET BERNTHSEN

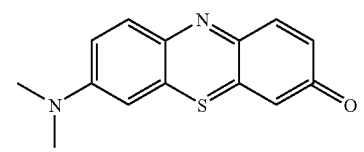

TABLE II-continued

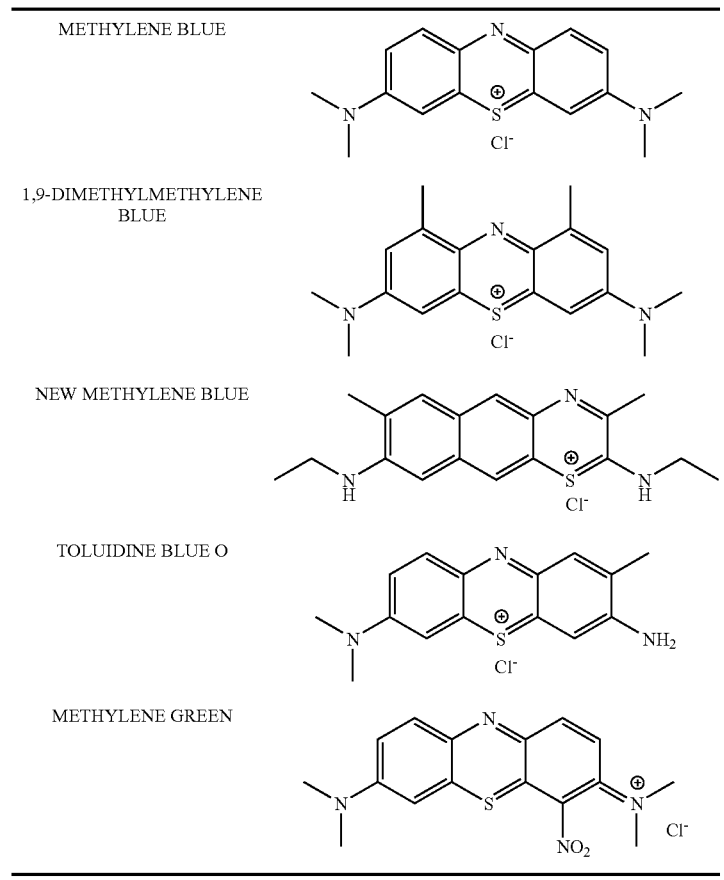

The amount of the particular light emission modifier included in a given reaction mixture typically depends on the extent of modification sought. Typically, the extent of light emission modification is proportional to the amount of light emission modifier present in a reaction mixture. Although other quantities are optionally utilized, light emission modifiers are typically present at between about 5 μg/mL of the reaction mixture and about 100 μg/mL of the reaction mixture, more typically at between about 10 μg/mL of the reaction mixture and about 75 μg/mL of the reaction mixture, and still more typically at between about 15 μg/mL of the reaction mixture and about 50 μg/mL of the reaction mixture (e.g., about 20 μg/mL, about 30 μg/mL, about 40 μg/mL, etc.). In some embodiments, reaction mixtures include light emission modifier concentrations that are in excess of amplicon concentrations. The effects of various light emission modifier concentrations in reaction mixtures are further illustrated in the examples provided below. In some embodiments, more than one light emission modifier can be used in the same reaction mixture. In these embodiments, the different light emission modifiers are optionally present at the same or at different concentrations in the particular reaction mixture. As one example, a reaction mixture may include 20 μg of new methylene blue per mL of the reaction mixture and 30 μg of methylene blue per mL of the reaction mixture. Light emission modifiers are readily available from various commercial suppliers including, e.g., Sigma-Aldrich Corp. (St. Louis, Mo., USA).

Labeled Oligonucleotides

The reaction mixtures of the invention include labeled oligonucleotides in addition to light emission modifiers. Various approaches can be utilized by one of skill in the art to design oligonucleotides for use as probes (e.g., 5'-nuclease probes, molecular beacons, FRET probes, etc.) and/or primers. To illustrate, the DNAstar software package available from DNASTAR, Inc. (Madison, Wis., U.S.A.) can be used for sequence alignments. For example, target nucleic acid sequences and non-target nucleic acid sequences can be uploaded into DNAstar EditSeq program as individual files, e.g., as part of a process to identify regions in these sequences that have low sequence similarity. To further illustrate, pairs of sequence files can be opened in the DNAstar MegAlign sequence alignment program and the Clustal W method of alignment can be applied. The parameters used for Clustal W alignments are optionally the default settings in the software. MegAlign typically does not provide a summary of the percent identity between two sequences. This is generally calculated manually. From the alignments, regions having, e.g., less than a selected percent identity with one another are typically identified and oligonucleotide sequences in these regions can be selected. Many other sequence alignment algorithms and software packages are also optionally utilized. Sequence alignment algorithms are also described in, e.g., Notredame et al. (2000) "T-coffee: a novel method for fast and accurate multiple sequence alignment," *J. Mol. Biol.* 302:205-217, Edgar (2004) "MUSCLE: a multiple sequence alignment method with reduced time and space complexity," *BMC Bioinformatics* 5:113, Mount, *Bioinformatics: Sequence and Genome Analysis*, Cold Spring Harbor Laboratory Press (2001), and Durbin et al., *Biological Sequence Analysis: Probabilistic Models of Proteins and Nucleic Acids*, Cambridge University Press (1998), which are each incorporated by reference.

To further illustrate, optimal alignment of sequences for comparison can be conducted, e.g., by the local homology algorithm of Smith & Waterman (1981) *Adv. Appl. Math.* 2:482, by the homology alignment algorithm of Needleman & Wunsch (1970) *J. Mol. Biol.* 48:443, by the search for similarity method of Pearson & Lipman (1988) *Proc. Nat'l. Acad. Sci. USA* 85:2444, which are each incorporated by reference, and by computerized implementations of these algorithms (e.g., GAP, BESTFIT, FASTA, and TFASTA in the Wisconsin Genetics Software Package, Genetics Computer Group (Madison, Wis., U.S.A.)), or by even by visual inspection.

Another example algorithm that is suitable for determining percent sequence identity is the BLAST algorithm, which is described in, e.g., Altschul et al. (1990) *J. Mol. Biol.* 215:403-410, which is incorporated by reference. Software for performing versions of BLAST analyses is publicly available through the National Center for Biotechnology Information on the world wide web at ncbi.nlm.nih.gov/ as of Jun. 30, 2005.

An additional example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) *J. Mol. Evol.* 35:351-360, which is incorporated by reference.

Oligonucleotide probes and primers are optionally prepared using essentially any technique known in the art. In certain embodiments, for example, the oligonucleotide probes and primers are synthesized chemically using essentially any nucleic acid synthesis method, including, e.g., the solid phase phosphoramidite method described by Beaucage and Caruthers (1981) *Tetrahedron Letts.* 22(20):1859-1862, which is incorporated by reference. To further illustrate, oligonucleotides can also be synthesized using a triester method (see, e.g., Capaldi et al. (2000) "Highly efficient solid phase synthesis of oligonucleotide analogs containing phosphorodithioate linkages" *Nucleic Acids Res.* 28(9):e40 and Eldrup et al. (1994) "Preparation of oligodeoxyribonucleoside phosphorodithioates by a triester method" *Nucleic Acids Res.* 22(10):1797-1804, which are both incorporated by reference). Other synthesis techniques known in the art can also be utilized, including, e.g., using an automated synthesizer, as described in Needham-VanDevanter et al. (1984) *Nucleic Acids Res.* 12:6159-6168, which is incorporated by reference. A wide variety of equipment is commercially available for automated oligonucleotide synthesis. Multi-nucleotide synthesis approaches (e.g., tri-nucleotide synthesis, etc.) are also optionally utilized. Moreover, the primer nucleic acids optionally include various modifications. In certain embodiments, for example, primers include restriction site linkers, e.g., to facilitate subsequent amplicon cloning or the like. To further illustrate, primers are also optionally modified to improve the specificity of amplification reactions as described in, e.g., U.S. Pat. No. 6,001,611, entitled "MODIFIED NUCLEIC ACID AMPLIFICATION PRIMERS," issued Dec. 14, 1999 to Will, which is incorporated by reference. Primers and probes can also be synthesized with various other modifications (e.g., restriction sites, enzyme binding sites, etc.) as described herein or as otherwise known in the art.

Probes and/or primers utilized in the reaction mixtures, methods, and other aspects of the invention are typically labeled to permit detection of probe-target hybridization duplexes. In general, a label can be any moiety that can be attached to a nucleic acid and provide a detectable signal (e.g., a quantifiable signal). Labels may be attached to oligonucleotides directly or indirectly by a variety of techniques known in the art. To illustrate, depending on the type of label used, the label can be attached to a terminal (5' or 3' end of an oligonucleotide primer and/or probe) or a non-terminal nucleotide, and can be attached indirectly through linkers or spacer arms of various sizes and compositions. Using commercially available phosphoramidite reagents, one can produce oligonucleotides containing functional groups (e.g., thiols or primary amines) at either the 5' or 3' terminus via an appropriately protected phosphoramidite, and can label such oligonucleotides using protocols described in, e.g., Innis et al. (Eds.) *PCR Protocols: A Guide to Methods and Applications*, Elsevier Science & Technology Books (1990)(Innis), which is incorporated by reference.

Essentially any labeling moiety is optionally utilized to label a probe and/or primer by techniques well known in the art. In some embodiments, for example, labels comprise a fluorescent dye (e.g., a rhodamine dye (e.g., R6G, R110, TAMRA, ROX, etc.), a fluorescein dye (e.g., JOE, VIC, TET, HEX, FAM, etc.), a halofluorescein dye, a cyanine dye (e.g., CY3, CY3.5, CY5, CY5.5, etc.), a BODIPY® dye (e.g., FL, 530/550, TR, TMR, etc.), an ALEXA FLUOR® dye (e.g., 488, 532, 546, 568, 594, 555, 653, 647, 660, 680, etc.), a dichlororhodamine dye, an energy transfer dye (e.g., BIGDYE™ v 1 dyes, BIGDYE™ v 2 dyes, BIGDYE™ v 3 dyes, etc.), Lucifer dyes (e.g., Lucifer yellow, etc.), CASCADE BLUE®, Oregon Green, and the like. Additional examples of fluorescent dyes are provided in, e.g., Haugland, *Molecular Probes Handbook of Fluorescent Probes and Research Products*, Ninth Ed. (2003) and the updates thereto, which are each incorporated by reference. Fluorescent dyes are generally readily available from various commercial suppliers including, e.g., Molecular Probes, Inc. (Eugene, Oreg.), Armersham Biosciences Corp. (Piscataway, N.J.), Applied Biosystems (Foster City, Calif.), etc. Other labels include, e.g., biotin, weakly fluorescent labels (Yin et al. (2003) *Appl Environ Microbiol.* 69(7):3938, Babendure et al. (2003) *Anal. Biochem.* 317(1):1, and Jankowiak et al. (2003) *Chem Res Toxicol.* 16(3):304), non-fluorescent labels, colorimetric labels, chemiluminescent labels (Wilson et al. (2003) *Analyst.* 128 (5):480 and Roda et al. (2003) *Luminescence* 18(2):72), Raman labels, electrochemical labels, bioluminescent labels (Kitayama et al. (2003) *Photochem Photobiol.* 77(3):333, Arakawa et al. (2003) *Anal. Biochem.* 314(2):206, and Maeda (2003) *J. Pharm. Biomed. Anal.* 30(6): 1725), and an alpha-methyl-PEG labeling reagent as described in, e.g., U.S. Provisional Patent Application No. 60/428,484, filed on Nov. 22, 2002, which references are each incorporated by reference. Nucleic acid labeling is also described further below.

In addition, whether a fluorescent dye is a donor or an acceptor is generally defined by its excitation and emission spectra, and the fluorescent dye with which it is paired. Fluorescent molecules commonly used as quencher moieties in probes and primers include, e.g., fluorescein, FAM, JOE, rhodamine, R6G, TAMRA, ROX, DABCYL, and EDANS. Many of these compounds are available from the commercial suppliers referred to above. Exemplary non-fluorescent or dark quenchers that dissipate energy absorbed from a fluorescent dye include the Black Hole Quenchers™ or BHQ™, which are commercially available from Biosearch Technologies, Inc. (Novato, Calif., USA).

To further illustrate, essentially any nucleic acid (and virtually any labeled nucleic acid, whether standard or non-standard) can be custom or standard ordered from any of a variety of commercial sources, such as The Midland Certified Reagent Company, The Great American Gene Company, ExpressGen Inc., Operon Technologies Inc., Proligo LLC, and many others.

In certain embodiments, modified nucleotides are included in probes and primers. To illustrate, the introduction of modified nucleotide substitutions into oligonucleotide sequences can, e.g., increase the melting temperature of the oligonucleotides. In some embodiments, this can yield greater sensitivity relative to corresponding unmodified oligonucleotides even in the presence of one or more mismatches in sequence between the target nucleic acid and the particular oligonucleotide. Exemplary modified nucleotides that can be substituted or added in oligonucleotides include, e.g., C5-ethyl-dC, C5-ethyl-dU, 2,6-diaminopurines, C5-propynyl-dC, C7-propynyl-dA, C7-propynyl-dG, C5-propargylamino-dC, C5-propargylamino-dU, C7-propargylamino-dA, C7-propargylamino-dG, 7-deaza-2-deoxyxanthosine, pyrazolopyrimidine analogs, pseudo-dU, nitro pyrrole, nitro indole, 2'-0-methyl Ribo-U, 2'-0-methyl Ribo-C, an 8-aza-dA, an 8-aza-dG, a 7-deaza-dA, a 7-deaza-dG, N4-ethyl-dC, N6-methyl-dA, etc. To further illustrate, other examples of modified oligonucleotides include those having one or more LNA™ monomers. Nucleotide analogs such as these are also described in, e.g., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference. Oligonucleotides comprising LNA™ monomers are commercially available through, e.g., Exiqon A/S (Vedbaek, DK). Additional oligonucleotide modifications are referred to herein, including in the definitions provided above.

Labeled oligonucleotides, such as 5'-nuclease probes, hybridization probes, SCORPION® primers, and molecular beacons are described further herein.

Nucleic Acid Amplification Reagents

The reaction mixtures of the invention typically include selected amounts of light emission modifiers and labeled oligonucleotides, as described herein. In addition, reaction mixtures also generally include various reagents that are useful in performing nucleic acid amplification or detection reactions, such as real-time PCR monitoring or 5'-nuclease assays. Exemplary nucleic acid amplification reagents include, e.g., primer nucleic acids, template or target nucleic acids, nucleotide incorporating biocatalysts (e.g., DNA polymerases, etc.), extendible nucleotides, terminator nucleotides, buffers, salts, amplicons, glycerol, metal ions, dimethyl sulfoxide (DMSO), poly rA (a carrier nucleic acid for low copy targets), and the like. In some embodiments, for example, nucleic acid amplification reactions are performed utilizing these reaction mixtures to effect the detection of target nucleic acids in samples, e.g., to aid in the diagnosis and/or prognosis of diseases. Nucleic acid amplification and detection methods are also described further below.

Reaction mixtures are generally produced by combining selected light emission modifiers and labeled oligonucleotides with quantities of the nucleic acid amplification reagents that are sufficient for performing the particular nucleic acid amplification method selected. The quantities of nucleic acid amplification reagents to be included in a given reaction mixture are well-known to persons of skill in the art in view of the selected nucleic acid amplification method. To illustrate, however, primer nucleic acids and extendible nucleotides (e.g., four dNTPs (dGTP, dCTP, dATP, dTTP)) are each present in a large molar excess in the reaction mixtures in certain embodiments. Probe and primer nucleic acids that can be utilized in the reaction mixtures of the invention are described herein. Suitable extendible nucleotides are readily available from many different commercial suppliers including, e.g., Roche Diagnostics Corporation (Indianapolis, Ind., USA), Amersham Biosciences Corp. (Piscataway, N.J., USA), Applied Biosystems (Foster City, Calif., USA), and the like.

The nucleotide incorporating biocatalysts utilized in the reaction mixtures and other aspect of the invention typically comprise enzymes, such as polymerases, terminal transferases, reverse transcriptases, telomerases, polynucleotide phosphorylases, and the like. In certain embodiments, for example, the enzyme includes a 5'-3' nuclease activity, a 3'-5' exonuclease activity, and/or is a thermostable enzyme. The enzyme is optionally derived from an organism, such as *Thermus antranikianii, Thermus aquaticus, Thermus caldophilus, Thermus chliarophilus, Thermusfiliformis, Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Anaerocellum thermophilum, Bacillus caldotenax, Bacillus stearothermophilus*, or the like.

In certain embodiments, additional reagents are also added to the reaction mixtures of the invention. To illustrate, reaction mixtures also optionally include pyrophosphatases (e.g., a thermostable pyrophosphatase), e.g., for use in minimizing pyrophosphorolysis, dUTP and uracil N-glycosylase (UNG) (e.g., a thermostable UNG), e.g., to protect against carry-over contamination, and the like.

Methods of Modifying Light Emissions from Labeled Oligonucleotides

The invention also provides methods of modifying light emissions (e.g., baseline light emissions) from labeled oligonucleotides. Typically, these methods are performed as part of assays that involve the detection of target nucleic acids, e.g., to provide diagnostic, genetic, or other information about subjects from which the target nucleic acids were derived. In some embodiments, the light emission modifiers used in these methods reduce the emission of light from labeled oligonucleotides. This generally improves performance characteristics, such as the sensitivity and dynamic range of the particular assay (e.g., a real-time PCR technique) in which the light emission modifiers described herein are utilized. These aspects are also illustrated in the examples provided below.

In practicing the methods of the present invention, many conventional techniques in molecular biology are optionally utilized. These techniques are well known and are explained in, for example, Ausubel et al. (Eds.) *Current Protocols in Molecular Biology*, Volumes I, II, and III, (1997) (Ausubel 1), Ausubel et al. (Eds.), *Short Protocols in Molecular Biology: A Compendium of Methods from Current Protocols in Molecular Biology*, 5$^{th}$ Ed., John Wiley & Sons, Inc. (2002) (Ausubel 2), Sambrook et al., *Molecular Cloning: A Laboratory Manual*, 3rd Ed., Cold Spring Harbor Laboratory Press (2000) (Sambrook), Berger and Kimmel, *Guide to Molecular Cloning Techniques: Methods in Enzymology*, Volume 152, Academic Press, Inc. (Berger), Vorbruggen et al., *Handbook of Nucleoside Synthesis*, Organic Reactions Series, #60, John Wiley & Sons, Inc. (2001), Gait (Ed.) Oligonucleotide Synthesis, Oxford University Press (1984), Hames and Higgins, *Nucleic Acid Hybridization*, Practical Approach Series, Oxford University Press (1997), and Hames and Higgins (Eds.) *Transcription and Translation*, Practical Approach Series, Oxford University Press (1984), all of which are incorporated by reference.

Examples of general types of nucleic acid analysis technologies that can be used or adapted for use to analyze target nucleic acids in or from the reactions mixtures of the invention include various nucleic acid amplification assays. A common characteristic among nucleic acid amplification assays is that they are typically designed to amplify nucleic acid sequences that are specific for the organism being detected. Nucleic acid amplification tests generally have greater sensitivity than other approaches to nucleic acid analysis. This sensitivity, which is further improved with the use of the light emission modifiers of the invention, is typically attributable to their ability to produce a positive signal from as little as a single copy of the target nucleic acid. Amplification methods that are optionally utilized or adapted to detect target nucleic acids include, e.g., various polymerase, ligase, or reverse-transcriptase mediated amplification methods, such as the polymerase chain reaction (PCR), the ligase chain reaction (LCR), reverse-transcription PCR(RT-PCR), NASBA, TMA, SDA and the like. Additional details regarding the use of these and other amplification methods and various approaches to sample preparation for these assays can be found in any of a variety of standard texts, including, e.g., Berger, Sambrook, Ausubel 1 and 2, and Innis, which are referred to above. Various commercial nucleic acid amplification assays that are optionally adapted for use with the light emission modifiers and methods of the invention generally differ in their amplification methods and their target nucleic acid sequences. Examples of these commercial tests include the AMPLICOR® and COBAS AMPLICOR® assays (Roche Diagnostics Corporation, Indianapolis, Ind., USA), which use polymerase chain reactions (PCR); the LCx® test (Abbott Laboratories, Abbott Park, Ill., USA), which uses ligase chain reactions (LCR); the BDProbeTec™ ET test (Becton, Dickinson and Company, Franklin Lakes, N.J., USA), which uses strand displacement amplification (SDA); the NucliSens EasyQ assay (bioMerieux, Durham, N.C.), which uses nucleic acid sequence-based amplification (NASBA); and the APTIMA™ assay (Gen-Probe, Inc., San Diego, Calif., USA), which uses transcription-mediated amplification (TMA). Nucleic acid amplification and detection is described further below.

In certain embodiments, for example, the light emission modifiers of the invention are utilized in various 5'-nuclease reactions to modify (e.g., reduce) light emissions from 5'-nuclease probes. Many 5'-nuclease assays are well known to those of skill in the art. Examples of such reactions are also described, for instance, in U.S. Pat. Nos. 5,210,015, 6,214, 979, 5,804,375, and 5,487,972, supra, which are each incorporated by reference.

To briefly illustrate, in a 5'-nuclease reaction, a target nucleic acid is contacted with a primer and a probe (e.g., 5'-nuclease probe, etc.) under conditions in which the primer and probe hybridize to a strand of the target nucleic acid. The target nucleic acid, primer and probe are also contacted with a selected amount of a light emission modifier and a nucleic acid polymerase having 5' to 3' nuclease activity. Nucleic acid polymerases possessing 5' to 3' nuclease activity can cleave the probe hybridized to the target nucleic acid downstream of the primer. The 3' end of the primer provides the initial binding site for the polymerase. The bound polymerase cleaves fragments from the probe upon encountering the 5' end of the probe.

The primer and probe can be designed such that they anneal in close proximity on the target nucleic acid such that binding of the nucleic acid polymerase to the 3' end of the primer puts it in contact with the 5' end of the probe in the absence of primer extension. The term "polymerization-independent cleavage" refers to this process. Alternatively, if the primer and probe anneal to more distantly spaced regions of the target nucleic acid, polymerization typically occurs before the nucleic acid polymerase encounters the 5' end of the probe. As the polymerization continues, the polymerase progressively cleaves fragments from the 5' end of the probe. This cleaving continues until the remainder of the probe has been destabilized to the extent that it dissociates from the template molecule. The term "polymerization-dependent cleavage" refers to this process.

One advantage of polymerization-independent cleavage lies in the elimination of the need for amplification of the nucleic acid. Provided the primer and probe are adjacently bound to the nucleic acid, sequential rounds of probe annealing and cleavage of fragments can occur. Thus, a sufficient amount of fragments can be generated, making detection possible in the absence of polymerization.

In either process, a sample is provided which is thought to contain the target nucleic acid. The target nucleic acid contained in the sample may be first reverse transcribed into cDNA, if necessary, and then denatured, using any suitable denaturing method, including physical, chemical, or enzymatic methods, which are known to those of skill in the art. An exemplary physical approach to effect strand separation involves heating the nucleic acid until it is completely (>99%) denatured. Typical heat denaturation involves temperatures ranging from about 85° C. to about 105° C., for periods of time ranging from about 1 to about 10 minutes. As an alternative to denaturation, the nucleic acid may exist in a single-stranded form in the sample, such as, for example, single stranded RNA or DNA viruses.

The denatured target nucleic acid strand is typically incubated with a primer, a probe, and the selected light emission modifier under hybridization conditions that permit the primer and probe to bind to the target nucleic acid strand and the light emission modifier to bind at least to the probe. In some embodiments, two primers can be used to amplify the target nucleic acid. The two primers are typically selected so that their relative positions along the target nucleic acid are such that an extension product synthesized from one primer, when the extension produce is separated from its template (complement), serves as a template for the extension of the other primer to yield a replicate strand of defined length. In multiplexing formats, multiple probes are typically used in a single reaction vessel to simultaneously detect multiple target nucleic acids.

Because the complementary strands are typically longer than either the probe or primer, the strands have more points of contact and thus a greater chance of binding to each other over a given period of time. Accordingly, a high molar excess of probe and primer is typically utilized to favor primer and probe annealing over template strand reannealing.

Primers are generally of sufficient length and complementarity so that they selectively bind to target nucleic acids under selected conditions to permit polymerization-independent cleavage or polymerization-dependent cleavage to proceed. The exact length and composition of the primer will depend on many factors, including temperature of the annealing reaction, source and composition of the primer, proximity of the probe annealing site to the primer annealing site, and ratio of primer:probe concentration. For example, depending on the complexity of the target sequence, the primer typically includes about 15-30 nucleotides, although it may contain more or fewer nucleotides.

The probe is generally annealed to its complementary target nucleic acid before the nucleic acid polymerase encounters that region of the target nucleic acid, thereby permitting the 5' to 3' nuclease activity of the enzyme to cleave fragments from the probe. To enhance the likelihood that the probe will anneal to the target nucleic acid before the polymerase reaches this region of hybridization, a variety of techniques may be utilized. For example, short primers generally require cooler temperature to form sufficiently stable hybrid complexes with the nucleic acid. Therefore, the probe can be designed to be longer than the primer so that the probe preferentially anneals to the target nucleic acid at higher temperatures relative to primer annealing. To further illustrate, primers and probes having differential thermal stability can also be utilized. For example, the nucleotide composition of the probe can be chosen to have greater G/C content and, consequently, greater thermal stability than the primer. Optionally, modified nucleotides may be incorporated into primers or probes to effect either greater or lesser thermal stability in comparison to primers or probes having only unmodified nucleotides. Exemplary modified nucleotides are described further above. The thermocycling parameters can also be varied to take advantage of the differential thermal stability of the probe and primer. For example, following a thermocycling denaturation step, an intermediate temperature may be introduced which permits probe binding but not primer binding. Thereafter, the temperature can be further reduced to permit primer annealing. To preferentially favor binding of the probe before the primer, a high molar excess of probe to primer concentration can also be used. Such probe concentrations are typically in the range of about 2 to about 20 times higher than the respective primer concentration, which is generally about $0.5-5\times10^{-7}$ M.

Template-dependent extension of primers is generally catalyzed by a nucleotide incorporating biocatalyst (e.g., a polymerase, etc.) in the presence of adequate amounts of the four deoxyribonucleoside triphosphates (dATP, dGTP, dCTP, and dTTP) or analogs in a reaction mixture that also includes light emission modifiers and appropriate salts, metal cations, and buffers. Reaction mixtures are described further above. Suitable nucleotide incorporating biocatalysts are enzymes known to catalyze primer and template-dependent DNA synthesis and possess the 5' to 3' nuclease activity. Exemplary DNA polymerases of this type include *E. coli* DNA polymerase I, Tth DNA polymerase, *Bacillus stearothermophilus* DNA polymerase, Taq DNA polymerase, *Thermus* sp. ZO5 DNA polymerase, *Thermatoga maritima* DNA polymerase, *Thermatoga neopolitana* DNA polymerase, and *Thermosipho africanus* DNA polymerase. The reaction conditions for catalyzing DNA synthesis with these DNA polymerases are well known in the art. Typically, the nucleotide incorporating biocatalyst efficiently cleaves the probe and releases labeled fragments so that a detectable signal is directly or indirectly generated.

The products of the synthesis are generally duplex molecules that include the template strands and the primer extension strands. Byproducts of this synthesis are probe fragments, which can include a mixture of mono-, di- and larger nucleotide fragments. Repeated cycles of denaturation, probe and primer annealing, and primer extension and probe cleavage result in the exponential accumulation of the region defined by the primers and the exponential generation of labeled fragments. Sufficient cycles are run to achieve a detectable amount of probe fragments, which is generally several orders of magnitude greater than background signal.

The use of light emission modifiers as described herein can effectively reduce the number of cycles run before a detectable signal is produced relative to assays that do not reduce these background signals.

In certain embodiments, PCR reactions are carried out as an automated process, which utilizes a thermostable enzyme. In this process the reaction mixture is cycled through a denaturing step, a probe and primer annealing step, and a synthesis step in which cleavage and displacement occur simultaneously with primer dependent template extension. In some embodiments, the methods described herein are performed using a system. Such systems are described in greater detail below. Optionally, thermal cyclers, such as those commercially available from, e.g., Applied Biosystems (Foster City, Calif., USA), which are designed for use with thermostable enzymes, may be utilized.

Thermostable polymerases are typically used in automated processes that effect the denaturation of double stranded extension products by exposing them to a elevated temperatures (e.g., about 95° C.) during the PCR cycle. For example, U.S. Pat. No. 4,889,818, entitled "PURIFIED THERMOSTABLE ENZYME," issued to Dec. 26, 1989 to Gelfand et al., which is incorporated by reference, discloses a representative thermostable enzyme isolated from *Thermus aquaticus*. Additional representative thermostable polymerases include, e.g., polymerases extracted from the thermostable bacteria *Thermus flavus*, *Thermus ruber*, *Thermus thermophilus*, *Bacillus stearothermophilus* (which has a somewhat lower temperature optimum than the others listed), *Thermus lacteus*, *Thermus rubens*, *Thermotoga maritima*, *Thermatoga neopolitana*, *Thermosipho africanus*, *Thermococcus littoralis*, and *Methanothermus fervidus*.

Hybridization of probes to target nucleic acids can be accomplished by choosing appropriate hybridization conditions. The stability of the probe:target nucleic acid hybrid is typically selected to be compatible with the assay and washing conditions so that stable, detectable hybrids form only between the probes and target nucleic acids. Manipulation of one or more of the different assay parameters determines the exact sensitivity and specificity of a particular hybridization assay.

More specifically, hybridization between complementary bases of DNA, RNA, PNA, or combinations of DNA, RNA and PNA, occurs under a wide variety of conditions that vary in temperature, salt concentration, electrostatic strength, buffer composition, and the like. Examples of these conditions and methods for applying them are described in, e.g., Tijssen, *Hybridization with Nucleic Acid Probes*, Vol. 24, Elsevier Science (1993), and Hames and Higgins, supra, which are both incorporated by reference. Hybridization generally takes place between about 0° C. and about 70° C., for periods of from about one minute to about one hour, depending on the nature of the sequence to be hybridized and its length. However, it is recognized that hybridizations can occur in seconds or hours, depending on the conditions of the reaction. To illustrate, typical hybridization conditions for a mixture of two 20-mers is to bring the mixture to 68° C., followed by cooling to room temperature (22° C.) for five minutes or at very low temperatures such as 2° C. in 2 microliters. Hybridization between nucleic acids may be facilitated using buffers such as Tris-EDTA (TE), Tris-HCl and HEPES, salt solutions (e.g. NaCl, KCl, $CaCl_2$), or other aqueous solutions, reagents and chemicals. Examples of these reagents include single-stranded binding proteins such as Rec A protein, T4 gene 32 protein, *E. coli* single-stranded binding protein and major or minor nucleic acid groove binding proteins.

Other examples of such reagents and chemicals include divalent ions, polyvalent ions and intercalating substances such as ethidium bromide, actinomycin D, psoralen, and angelicin.

Essentially any available method for detecting target nucleic acids can be used in the present invention. Common approaches include real-time amplification detection with 5'-nuclease probes, SCORPION® primers, or molecular beacons, detection of intercalating dyes, detection of labels incorporated into the amplification probes or the amplified nucleic acids themselves, e.g., following electrophoretic separation of the amplification products from unincorporated label, hybridization based assays (e.g., array based assays), and/or detection of secondary reagents that bind to the nucleic acids. For example, a 5'-nuclease probe or a molecular beacon is optionally designed to include a oligonucleotide sequence that targets a particular nucleic acid (e.g., a nucleic acid from *Neisseria gonorrhoeae*, *Neisseria meningitidis*, human immunodeficiency virus (HIV), hepatitis C virus (HCV), papilloma virus, *Plasmodium falciparum*, *Chlamydia muridarum*, *Chlamydia trachomatis*, among many others). Molecular beacons and 5'-nuclease probes are described further below. These general approaches are also described in, e.g., Sambrook, and Ausubel 1 and 2.

In certain embodiments, real-time PCR assay systems that include one or more 5'-nuclease probes are used for detecting amplified target nucleic acids in the presence of the light emission modifiers described herein. As described above, these systems operate by using the endogenous nuclease activity of certain polymerases to cleave a quencher or other label free from a probe that comprises the quencher and label, resulting in unquenching of the label. The polymerase typically only cleaves the quencher or label upon initiation of replication, i.e., when the oligonucleotide is bound to the template and the polymerase extends the primer. Thus, an appropriately labeled probe nucleic acid and a polymerase comprising the appropriate nuclease activity can be used to detect a target nucleic acid of interest. Real-time PCR product analysis by, e.g., FRET or the like (and related kinetic reverse-transcription PCR) provides a well-known technique for real time PCR monitoring that has been used in a variety of contexts, which can be adapted for use with the methods described herein (see, Laurendeau et al. (1999) "TaqMan PCR-based gene dosage assay for predictive testing in individuals from a cancer family with INK4 locus haploinsufficiency" *Clin Chem* 45(7):982-6; Laurendeau et al. (1999) "Quantitation of MYC gene expression in sporadic breast tumors with a real-time reverse transcription-PCR assay" *Clin Chem* 59(12):2759-65; and Kreuzer et al. (1999) "Light-Cycler technology for the quantitation of bcr/ab1 fusion transcripts" *Cancer Research* 59(13):3171-4, all of which are incorporated by reference).

Exemplary commercially available systems that are optionally utilized to detect target nucleic acids using the reaction mixtures described herein include, e.g., a COBAS® TaqMan® system, a COBAS AMPLICOR® Analyzer, or a LightCycler® system, which are available from Roche Diagnostics Corporation (Indianapolis, Ind., USA), a LUMINEX 100™ system, which is available from the Luminex Corporation (Austin, Tex., USA), a ABI PRISM® 7700 system, which is available from Applied Biosystems (Foster City, Calif., USA), and the like. Systems are also described below.

Molecular beacons are oligonucleotides designed for real-time detection and quantification of target nucleic acids. The 5' and 3' termini of molecular beacons collectively comprise a pair of moieties, which confers the detectable properties of the molecular beacon. One of the termini is attached to a fluorophore and the other is attached to a quencher molecule capable of quenching a fluorescent emission of the fluorophore. To illustrate, one example fluorophore-quencher pair can use a fluorophore, such as EDANS or fluorescein, e.g., on the 5'-end and a quencher, such as Dabcyl, e.g., on the 3'-end. When the molecular beacon is present free in solution, i.e., not hybridized to a second nucleic acid, the stem of the molecular beacon is stabilized by complementary base pairing. This self-complementary pairing results in a "hairpin loop" structure for the molecular beacon in which the fluorophore and the quenching moieties are proximal to one another. In this confirmation, the fluorescent moiety is quenched by the quenching moiety. The loop of the molecular beacon typically comprises the oligonucleotide probe and is accordingly complementary to a sequence to be detected in the target nucleic acid, such that hybridization of the loop to its complementary sequence in the target forces disassociation of the stem, thereby distancing the fluorophore and quencher from each other. This results in unquenching of the fluorophore, causing an increase in fluorescence of the molecular beacon.

Details regarding standard methods of making and using molecular beacons are well established in the literature and molecular beacons are available from a number of commercial reagent sources. Further details regarding methods of molecular beacon manufacture and use are found, e.g., in Leone et al. (1995) "Molecular beacon probes combined with amplification by NASBA enable homogenous real-time detection of RNA," *Nucleic Acids Res.* 26:2150-2155; Kostrikis et al. (1998) "Molecular beacons: spectral genotyping of human alleles" *Science* 279:1228-1229; Fang et al. (1999) "Designing a novel molecular beacon for surface-immobilized DNA hybridization studies" *J. Am. Chem. Soc.* 121: 2921-2922; and Marras et al. (1999) "Multiplex detection of single-nucleotide variation using molecular beacons" *Genet. Anal. Biomol. Eng.* 14:151-156, all of which are incorporated by reference. A variety of commercial suppliers produce standard and custom molecular beacons, including Oswel Research Products Ltd. (UK), Research Genetics (a division of Invitrogen, Huntsville, Ala., USA), the Midland Certified Reagent Company (Midland, Tex., USA), and Gorilla Genomics, LLC (Alameda, Calif., USA). A variety of kits which utilize molecular beacons are also commercially available, such as the Sentinel™ Molecular Beacon Allelic Discrimination Kits from Stratagene (La Jolla, Calif., USA) and various kits from Eurogentec SA (Belgium) and Isogen Bioscience BV (Netherlands).

SCORPION® primers are used in fluorescence based approaches for the specific detection of PCR products (Whitcombe et al. (1999) *Nat. Biotechnol.* 17:804-807, Whitcome et al. (1999) *Am J. Hum. Genet.* 65:2333, and Thelwell et al. (2000) *Nucl. Acids Res.* 28:3752-3761, which are each incorporated by reference). A SCORPION® primer generally includes a specific probe sequence that is held in a hairpin loop configuration by complementary stem sequences on the 5' and 3' sides of the probe. The fluorescent label attached to the 5'-end is quenched by a quencher moiety attached to the 3'-end of the loop. The hairpin loop is linked to the 5'-end of a primer typically via a PCR stopper. After extension of the primer during PCR amplification, the specific probe sequence is able to bind to its complement within the same strand of DNA. This hybridization event opens the hairpin loop so that fluorescence is no longer quenched and an increase in signal is observed. The PCR stopper prevents read-through, which can lead to opening the hairpin loop in the absence of the specific target sequence. Such read-through would lead to the detection of non-specific PCR products, such as primer dimers or mispriming events. SCORPION® primers are also described in, e.g., Huang et al. (2004) "Real-time quantitative assay of telomerase activity using the duplex scorpion primer," *Biotechnol Lett.* 26(11):891-895, Asselbergs et al. (2003) "Rapid detection of apoptosis through real-time reverse transcriptase polymerase chain reaction measurement of the small cytoplasmic RNA Y1," *Anal Biochem.* 318(2): 221-229, and Nuovo et al. (1999) "In situ amplification using universal energy transfer-labeled primers," *J Histochem Cytochem.* 47(3):273-280, which are each incorporated by reference.

Systems

The invention also provides systems for detecting target nucleic acids. The system includes one or more labeled oligonucleotides and one or more light emission modifiers as described herein. In certain embodiments, the oligonucleotides are arrayed on a solid support, whereas in others, they are provided in one or more containers, e.g., for assays performed in solution. The system also includes at least one detector (e.g., a spectrometer, etc.) that detects binding between nucleic acids and/or amplicons thereof from the sample and the oligonucleotides. In addition, the systems also optionally include at least one thermal modulator (e.g., a thermal cycling device, etc.) operably connected to the container or solid support to modulate temperature in the container or on the solid support, and/or at least one fluid transfer component (e.g., an automated pipettor, etc.) that transfers fluid to and/or from the container or solid support, e.g., for performing one or more nucleic acid amplification techniques and/or nucleic acid hybridization assays in the container or on the solid support.

Detectors are typically structured to detect detectable signals produced, e.g., in or proximal to another component of the given assay system (e.g., in container, on a solid support, etc.). Suitable signal detectors that are optionally utilized, or adapted for use, herein detect, e.g., fluorescence, phosphorescence, radioactivity, absorbance, refractive index, luminescence, mass, or the like. Detectors optionally monitor one or a plurality of signals from upstream and/or downstream of the performance of, e.g., a given assay step. For example, detectors optionally monitor a plurality of optical signals, which correspond in position to "real-time" results. Example detectors or sensors include photomultiplier tubes, CCD arrays, optical sensors, temperature sensors, pressure sensors, pH sensors, conductivity sensors, scanning detectors, or the like. More specific exemplary detectors that are optionally utilized in performing the methods of the invention include, e.g., resonance light scattering detectors, emission spectroscopes, fluorescence spectroscopes, phosphorescence spectroscopes, luminescence spectroscopes, spectrophotometers, photometers, and the like. Detectors are also described in, e.g., Skoog et al., *Principles of Instrumental Analysis*, 5$^{th}$ Ed., Harcourt Brace College Publishers (1998) and Currell, *Analytical Instrumentation: Performance Characteristics and Quality*, John Wiley & Sons, Inc. (2000), both of which are incorporated by reference.

The systems of the invention also typically include controllers that are operably connected to one or more components (e.g., detectors, thermal modulators, fluid transfer components, etc.) of the system to control operation of the components. More specifically, controllers are generally included either as separate or integral system components that are utilized, e.g., to receive data from detectors, to effect and/or regulate temperature in the containers, to effect and/or regulate fluid flow to or from selected containers, or the like. Controllers and/or other system components is/are optionally coupled to an appropriately programmed processor, computer, digital device, or other information appliance (e.g., including an analog to digital or digital to analog converter as needed), which functions to instruct the operation of these instruments in accordance with preprogrammed or user input instructions, receive data and information from these instruments, and interpret, manipulate and report this information to the user. Suitable controllers are generally known in the art and are available from various commercial sources.

Any controller or computer optionally includes a monitor, which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. These components are illustrated further below.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming, e.g., such as controlling fluid flow regulators in response to fluid weight data received from weight scales or the like.

Figure 3:
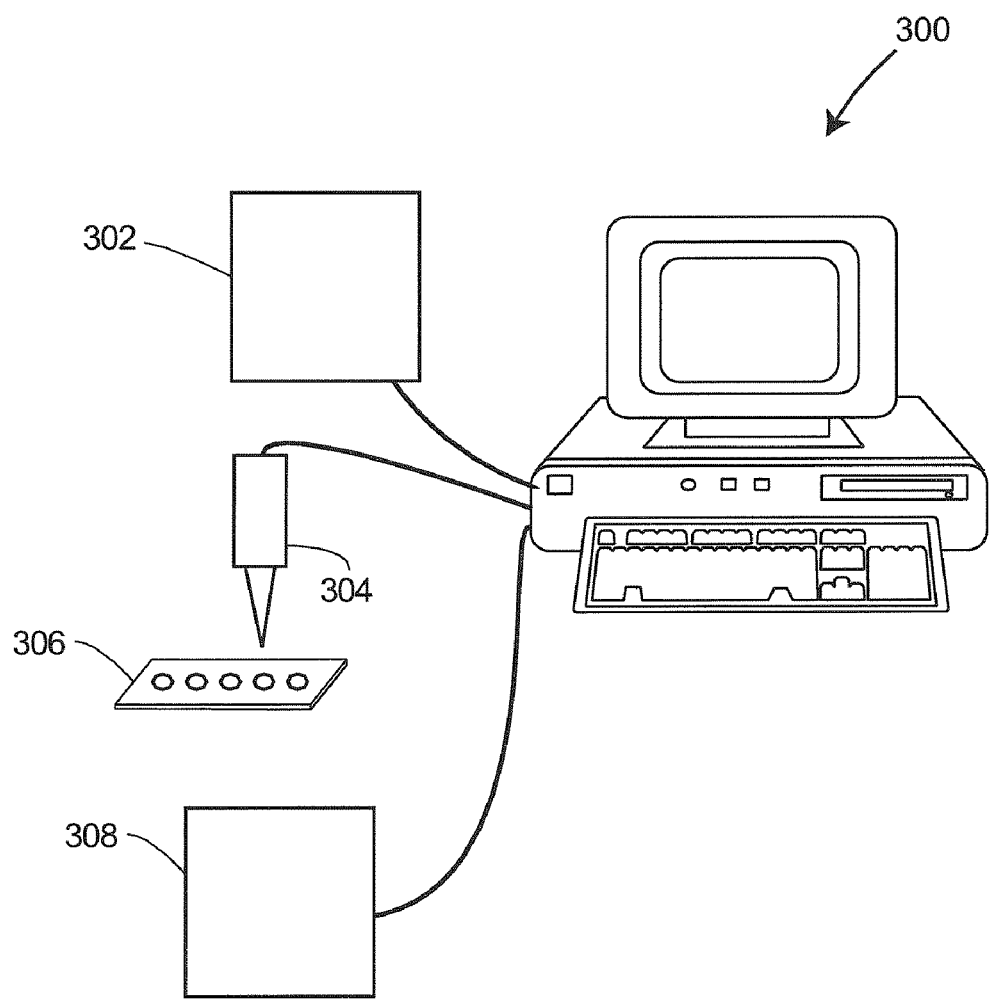
FIG. 3 is a block diagram showing a representative system according to one embodiment of the invention.

FIG. 3 is a schematic showing a representative system that includes a logic device in which various aspects of the present invention may be embodied. As will be understood by practitioners in the art from the teachings provided herein, the invention is optionally implemented in hardware and/or software. In some embodiments, different aspects of the invention are implemented in either client-side logic or server-side logic. As will be understood in the art, the invention or components thereof may be embodied in a media program component (e.g., a fixed media component) containing logic instructions and/or data that, when loaded into an appropriately configured computing device, cause that device to perform according to the invention. As will also be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

In particular, FIG. 3 schematically illustrates computer 300 to which detector 302, fluid transfer component 304, and thermal modulator 308 are operably connected. Optionally, one or more of these components are operably connected to computer 300 via a server (not shown in FIG. 3). During operation, fluid transfer component 304 typically transfers reaction mixtures or components thereof to multi-well container 306. Thermal cycling is typically effected by thermal modulator 308, which thermally communicates with multi-well container 306. Detector 302 typically detects detectable signals (e.g., fluorescent emissions, etc.) produced during thermal cycling reactions.

Kits

The reaction mixtures or components thereof (e.g., probes or light emission modifiers) employed in the methods of the present invention are optionally packaged into kits. In addition, the kits may also include suitably packaged reagents and materials needed for target nucleic acid hybridization, amplification, and detection, such buffers, enzymes, DNA standards, salts, metal ions, primers, extendible or terminator nucleotides, glycerol, dimethyl sulfoxide, poly rA, etc. as well as instructions for conducting a particular assay. Kit components, such as probes and light emission modifiers are typically provided in one or more containers. In some of these embodiments, the kits further include at least one pyrophosphatase (e.g., a thermostable pyrophosphatase), e.g., for use in minimizing pyrophosphorolysis, and/or uracil N-glycosylase (UNG), e.g., for use in applications where protection against carry-over contamination is desirable. Two or more of the kit components may be packaged within the same container.

The Use of Soluble Light Emission Modifiers in Tm Determinations

The invention provides methods for determining the melting temperature ($T_m$) of a hybridization complex, where these methods use the soluble light emission modifier technology taught herein. The Tm determinations use a soluble light emission modifier (i.e., a soluble quencher) system to monitor the duplex melting curve or annealing curve.

Essentially, a probe labeled with a suitable light emitting moiety (e.g., a donor) is hybridized with a target to form a hybridization complex. The resulting hybridization duplex (e.g., target hybridization complex) can have either complete complementarity (i.e., 100%) or partial complementarity (i.e., less than 100%). Any nucleic acid duplex (with complete or partial complementarity) is characterized by a particular Tm at a give set of hybridization conditions. It is this feature that makes Tm determinations useful in applications such as diagnostics (e.g., SNP detection, mutation detection and mutation scanning, viral genotyping, testing for drug resistant strains etc.).

Either before, during or after formation of the duplex, the reaction is admixed with a suitable soluble quencher. This soluble quencher comprises a thiazine dye or a diazine dye, where the soluble quencher is capable of quenching the light emitting moiety on the probe (thus forming a donor-acceptor pair). Any thiazine dye or diazine dye provided herein can be used in the Tm determination methods of the invention. It is noted that thiazine, phenothiazine, cationic thiazines, thiazinium, and phenothiazinium are all synonyms for a generic name for the family of dyes with fused 3-ring aromatic system containing a nitrogen and a sulfur in the middle ring. Furthermore, in addition to the particular thiazine and diazine structures taught herein, related structural variants of these molecules that retain the soluble quencher property can also be used with the methods of the invention, and are encompassed within the scope of the invention.

A thiazine dye or diazine dye soluble quencher acts by binding to both single and double-stranded nucleic acid, but has reduced affinity for single-stranded nucleic acid. It is contemplated that the binding to the single stranded nucleic acids could be due to partial secondary structures in the random coil state. Without being bound to any particular theory, it is believed that the predominant binding mode is through intercalation, but minor and major groove binding is also possible depending on the sequence context and hybridization conditions (see, Rohs et al. (2000) J. Am. Chem. Soc., 122:2860-2866; and Tuite et al. (1994) J. Am. Chem. Soc., 116:7548-7556). Thus, the fluorescence donor label attached to the probe that forms the hybridization complex with a target polynucleotide is subject to a quenching effect by the intercalating soluble quencher that has an affinity for double-stranded nucleic acid due to the close proximity of the quencher to the donor moiety on the probe. However, an understanding of the molecular mechanisms of the quenching phenomenon is not required to make or use the invention.

If the solution containing the hybridization complex is heated (as in the melting curve Tm analysis), the probe eventually dissociates from the target polynucleotide, thereby reducing the affinity of the quencher for the nucleic acid, resulting in reduced proximity of the soluble quencher to the probe donor and an increase in fluorescence from the donor is observed. Thus, the formation/dissociation of hybridization complexes in a reaction can be monitored by the use of a system having a soluble quencher.

Following formation of the duplex under conditions where base-pairing can occur, the temperature of the target hybridization complex reaction is raised and the emission from the donor is measured and monitored over a range of temperatures, thus forming a melting curve. A temperature range of, for example, about 20° C. to about 95° C. can be used. Alternatively, the probe, soluble quencher and target can start at an elevated temperature (e.g., about 95° C.), and the donor emission is monitored while the temperate of the reaction is lowered (e.g., to about 20° C.), thus generating an annealing curve.

The Examples illustrating Tm determinations provided herein use a single-labeled oligonucleotide probe, where the probe is labeled with FAM (6-carboxy-fluorescein), which serves as the light-emitting donor moiety in the donor/quencher pair with the soluble quencher. It will be apparent to one of skill that it is not intended that the present invention be limited to the use of FAM as the donor moiety. Indeed, the art it replete with descriptions of other label moieties, all of which find use with the invention as light emitting donor moieties. It is intended that these additional light emitting moieties also fall within the scope of the invention.

In either case of an annealing curve or a melting curve, the measured emission from the donor is correlated with a particular duplex association/dissociation value, and a Tm is derived where the Tm is that temperature at which one half of a population of hybridization complexes becomes dissociated into single strands.

The invention provides numerous examples of Tm determinations using soluble quencher systems of the invention. For example, see Examples 19-22. Many of the Examples provided herein utilize the soluble quencher reagents in viral genotyping methods, for example, HCV genotyping. In these methods, various viral genomic sequences are used as hybridization targets for a probe that is labeled with a light emitting moiety (e.g., a donor such as FAM). Adaptation of these methods find particular use in viral detection and genotyping in clinical samples, for example, samples from patients. However, it is not intended that the Tm determination methods of the invention be limited to viral genotyping applications. That is to say, it is not intended that the hybridization targets be viral material or nucleic acids derived from viral material. Indeed, a wide variety of applications in addition to viral genotyping are immediately apparent to one of skill in the art. For example, Tm determinations employing soluble quencher reagents can have use in coupled amplification, detection and analysis in a closed tube format and using single labeled probes. These methods find uses in a wide variety of applications for example but not limited to such applications as SNP and mutation detection, haplotyping, microsatellite detection, characterization of pathogen genotypes, and characterization of drug resistant strains The nature of the hybridization target is not particularly limited. In some aspects, the hybridization target can be an amplicon, for example, an amplicon produced by a polymerase chain reaction. In some aspects, the PCR amplification can use an asymmetric amplification. In the case where the target nucleic acid of interest is an RNA molecule, the PCR amplification can employ reverse transcription PCR (RT-PCR).

Additional detailed description of general Tm methodologies and Tm determinations that utilize soluble light emission modifiers (i.e., soluble quenchers) is found in cofiled U.S. patent application Ser. No. 11/474,125, filed on Jun. 23, 2006, entitled "PROBES AND METHODS FOR HEPATITIS C VIRUS TYPING USING SINGLE PROBE ANALYSIS," by Gupta and Will; and also in cofiled U.S. patent application Ser. No. 11/474,092, filed on Jun. 23, 2006, entitled "PROBES AND METHODS FOR HEPATITIS C VIRUS TYPING USING MULTIDIMENSIONAL PROBE ANALYSIS," by Gupta and Will. The entire content of these two cofiled applications are hereby incorporated by reference in their entirety for all purposes.

Kits for Tm Determination

The invention provides articles of manufacture, for example, kits to facilitate the methods of the present invention, e.g., methods for conducting Tm determinations. These kits provide the materials necessary for making a Tm determination using the methods described herein. These kits find use for the clinician, who can use the Tm assessments, for example, to make viral genotyping determinations. Materials and reagents to carry out these methods can be provided in the kits to facilitate execution of the methods.

In some embodiments, the Tm determination kits are diagnostic kits, where the information obtained from performing the methods enabled by the kits is used, e.g., to identify the genotype of a virus in a sample taken from a patient.

In certain embodiments, the invention provides kits suitable for conducting target amplification in addition to target Tm determination, for example, by incorporating PCR or RT-PCR reagents.

In some embodiments, the present invention provides kits for determining the melting temperature (Tm) of a particular hybridization complex, where the Tm determination uses a soluble light emission modifier (e.g., a soluble quencher) system to monitor the duplex melting curve or annealing curve. These kits include, but are not limited to, (i) at least one probe labeled with a suitable light emitting moiety (e.g., a donor), (ii) a soluble light emission modifier such as a thiazine dye or a diazine dye, where the dye is capable of quenching the light emitting moiety, and (iii) one or more containers that hold the probe, the soluble quencher, or both the probe and the soluble quencher.

Kits can also optionally include reagents for sample collection (e.g., the collection of a blood sample), reagents for the collection and purification of RNA from blood, a reverse transcriptase, primers suitable for reverse transcription and first strand and second strand cDNA synthesis (i.e., reverse transcriptase initiation), e.g., to produce a viral amplicon, a thermostable DNA-dependent DNA polymerase and free deoxyribonucleotide triphosphates. In some embodiments, the enzyme comprising reverse transcriptase activity and thermostable DNA-dependent DNA polymerase activity are the same enzyme, e.g., *Thermus* sp. ZO5 polymerase or *Thermus thermophilus* polymerase. The kits of the invention can also optionally include standardization samples (e.g., standardization nucleic acid templates at known concentrations to assess the sensitivity of the Tm method); positive control samples (for example, defined sequence nucleic acid templates with known, previously determined Tm values), negative control samples (e.g., buffers or reaction mixtures that do not contain any nucleic acid target), buffers suitable for enzymatic reactions, sample collection tubes and amplification reaction tubes.

Tm Determination Systems

In some embodiments, the invention provides integrated systems for making Tm determinations. The systems can include instrumentation and means for interpreting and analyzing collected data, especially where the means for deriving the Tm comprise algorithms and/or electronically stored information (e.g., collected fluorescence data, predetermined Tm correlations, etc). Each part of an integrated system is functionally interconnected, and in some cases, physically connected. In some embodiments, the integrated system is automated, where there is no requirement for any manipulation of the sample or instrumentation by an operator following initiation of the Tm analysis.

A system of the invention can include instrumentation. For example, the invention can include a detector such as a fluorescence detector (e.g., a fluorescence spectrophotometer). A detector or detectors can be used in conjunction with the invention, e.g., to monitor/measure the emission from the light emitting moiety on the Tm probe. A detector can be in the form of a multiwell plate reader to facilitate the high-throughput capacity of the Tm assay.

In some embodiments, the integrated system includes a thermal cycling device, or thermocycler, for the purpose of controlling the temperature of the Tm melting analysis. In some embodiments, the thermal cycling device and the detector are an integrated instrument, where the thermal cycling and emission detection (e.g., fluorescence detection) are done in the same device.

A detector, e.g., a fluorescence spectrophotometer, can be connected to a computer for controlling the spectrophotometer operational parameters (e.g., wavelength of the excitation and/or wavelength of the detected emission) and/or for storage of data collected from the detector (e.g., fluorescence measurements during a melting curve analysis). The computer may also be operably connected to the thermal cycling device to control the temperature, timing, and/or rate of temperature change in the system. The integrated computer can also contain the "correlation module" where the data collected from the detector is analyzed and where the Tm of the target hybridization complex is determined (electronically). In some embodiments, the correlation module comprises a computer program that calculates the Tm based on the fluorescence readings from the detector, and in some cases, optionally derives viral genotype information of an unknown sample based on the Tm result. In some embodiments, the correlation module compares the $T_m$ of the unknown sample with a database (or table) of Tm values for known viral types to make a correlation between the Tm of the unknown sample and the viral genotype of the unknown sample.

In some aspects, a system of the invention for the determination of a Tm of a hybridization complex comprises a reaction mixture (e.g., which may or may not include a sample) that includes (i) a nucleic acid probe comprising a light emitting moiety that emits a signal; (ii) a hybridization target nucleic acid that is complementary or partially complementary to the nucleic acid probe; and (iii) a thiazine dye or a diazine dye. The system also includes a thermal control device for regulating the temperature of the melting reaction over a range of temperatures, where the range of temperatures includes a temperature where essentially all probe molecules anneal with the hybridization target at a given set of hybridization conditions, a temperature where 50% of the target hybridization complexes are dissociated, and a temperature where essentially no probe molecules anneal with the hybridization target and essentially no hybridization complexes are present at the hybridization conditions. The system can further include a detector for measuring the signal from the melting reaction over the range of temperatures; and also a correlation module that is operably coupled to the detector and receives signal measurements over the range of temperatures, where the correlation module correlates the signal intensity with the presence of a hybridization complex comprising the probe and the hybridization target in admixture with the thiazine dye or diazine dye as a function of temperature, thereby determining the $T_m$ of the target hybridization complex. In some aspects, the light emitting moiety on the probe is a FRET donor moiety.

Use of Thiazine Dyes for Duplex Stabilization

A variety of nucleic acid techniques suffer from sequence mismatches in the amplification and/or detection of nucleic acids. The present invention provides solutions to this problem, where the invention provides methods for stabilizing nucleic acid duplexes. These methods for nucleic acid duplex stabilization are effective at stabilizing nucleic acid duplexes that contain single mismatch positions as well as duplexes with multiple mismatch positions. Indeed, the methods described herein can even further stabilize perfectly matched nucleic acid duplexes. The further stabilization of perfectly matched duplexes will allow the preservation of intact nucleic acid duplexes under conditions where the duplex would otherwise dissociate.

As provided in the present disclosure, a number of compounds are identified herein that can bind and significantly stabilize mismatches in nucleic acid duplexes. These are members of the thiazine dye family, for example but not limited to, thionin (also known as thionine), methylene blue, new methylene blue, 1,9-dimethly methylene blue, methylene grene, azure A, azure B, azure C, and toluidine blue.

Any thiazine dye provided herein can be used in the duplex stabilization methods of the invention. Furthermore, in addition to the particular thiazine structures taught herein, related structural variants of these molecules that retain the essential stabilization property can also be used with the methods of the invention. Such related molecules are encompassed within the scope of the invention.

By using the thiazine dyes and related compounds as additives to hybridization reactions, nucleic acid amplification and detection can be vastly improved in those situations where polymorphism exists under the probes and/or primers. These are in fact the most demanding applications where the stabilization additive must not adversely affect the enzymatic activity (e.g., PCR or RT-PCR amplification). Any applications where the stabilization of mismatches is required will benefit from these protocols. Furthermore, applications where there is improved stabilization of a perfectly matched duplex can also benefit from these protocols. Any type of nucleic acid hybridization that yields a nucleic acid hybridization complex can benefit from the methods of the invention. This includes, but is not limited to, for example, the hybridization of one or a plurality of enzymatically-extendable PCR primers to a target sequence; the hybridization of any nucleic acid molecules where the site of hybridization serves an initiation point that is effective to prime a nucleic acid extension reaction; the hybridization of a 5'-nuclease probe to a target; the hybridization of any type of labeled (or unlabeled) probe to a target such as used in southern blotting or northern blotting; and the use of nucleic acid probes in any type of screening, such as in genomic library or cDNA library screening. In some embodiments, the target nucleic acid molecule in the hybridization is an amplicon.

In some aspects, by using the thiazine dyes and related compounds as additives to hybridization reactions, nucleic acid amplification and detection can be vastly improved in those situations where polymorphism exists under the probes and/or primers, for example, in viral genotyping analysis.

The invention provides numerous examples of duplex stabilization using thiazine dyes. For example, see Examples 20-25. Many of the Examples provided herein utilize HCV or HIV viral model systems to illustrate the advantageous properties of the methods of the invention with regard to duplex stabilization. However, it is not intended that the duplex stabilization methods of the invention be limited to viral hybridization applications. That is to say, it is not intended that the stabilized duplexes comprise viral material or nucleic acids derived from viral material. Indeed, a wide variety of other applications in addition to viral genetic analysis are immediately apparent to one of skill in the art.

Essentially, the methods for stabilizing the nucleic acid duplex consist of exposing the nucleic acid duplex to the stabilizing thiazine dye. The thiazine dye can be admixed with the duplex at any point, for example, prior to formation of the duplex, or after formation of the duplex. The thiazine can be present or absent during the annealing of the two or more single strands of nucleic acid that form the duplex. In the case where the thiazine dye is absent during the formation of the duplex, the dye can be added after the duplex is formed.

The improved stability of the duplex using the stabilization methods of the invention can be observed by using any suitable assay to determine duplex stability. For example, the Tm of a nucleic acid duplex in the absence of a thiazine dye can be compared to the Tm of the same nucleic acid duplex in the presence of the thiazine dye under the same hybridization conditions. Alternatively, a $C_T$ growth curve (e.g., a $C_T$ growth curve that uses a 5'-nuclease assay probe) can be conducted under similar conditions, where the $C_T$ value in the absence of the thiazine dye is compared to the $C_T$ value in the presence of the thiazine dye. Note that when a $C_T$ value is used to illustrate duplex stability, that $C_T$ value can be a reflection of the duplex stability of either or both amplification primers, and furthermore, also reflects the stability of any probe-containing duplex that is used to monitor the amplicon accumulation (e.g., a 5'-nuclease probe in a 5'-nuclease assay). It is significant to point out that when $C_T$ determinations are made to assess duplex stability, a 5'-nuclease assay need not be used to monitor amplicon accumulation. As illustrated in Example 25, a probeless monitoring system can be used, such as by monitoring amplicon accumulation using a double-stranded nucleic acid indicator such as SYBR® Green.

These methods for comparing duplex stability in dye-absent versus dye-present systems also apply to comparing the stability of duplexes that are stabilized by any two different concentrations of a thiazine dye, for example, a high concentration and a low concentration.

The present invention provides methods for stabilizing nucleic acid duplexes, where the duplexes can be perfectly matched duplexes, or contain any number of mismatch positions. For example, these methods for nucleic acid duplex stabilization are effective at stabilizing nucleic acid duplexes that contain one or more mismatch positions, two or more mismatch positions, or three or more mismatch positions.

In the methods for nucleic acid duplex stabilization, the concentration of the thiazine dye that is used in the methods is not particularly limited. In some aspects, a concentration of at least 10 µg/mL is used. In other aspects, any concentration within a range of concentrations is used, for example, a concentration of between about 10 µg/mL and about 50 µg/mL.

Alternatively, a concentration range of about 20 µg/mL and about 40 µg/mL is used. In some aspects, a thiazine dye concentration of about 40 µg/mL is used.

Typically, in the methods for stabilizing nucleic acid duplexes, the stabilized hybridization complex is an intermolecular hybridization complex, where the antiparallel hybridizing strands are two separate nucleic acid molecules. However, in some adaptations of the methods for stabilizing nucleic acid duplexes, the stabilized hybridization complex is an intramolecular hybridization complex, where the antiparallel hybridizing strands are actually on a single nucleic acid molecule, such as in the case of a molecular beacon type configuration.

EXAMPLES

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims.

These examples show performance data obtained for certain 5'-nuclease assays in which light emission modifiers of the present invention were utilized.

Example 1

General Protocols for Fluorescence Quenching Assays

The tables included in this section describe the respective reaction components, conditions, and procedures that were utilized in the analyses referred to in the examples provided below, unless specified otherwise. In general, the fluorescence of labeled oligonucleotides was measured in solutions both with and without a soluble quencher. In certain analyses, for example, a series of probes labeled with FAM at the 5' end were measured in 400 µL solutions containing a PCR reaction buffer (described below) and various concentrations of soluble quenchers. For detecting the fluorescence of the FAM label in those analyses, the wavelength of the excitation light was chosen to be 485 nanometers and the fluorescence was measured at a wavelength of 520 nanometers.

General Methods used for PCR Evaluations

TABLE III

Reaction mixture for quenching analyses
using a single stranded fluorescent oligonucleotide:

| Component | Concentration |
|---|---|
| poly rA carrier | 9 µg/mL |
| Glycerol | 6.2% |
| DMSO | 7.5% |
| Tricine, pH 8.3 | 50 mM |
| KOAc | 100 mM |
| dATP | 300 µM each |
| dCTP | |
| dGTP | |
| dUTP | 550 µM |
| SK145BU | 0.4 µM |
| (mock amplification primer) | (40 pmol/rx) |
| GAG152BU | 0.4 µM |
| (mock amplification primer) | (40 pmol/rx) |
| GAG108AF | 0.1 µM |
| (fluorescent oligonucleotide) | |

TABLE III-continued

Reaction mixture for quenching analyses
using a single stranded fluorescent oligonucleotide:

| Component | Concentration |
|---|---|
| UNG (Uracil N-Glycosylase) | 10 U/reaction (rx) |
| ZO5 DNA polymerase | 40 U/reaction |
| EDTA | 5 mM |
| Mn(OAc)$_2$ | 3 mM |
| Light emission modifier | 0-50 µg/mL |

TABLE IV

Reaction mixture for quenching analyses using
a double stranded fluorescent oligonucleotide:

| Component | Concentration |
|---|---|
| poly rA carrier | 9 µg/mL |
| Glycerol | 6.2% |
| DMSO | 7.5% |
| Tricine, pH 8.3 | 50 mM |
| KOAc | 100 mM |
| dATP | 300 µM each |
| dCTP | |
| dGTP | |
| dUTP | 550 µM |
| SK145BU | 0.4 µM |
| (mock amplification primer) | (40 pmol/rx) |
| GAG152BU | 0.4 µM |
| (mock amplification primer) | (40 pmol/rx) |
| GAG108AF | 0.1 µM |
| (fluorescent oligonucleotide) | |
| GAG100C | 0.1 µM |
| (complement to GAG108AF) | |
| UNG (Uracil N-Glycosylase) | 10 U/reaction |
| ZO5 DNA polymerase | 40 U/reaction |
| EDTA | 5 mM |
| Mn(OAc)$_2$ | 3 mM |
| Light emission modifier | 0-50 µg/mL |

TABLE V

Reaction mixture for quenching analyses
using a fluorescent dinucleotide:

| Component | Concentration |
|---|---|
| poly rA carrier | 9 µg/mL |
| Glycerol | 6.2% |
| DMSO | 7.5% |
| Tricine, pH 8.3 | 50 mM |
| KOAc | 100 mM |
| dATP | 300 µM each |
| dCTP | |
| dGTP | |
| dUTP | 550 µM |
| SK145BU | 0.4 µM |
| (mock amplification primer) | (40 pmol/rx) |
| GAG152BU | 0.4 µM |
| (mock amplification primer) | (40 pmol/rx) |
| FAM-TT | 0.1 µM |
| (fluorescent dinucleotide) | |
| UNG (Uracil N-Glycosylase) | 10 U/reaction |
| ZO5 DNA polymerase | 40 U/reaction |
| EDTA | 5 mM |
| Mn(OAc)$_2$ | 3 mM |
| Light emission modifier | 0-50 µg/mL |

Sequence Information

TABLE VI
HCV Sequences

| Amplification primer | Sequence | SEQ ID NO |
|---|---|---|
| ST280ATBUA1 | GCAGAAAGCGTCTAGCCATGGCGTTX where X = N6-t-butylbenzyl-dA | 1 |
| ST778AATBA1 | GCAAGCACCCTATCAGGCAGTACCACAX where X = N6-t-butylbenzyl-dA | 2 |
| ST650AAFBHQ2 Quenched 5'-Nuclease Probe | ECGGTGTACTCACCGJTTCCGCAGACCACTATGP Where E = FAM; J = BHQ-2; P = Terminal Phosphate | 3 |
| ST650ACY5F14IN Quenched 5'-Nuclease Probe | ECGGTGTACTCACCGJGTTCCGCAGACCACTATGP where E = CY5; J = cx-FAM; P = Terminal Phosphate | 4 |
| ST650A_5'-FL Single-labeled Probe | ECGGTGTACTCACCGTTCCGCAGACCACTATGP where E = FAM; P = Terminal Phosphate | 5 |

TABLE VII
HIV Sequences

| Amplification primer | Sequence | SEQ ID NO |
|---|---|---|
| SK145BU | AGTGGGGGGACATCAAGCAGCCATGCAAX where X = N6-t-butylbenzyl-dA | 6 |
| GAG152BU | GGTACTAGTAGTTCCTGCTATGTCACTTCX where X = N6-t-butylbenzyl-dA | 7 |
| GAG100C (complement-GAG108) | TAAAAGATACCATCAATGAGGAAGCTGCAGAP where P = Terminal Phosphate | 8 |
| GAG108_5'-FAM Single-labeled probe | ETCTGCAGCTTCCTCATTGATGGTATCTTTTAP where E = FAM; P = Terminal Phosphate | 9 |

TABLE VIII
Quantitation standard (QS)

| Amplification primer | Sequence | SEQ ID NO |
|---|---|---|
| ST280ATBUA1 | GCAGAAAGCGTCTAGCCATGGCGTTX where X = N6-t-butylbenzyl-dA | 10 |
| ST778AATBA1 | GCAAGCACCCTATCAGGCAGTACCACAX where X = N6-t-butylbenzyl-dA | 11 |
| ST2535_5-HEX Single-labeled Probe | ETGGACTCAGTCCTCTGGTCATCTCACCTTCTP where E = HEX; P = Terminal Phosphate | 12 |

TABLE IX
Reaction mixture for HCV PCR using a single-labeled fluorescent probe

| Component | Concentration |
|---|---|
| poly rA carrier | 9 μg/mL |
| Glycerol | 6.2% |
| DMSO | 7.5% |
| Tricine, pH 8.3 | 50 mM |
| KOAc | 100 mM |
| dATP | 300 μM each |
| dCTP | |
| dGTP | |
| dUTP | 550 μM |
| ST280ATBUA1 amplification primer | 0.4 μM (40 pmol/rx) |
| ST778AATBA1 amplification primer | 0.4 μM (40 pmol/rx) |
| ST650_5'-FAM | 0.1 μM |

TABLE IX-continued

Reaction mixture for HCV PCR using a single-labeled fluorescent probe

| Component | Concentration |
| --- | --- |
| (single-labeled fluorescent probe) | (10 pmol/rx) |
| UNG (Uracil N-Glycosylase) | 10 U/reaction |
| ZO5 DNA polymerase | 40 U/reaction |
| Mn(OAc)$_2$ | 3 mM |
| Light emission modifier | 0-50 μg/mL |
| HCV TARGET DNA | 2-10$^6$ copies per reaction |

TABLE X

Reaction mixture for HCV PCR using a quenched 5'-nuclease probe

| Component | Concentration |
| --- | --- |
| poly rA carrier | 9 μg/mL |
| Glycerol | 6.2% |
| DMSO | 7.5% |
| Tricine, pH 8.3 | 50 mM |
| KOAc | 100 mM |
| dATP | 300 μM each |
| dCTP | |
| dGTP | |
| dUTP | 550 μM |
| ST280ATBUA1 (amplification primer) | 0.4 μM (40 pmol/rx) |
| ST778AATBA1 (amplification primer) | 0.4 μM (40 pmol/rx) |
| ST650AAFBHQ2 or ST650ACY5F14IN (Quenched 5'-nuclease probe) | 0.1-0.2 μM (10-20 pmol/rx) |
| UNG (Uracil N-Glycosylase) | 10 U/reaction |
| ZO5 DNA polymerase | 40 U/reaction |
| Mn(OAc)$_2$ | 3 mM |
| Light emission modifier | 0-50 μg/mL |
| HCV TARGET DNA | 2-10$^6$ copies per reaction |

TABLE XI

Reaction Mixture for HIV PCR Using a Single-Labeled Fluorescent Probe

| Component | Concentration |
| --- | --- |
| poly rA carrier | 9 μg/mL |
| Glycerol | 6.2% |
| DMSO | 7.5% |
| Tricine, pH 8.3 | 50 mM |
| KOAc | 100 mM |
| dATP | 300 μM each |
| dCTP | |
| dGTP | |
| dUTP | 550 μM |
| SK145BU (amplification primer) | 0.4 μM (40 pmol/rx) |
| GAG152BU (amplification primer) | 0.4 μM (40 pmol/rx) |
| GAG108AF (single-labeled fluorescent probe) | 0.1 μM |
| UNG (Uracil N-Glycosylase) | 10 U/reaction |
| ZO5 DNA polymerase | 40 U/reaction |
| Mn(OAc)$_2$ | 3 mM |

TABLE XI-continued

Reaction Mixture for HIV PCR Using a Single-Labeled Fluorescent Probe

| Component | Concentration |
| --- | --- |
| Light emission modifier | 0-50 μg/mL |
| HIV target DNA | 2-10$^6$ copies per reaction |

TABLE XII

Reaction mixture for HCV RT-PCR using a single-labeled fluorescent probe

| Component | Concentration |
| --- | --- |
| poly rA carrier | 9 μg/mL |
| Glycerol | 6.2% |
| DMSO | 7.5% |
| Tricine, pH 8.3 | 50 mM |
| KOAc | 100 mM |
| dATP | 300 μM each |
| dCTP | |
| dGTP | |
| dUTP | 550 μM |
| ST280ATBUA1 amplification primer | 0.4 μM (40 pmol/rx) |
| ST778AATBA1 amplification primer | 0.4 μM (40 pmol/rx) |
| ST650AAFBHQ2 Or ST650ACY5F14IN Quenched 5'-nuclease Probe | 0.1-0.2 μM (10-20 pmol/rx) |
| UNG (Uracil N-Glycosylase) | 10 U/reaction |
| ZO5 DNA polymerase | 40 U/reaction |
| Mn(OAc)$_2$ | 3 mM |
| Light emission modifier | 0-50 μg/mL |
| HCV TARGET RNA | 2-10$^6$ copies per reaction |

TABLE XIII

Reaction mixture for HIV RT-PCR using a single-labeled fluorescent probe

| Component | Concentration |
| --- | --- |
| poly rA carrier | 9 μg/mL |
| Glycerol | 6.2% |
| DMSO | 7.5% |
| Tricine, pH 8.3 | 50 mM |
| KOAc | 100 mM |
| dATP | 300 μM each |
| dCTP | |
| dGTP | |
| dUTP | 550 μM |
| SK145BU (amplification primer) | 0.4 μM (40 pmol/rx) |
| GAG152BU (amplification primer) | 0.4 μM (40 pmol/rx) |
| GAG108AF (single-labeled fluorescent probe) | 0.1 μM |
| UNG (Uracil N-Glycosylase) | 10 U/reaction |
| ZO5 DNA polymerase | 40 U/reaction |
| Mn(OAc)$_2$ | 3 mM |
| Light emission modifier | 0-50 μg/mL |
| HIV target RNA | 2-10$^6$ copies per reaction |

Thermocycling Conditions

TABLE XIV

HCV and QS PCR

Thermocycling

| | | |
|---|---|---|
| Stage 1 | 50° C./5 m | |
| Stage 2 | 95° C./2 m | |
| Stage 3 | 95° C./15 s | |
| ↓ | | 2 cycles |
| | 58° C./50 s | |
| Stage 4 | 95° C./15 s | |
| ↓ | | 60 cycles |
| | 50-58° C./50 s | |
| Stage 5 | 4° C./inf. | |

TABLE XV

HCV RT-PCR

Thermocycling

| | | |
|---|---|---|
| Stage 1 | 50° C./5 m | |
| Stage 2 | 59° C./30 m | |
| Stage 3 | 95° C./2 m | |
| Stage 4 | 95° C./15 s | |
| ↓ | | 2 cycles |
| | 50-58° C./50 s | |
| Stage 5 | 95° C./15 s | |
| ↓ | | 60 cycles |
| | 58° C./50 s | |
| Stage 6 | 4° C./inf. | |

TABLE XVI

HIV PCR

Thermocycling

| | | |
|---|---|---|
| Stage 1 | 50° C./5 m | |
| Stage 2 | 95° C./2 m | |
| Stage 3 | 95° C./15 s | |
| ↓ | | 2 cycles |
| | 58° C./50 s | |
| Stage 4 | 91° C./15 s | |
| ↓ | | 60 cycles |
| | 50-58° C./50 s | |
| Stage 5 | 4° C./inf. | |

TABLE XVII

HIV RT-PCR

Thermocycling

| | | |
|---|---|---|
| Stage 1 | 50° C./5 m | |
| Stage 2 | 59° C./30 m | |
| Stage 3 | 95° C./2 m | |
| Stage 4 | 95° C./15 s | |
| ↓ | | 2 cycles |
| | 50-58° C./50 s | |
| Stage 5 | 91° C./15 s | |
| ↓ | | 60 cycles |
| | 58° C./50 s | |
| Stage 6 | 4° C./inf. | |

Example 2

Single-Labeled Probes

Fluorescence Quenching

This Example and Examples that follow illustrate various performance characteristics of assays that included the use of light emission modifiers described herein and assorted single-labeled probes. This example illustrates the quenching of fluorescence with various light emission modifiers of the invention.

Figure 4:
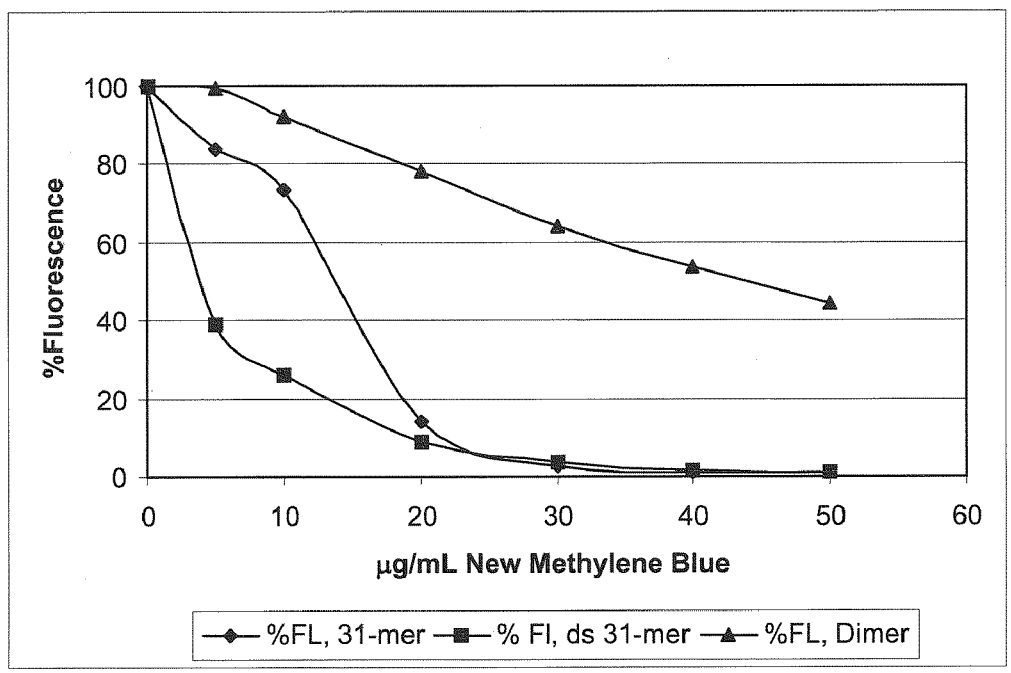
FIG. 4 is a graph (ordinate represents percent fluorescence, abscissa represents the new methylene blue concentration (µg/mL)) that shows fluorescence quenching of single-stranded (ss) and double-stranded (ds) DNA and thymidine dimer with increasing amounts of new methylene blue in separate reverse transcription-polymerase chain (RT-PCR) mixtures.

FIG. 4 is a graph (ordinate represents percent fluorescence, abscissa represents concentration (μg/mL)) that shows the quenching of fluorescence from different single-labeled nucleic acids with various concentrations of new methylene blue. As shown in the legend that accompanies the graph, the plots are for a single-labeled, single-stranded oligonucleotide having a sequence of 31 nucleotides (i.e., a 31-mer (GAG108AF; ETCTGCAGCTTCCTCATTGATGG-TATCTTTTAP, where E=FAM and P=phosphate (SEQ ID NO: 13))), a single-labeled, double-stranded 31-mer, and a single-labeled dinucleotide or dimer at the indicated new methylene blue concentrations. Each of these nucleic acids included a 5'-end FAM label.

Figure 5:
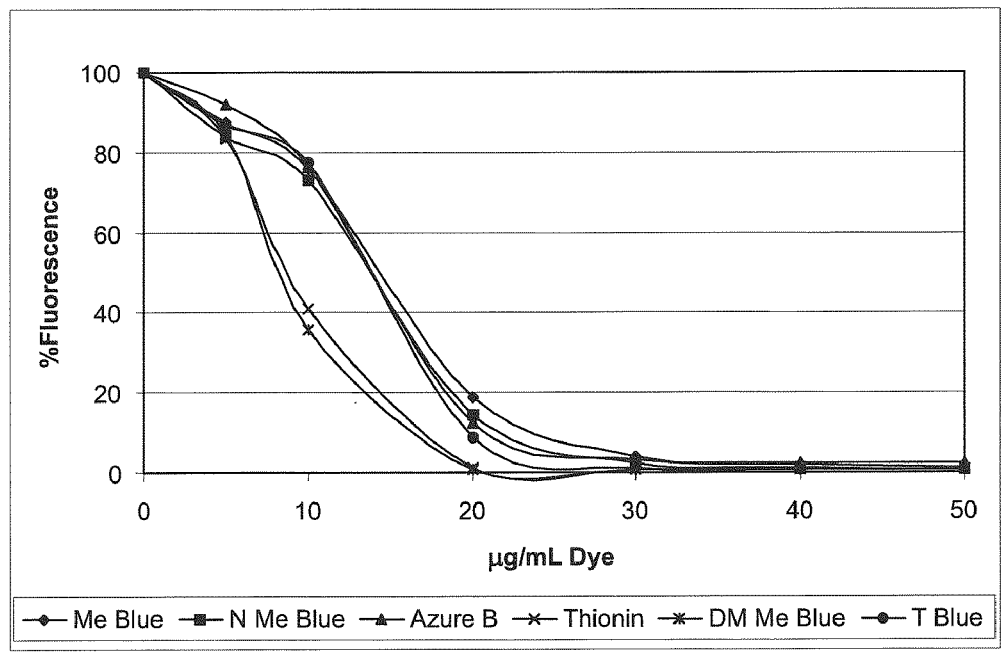
FIG. 5 is a graph (ordinate represents percent fluorescence, abscissa represents light emission modifier concentration (µg/mL)) that shows fluorescence quenching of ss DNA with increasing amounts of six different thiazine dyes in a cocktail containing all the components of an RT-PCR mixture.

FIG. 5 is a graph (ordinate represents percent fluorescence, abscissa represents light emission modifier concentration (μg/mL)) that shows the quenching of fluorescence using various light emission modifiers performed in separate analyses. Single-stranded 31-mers comprising 5'-end FAM labels were used in these analyses (i.e., GAG108AF, above). As shown in the legend accompanying the plot, the different light emission modifiers utilized were methylene blue (Me Blue), new methylene blue (N Me Blue), azure B, thionin, dimethyl methylene blue (DM Me Blue), and toluidine blue (T Blue).

Figure 6:
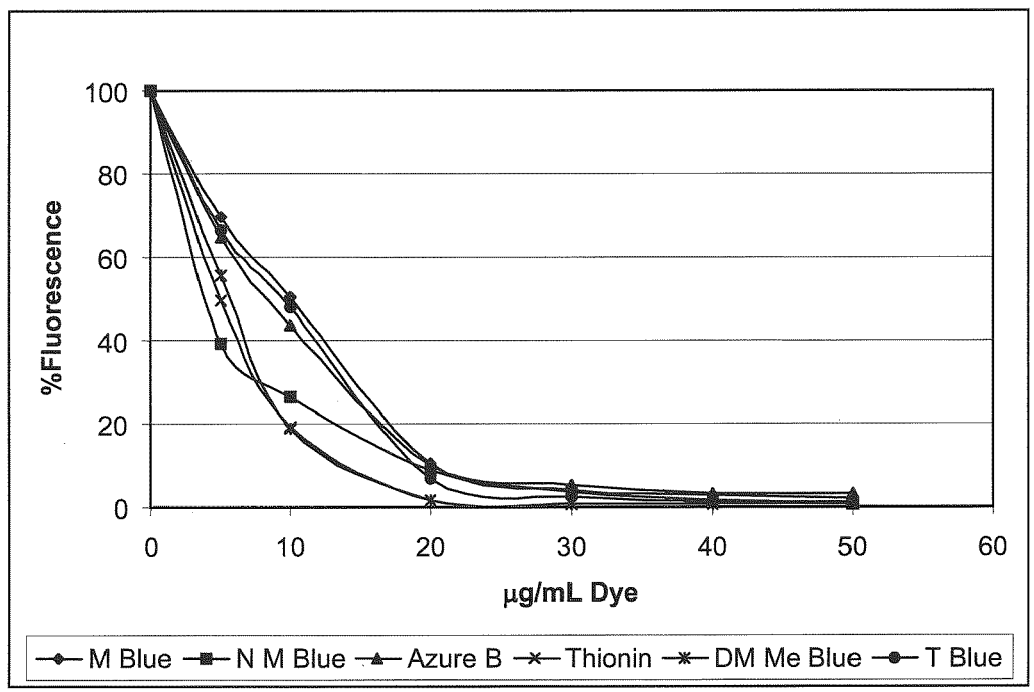
FIG. 6 is a graph (ordinate represents percent fluorescence, abscissa represents light emission modifier concentration (µg/mL)) that shows fluorescence quenching of ds DNA with increasing amounts of six different thiazine dyes in a cocktail containing all the components of an RT-PCR mixture.

FIG. 6 is a graph (ordinate represents percent fluorescence, abscissa represents light emission modifier concentration (μg/mL)) that shows the quenching of fluorescence from single-labeled, double-stranded oligonucleotides with various light emission modifiers. That is, the 5'-ends of one strand of the double-stranded 31-mers used in these separate analyses were labeled with FAM. As shown in the legend accompanying the plot, the different light emission modifiers utilized were methylene blue (Me Blue), new methylene blue (N Me Blue), azure B, thionin, dimethyl methylene blue (DM Me Blue), and toluidine blue (T Blue).

Figure 7:
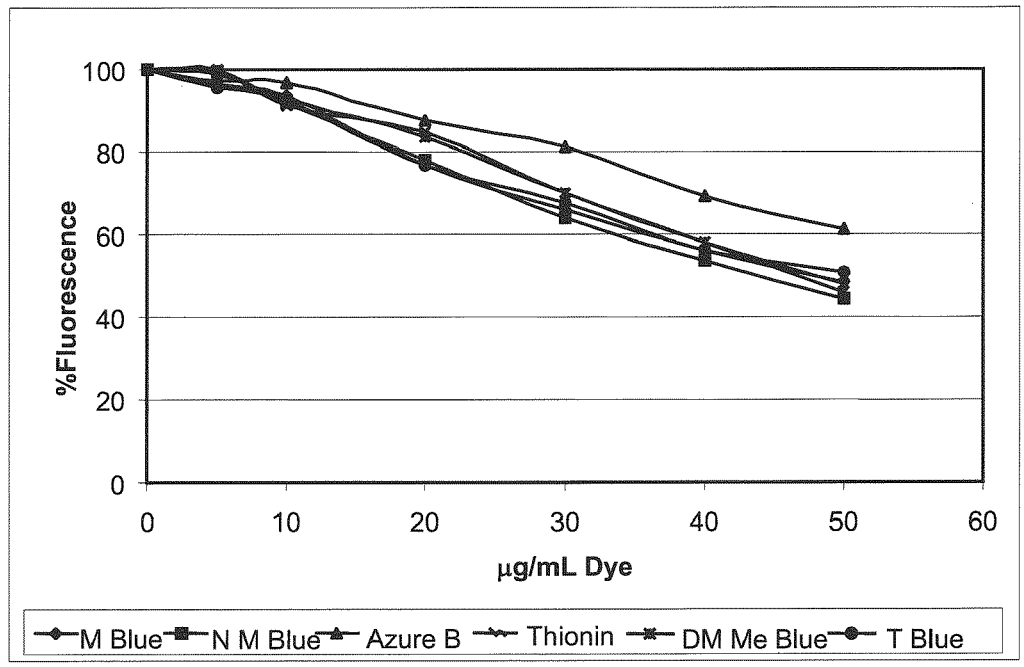
FIG. 7 is a graph (ordinate represents percent fluorescence, abscissa represents light emission modifier concentration (µg/mL)) that shows fluorescence quenching of dinucleotide DNA with increasing amounts of six different thiazine dyes in a cocktail containing all the components of an RT-PCR mixture.

FIG. 7 is a graph (ordinate represents percent fluorescence, abscissa represents light emission modifier concentration (μg/mL)) that shows the quenching of fluorescence from labeled dinucleotides (thymidine dimers (TT)) with various light emission modifiers. The dinucleotide used in these analyses was labeled at 5'-ends with FAM (i.e., 6-carboxy-fluorescein). As shown in the legend accompanying the plot, the different light emission modifiers utilized were methylene blue (Me Blue), new methylene blue (N Me Blue), azure B, thionin, dimethyl methylene blue (DM Me Blue), and toluidine blue (T Blue).

Figure 8:
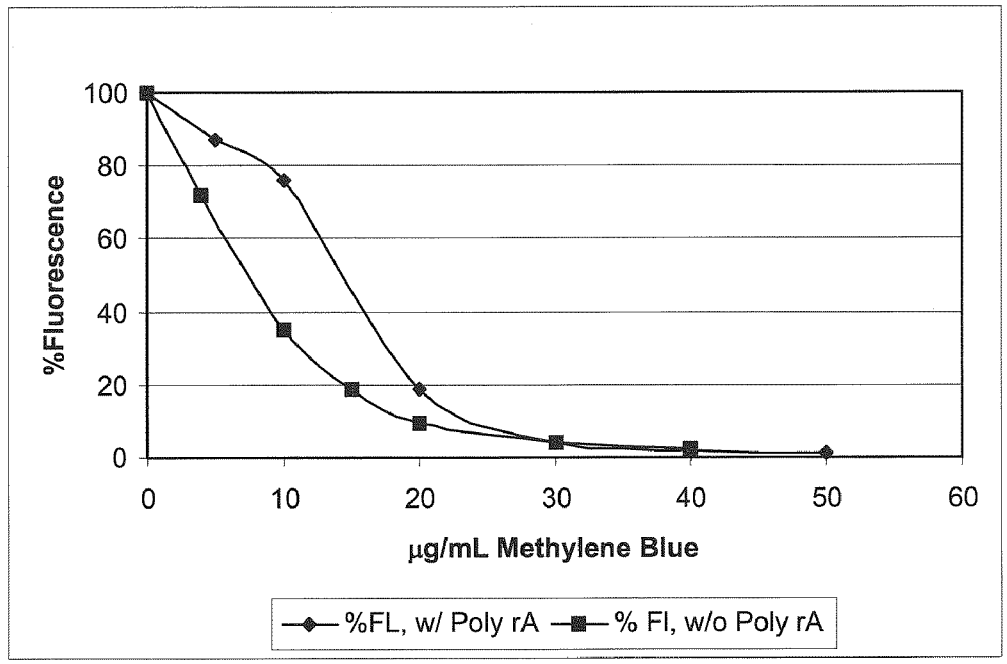
FIG. 8 is a graph (ordinate represents percent fluorescence, abscissa represents light emission modifier concentration (µg/mL)) that shows fluorescence quenching of ss DNA with increasing amounts of methylene blue in a cocktail containing all the components of an RT-PCR mixture, with or without poly rA.

FIG. 8 is a graph (ordinate represents percent fluorescence, abscissa represents light emission modifier concentration (μg/mL)) that shows the quenching of fluorescence from labeled, single-stranded oligonucleotides with methylene blue under various conditions. Single-stranded 31-mers comprising 5'-end FAM labels were used in these analyses. As shown in the legend accompanying the plot, the reaction mixtures represented by one trace included poly rA, whereas the reaction mixtures represented by the other trace lacked poly rA. Poly rA is adenosine homopolymer that is generally used as a component of a sample diluent buffer. It serves as a carrier nucleic acid, and improves the sensitivity of the assays by minimizing losses of target nucleic acids after sample preparation. Poly rA is typically used at a relatively high concentration. The analysis illustrated in FIG. 8 evaluated whether poly rA interferes with the effectiveness of a soluble quencher, e.g., by binding to it and making it less available.

Example 3

Polymerase Chain Reactions Using Single Label Probes and Azure Dyes

This example illustrates the embodiment describing real time detection with a single-labeled probe and a light emission modifier of the invention.

Figure 9:
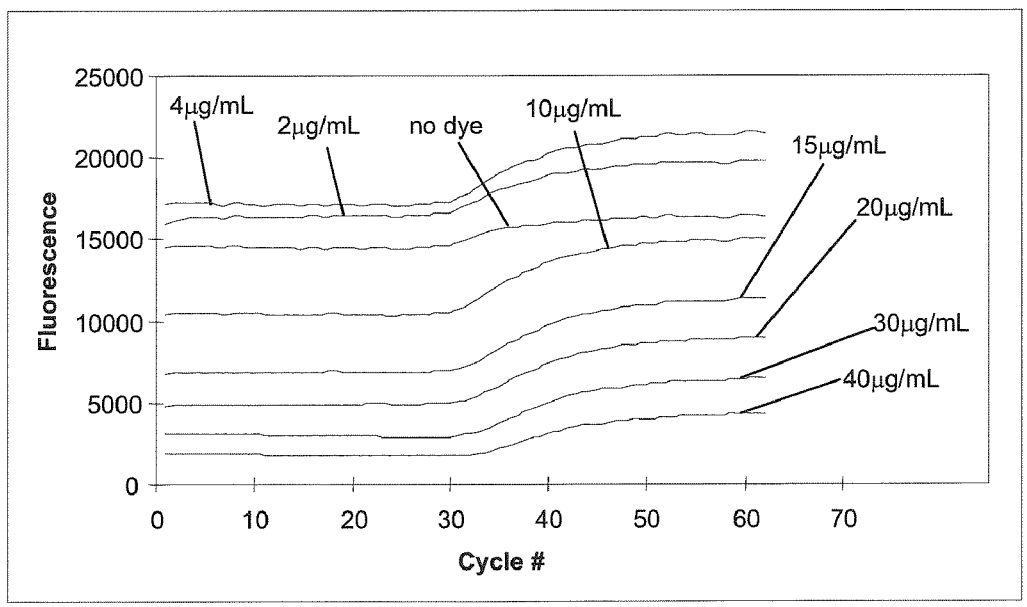
FIG. 9 is an amplification plot (ordinate represents absolute fluorescence, abscissa represents the cycle number) that shows polymerase chain reaction (PCR) detection of hepatitis C virus (HCV) DNA with a single-labeled HCV probe in the presence of various concentrations of azure B.
Figure 11:
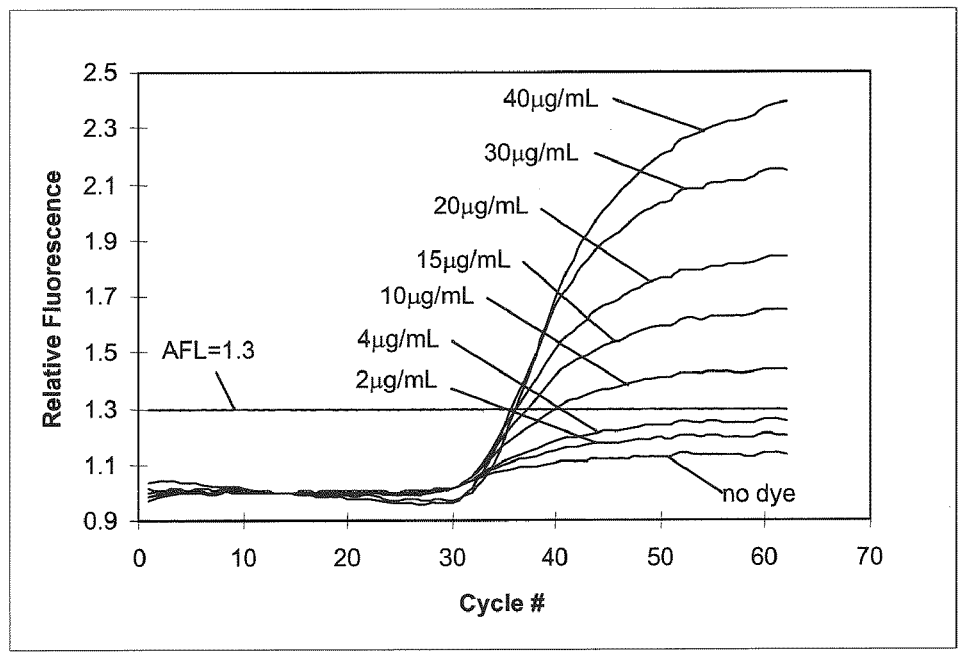
FIG. 11 is an amplification plot (ordinate represents relative fluorescence, abscissa represents the cycle number) that shows PCR detection of HCV DNA with a single-labeled probe in the presence of various concentrations of azure B.

FIG. 9 is an amplification plot (ordinate represents absolute fluorescence, abscissa represents the cycle number) that shows data obtained from various 5'-nuclease reactions that included single-labeled 5'-nuclease probes and various concentrations of azure B in HCV detection assays. The single-labeled ST650 probes (corresponding to SEQ ID NO: 5) used in the reaction mixtures represented by these traces were labeled at 5'-ends with FAM. The reaction mixtures also included poly rA. The labels accompanying the traces show the concentration of azure B used in each of these reaction mixtures. The relative fluorescence as a function of light emission modifier concentration for these reactions is plotted in FIG. 11. This plot shows, e.g., that relative fluorescence increases with increasing light emission modifier concentration.

Figure 10:
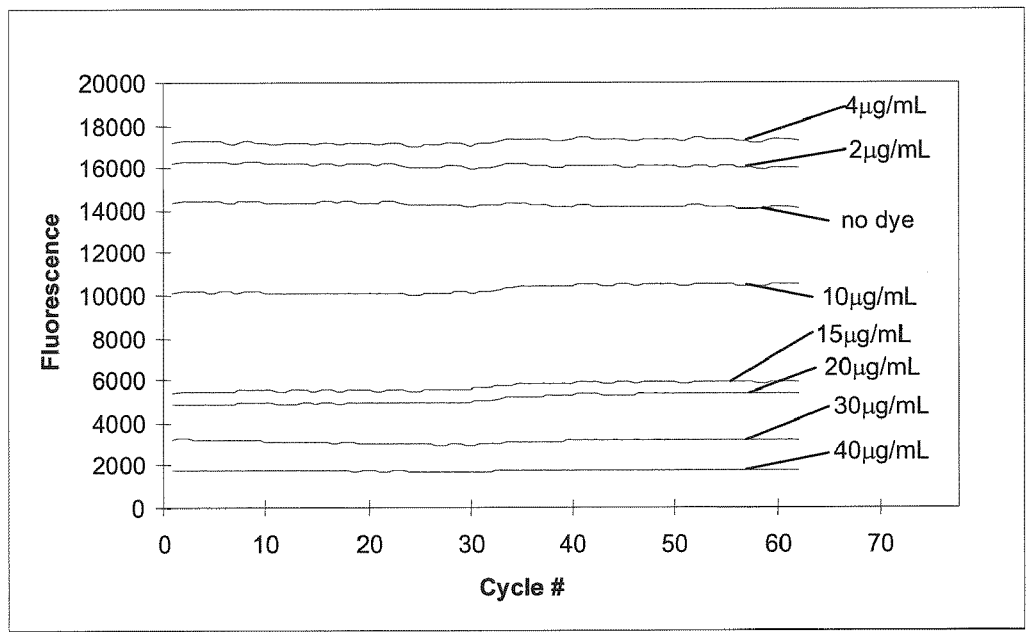
FIG. 10 is an amplification plot (ordinate represents absolute fluorescence, abscissa represents the cycle number) that shows fluorescence as a function of cycle number using a single-labeled HCV probe in human immunodeficiency virus (HIV) kinetic PCR reactions in the presence of various concentrations of azure B.

FIG. 10 is an amplification plot (ordinate represents absolute fluorescence, abscissa represents the cycle number) that shows data obtained from various 5'-nuclease reactions that included single-labeled 5'-nuclease probes and various concentrations of azure B in HIV detection assays. The single-labeled ST650 probes (corresponding to SEQ ID NO: 5) used in the reaction mixtures represented by these traces were labeled at 5'-ends with FAM. The reaction mixtures also included poly rA. The labels accompanying the traces show the concentration of azure B used in each of these reaction mixtures. As shown, when the HCV probe was used in an HIV amplification system, the probe was not cleaved and no growth curves were observed. This analysis showed the observed growth curve to be specific to probe hydrolysis and not due to the partitioning of the soluble quencher into the amplicon.

Example 4

Polymerase Chain Reactions Using Single Label Probes and New Methylene Blue

Figure 12:
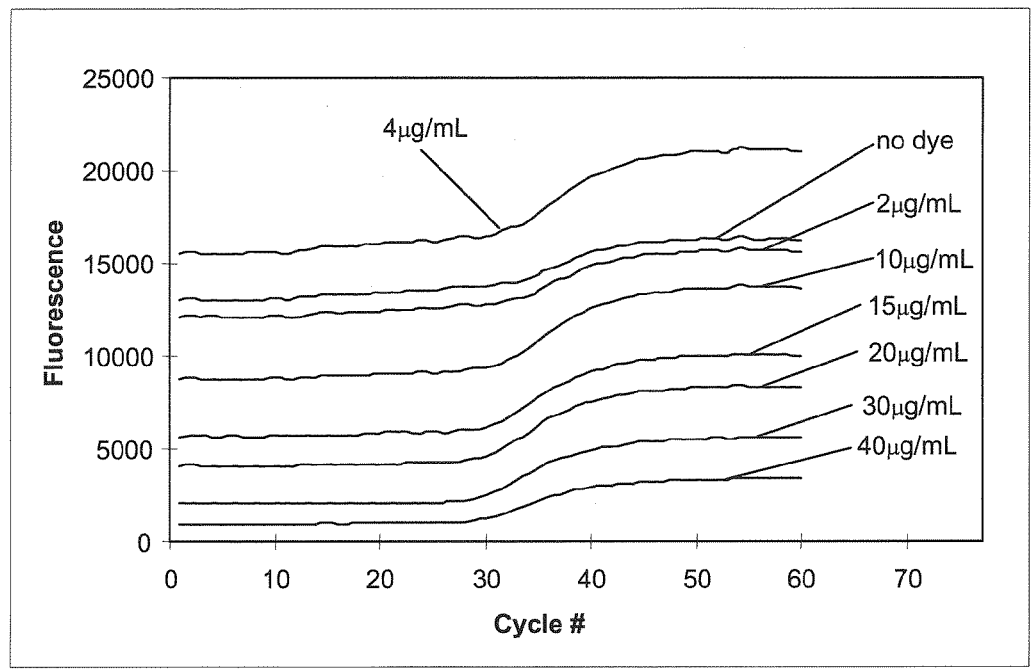
FIG. 12 is an amplification plot (ordinate represents absolute fluorescence, abscissa represents the cycle number) that shows PCR detection of HCV DNA with a single-labeled probe in the presence of various concentrations of new methylene blue.
Figure 13:
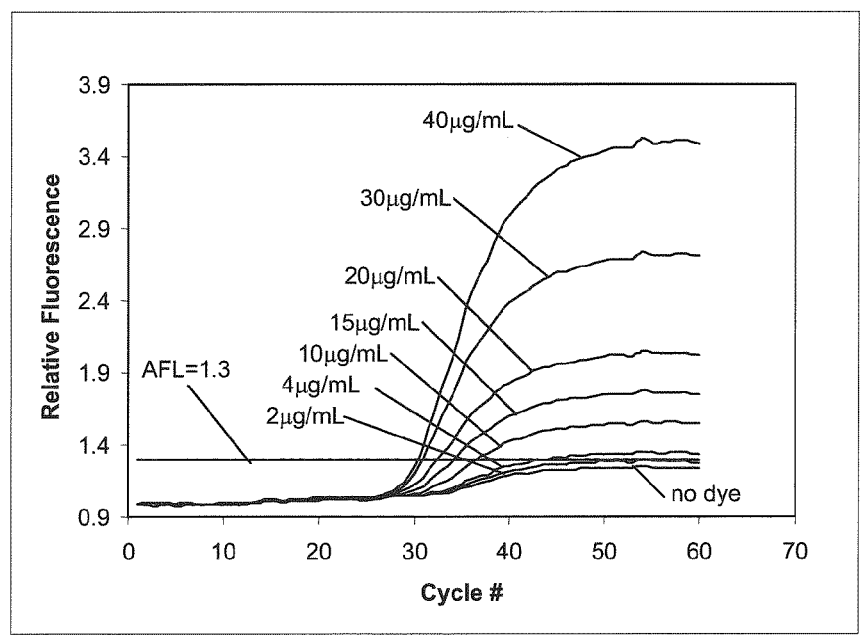
FIG. 13 is an amplification plot (ordinate represents relative fluorescence, abscissa represents the cycle number) that shows PCR detection of HCV DNA with a single-labeled probe in the presence of various concentrations of new methylene blue.

FIG. 12 is an amplification plot (ordinate represents absolute fluorescence, abscissa represents the cycle number) that shows data obtained from various 5'-nuclease reactions that included single-labeled nuclease probes and new methylene blue in HCV detection assays. The single-labeled ST650 probes (corresponding to SEQ ID NO: 5) used in these reaction mixtures were labeled at 5'-ends with FAM. In addition, the reaction mixtures represented by these traces included poly rA and the denaturing temperature ($T_{den}$) used in these reactions was 95° C. 20,000 copies of HCV cDNA were present in each reaction mixture. The annealing temperature used in these reactions was 58° C. The new methylene blue concentrations used in these reaction mixtures are indicated by the labels that accompany the plot. The amplification plot of FIG. 13 shows the relative fluorescence for this data.

Example 5

Figure 14:
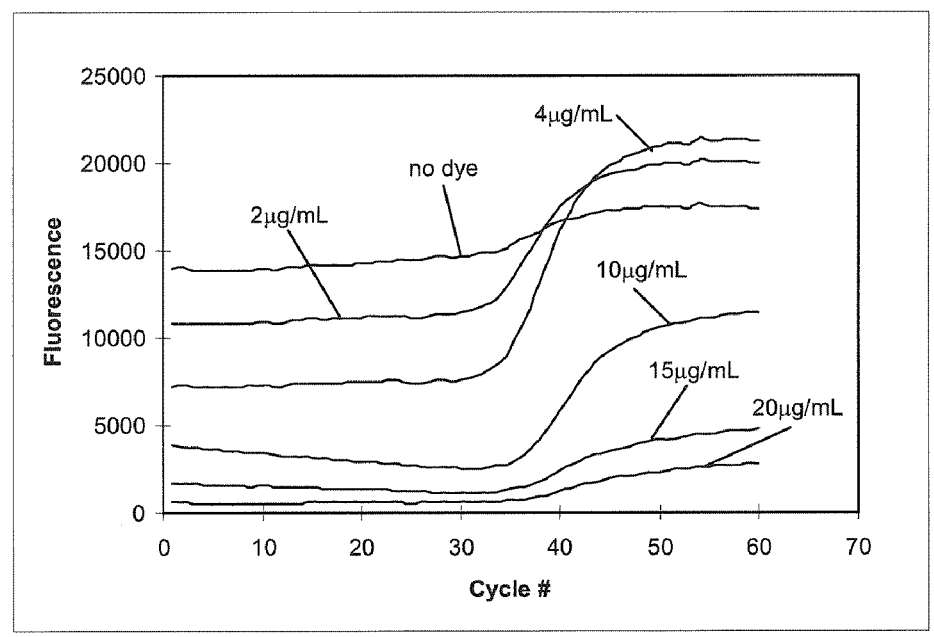
FIG. 14 is an amplification plot (ordinate represents absolute fluorescence, abscissa represents the cycle number) that shows PCR detection of HCV DNA with a single-labeled probe in the presence of various concentrations of 1,9 dimethyl methylene blue.
Figure 15:
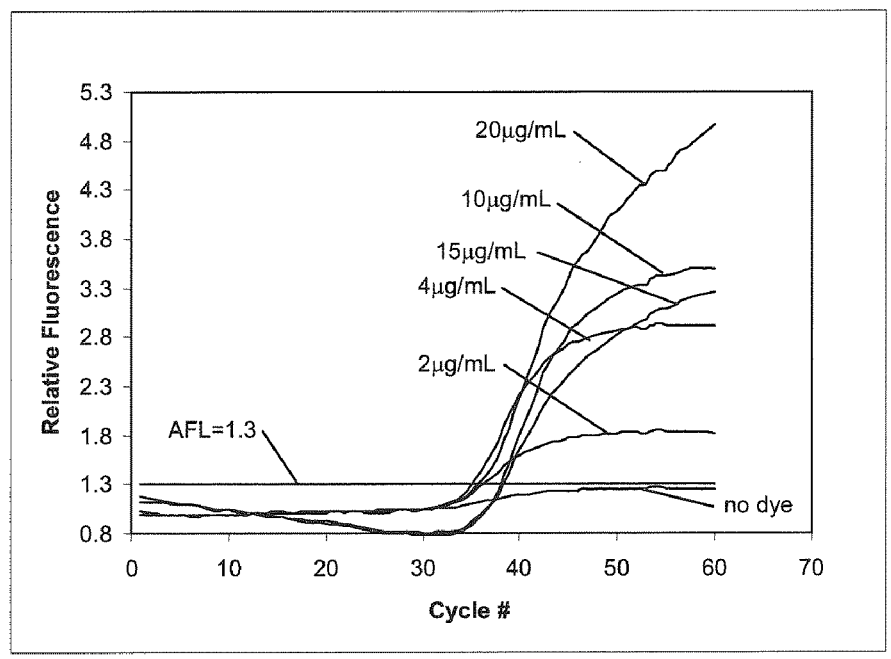
FIG. 15 is an amplification plot (ordinate represents relative fluorescence, abscissa represents the cycle number) that shows PCR detection of HCV DNA with a single-labeled probe in the presence of various concentrations of 1,9 dimethyl methylene blue.

Polymerase Chain Reactions Using Double Label Probes and 1,9-Demethyl Methylene Blue FIG. 14 is an amplification plot (ordinate represents absolute fluorescence, abscissa represents the cycle number) that shows data obtained from various 5'-nuclease reactions that included dual-labeled 5'-nuclease probes and 1,9-dimethyl methylene blue in HCV detection assays. The dual-labeled ST650 probes (corresponding to SEQ ID NO: 5) used in these reaction mixtures were labeled with FAM and a BHQ™. In addition, the reaction mixtures represented by these traces included poly rA and the $T_{den}$ used in these reactions was 95° C. 20,000 copies of HCV cDNA were present in each reaction mixture. The annealing temperature used in these reactions was 58° C. The new methylene blue concentrations used in these reaction mixtures are indicated in the labels that accompany the plot. The amplification plot of FIG. 15 shows the relative fluorescence for this data.

Example 6

Polymerase Chain Reactions Using Single Label Probes and Azure A and C

Figure 16:
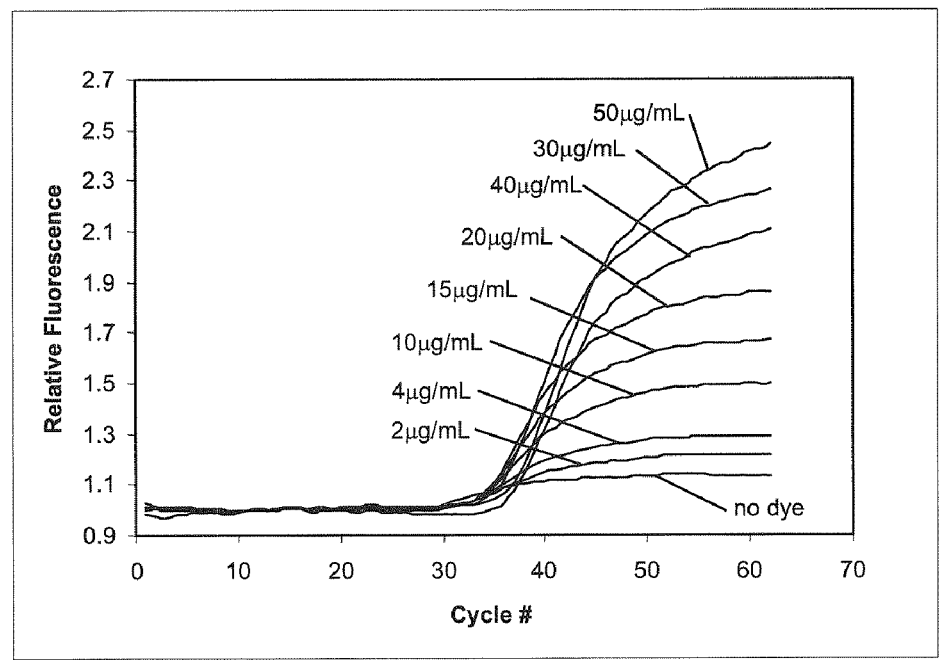
FIG. 16 is an amplification plot (ordinate represents relative fluorescence, abscissa represents the cycle number) that shows PCR detection of HCV DNA with a single-labeled probe in the presence of various concentrations of azure A.

FIG. 16 is an amplification plot (ordinate represents relative fluorescence, abscissa represents the cycle number) that shows data obtained from various 5'-nuclease reactions that included single-labeled 5'-nuclease probes and azure A in HCV detection assays. The single-labeled ST650 probes (corresponding to SEQ ID NO: 5) used in these reaction mixtures were labeled at 5'-ends with FAM. Further, the reaction mixtures represented by these traces included poly rA and the $T_{den}$ used in these reactions was 95° C. 20,000 copies of HCV cDNA were present in each reaction mixture. The azure A concentrations used in these reaction mixtures are indicated in the labels that accompany the plot.

Figure 17:
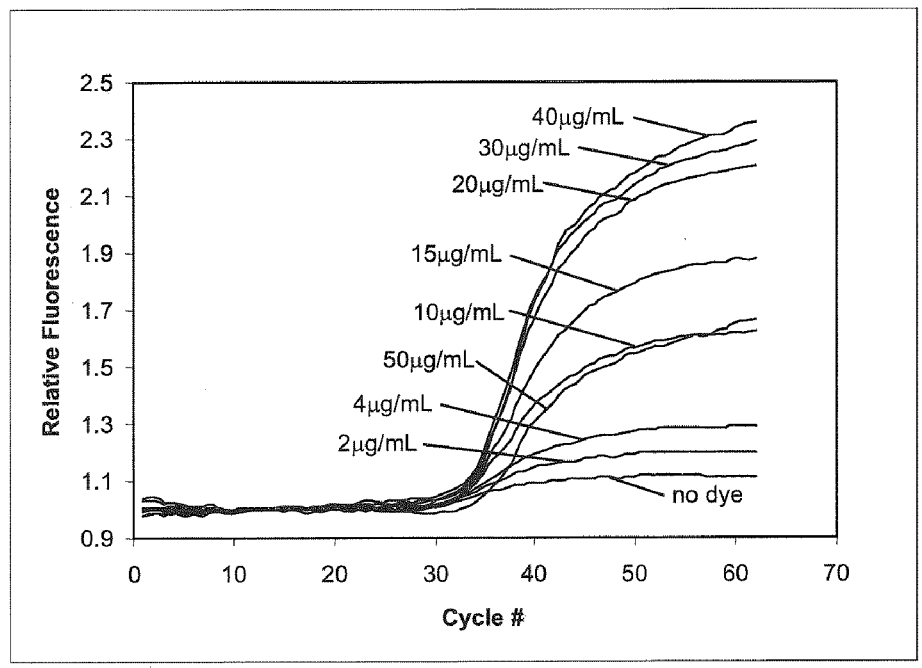
FIG. 17 is an amplification plot (ordinate represents relative fluorescence, abscissa represents the cycle number) that shows PCR detection of HCV DNA with a single-labeled probe in the presence of various concentrations of azure C.

FIG. 17 is an amplification plot (ordinate represents relative fluorescence, abscissa represents the cycle number) that shows data obtained from various 5'-nuclease reactions that included single-labeled nuclease probes and azure C in HCV detection assays. The single-labeled ST650 probes (corresponding to SEQ ID NO: 5) used in these reaction mixtures were labeled at 5'-ends with FAM. In addition, the reaction mixtures represented by these traces included poly rA and the $T_{den}$ used in these reactions was 95° C. 20,000 copies of HCV cDNA were present in each reaction mixture. The azure C concentrations used in these reaction mixtures are indicated in the labels that accompany the plot.

Example 7

Polymerase Chain Reactions Using Single Label Probes and Thionin

Figure 18:
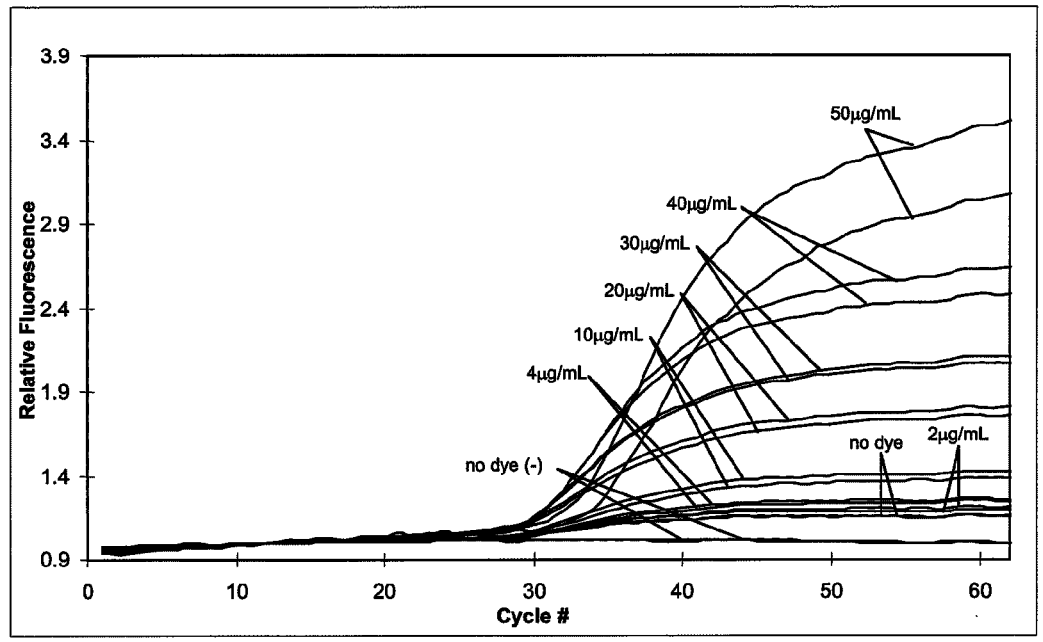
FIG. 18 is an amplification plot (ordinate represents relative fluorescence, abscissa represents the cycle number) that shows PCR detection of HCV DNA with a single-labeled probe in the presence of various concentrations of thionin.

FIG. 18 is an amplification plot (ordinate represents relative fluorescence, abscissa represents the cycle number) that shows data obtained from various 5'-nuclease reactions that included single-labeled nuclease probes and thionin in HCV detection assays. The single-labeled ST650 probes (corresponding to SEQ ID NO: 5) used in these reaction mixtures were labeled at 5'-ends with FAM. Further, the reaction mixtures represented by these traces included poly rA and the $T_{den}$ used in these reactions was 95° C. 20,000 copies of HCV cDNA were present in each reaction mixture. The thionin concentrations used in these reaction mixtures are indicated in the labels that accompany the plot.

Example 8

Polymerase Chain Reactions Using Single Label Probes and Methylene Green

Figure 19:
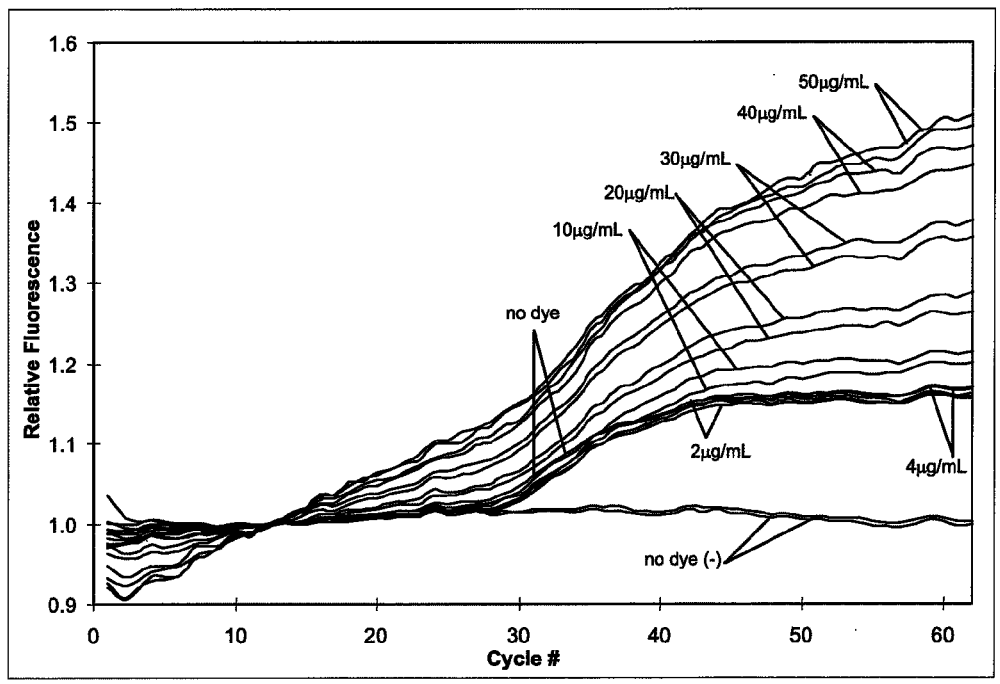
FIG. 19 is an amplification plot (ordinate represents relative fluorescence, abscissa represents the cycle number) that shows PCR detection of HCV DNA with a single-labeled probe in the presence of various concentrations of methylene green.

FIG. 19 is an amplification plot (ordinate represents relative fluorescence, abscissa represents the cycle number) that shows data obtained from various 5'-nuclease reactions that included single-labeled 5'-nuclease probes and methylene green in HCV detection assays. The single-labeled ST650 probes (corresponding to SEQ ID NO: 5) used in these reaction mixtures were labeled at 5'-ends with FAM. In addition, the reaction mixtures represented by these traces included poly rA and the $T_{der}$ used in these reactions was 95° C. 20,000 copies of HCV cDNA were present in each reaction mixture. The methylene green concentrations used in these reaction mixtures are indicated in the labels that accompany the plot.

Example 9

Figure 20:
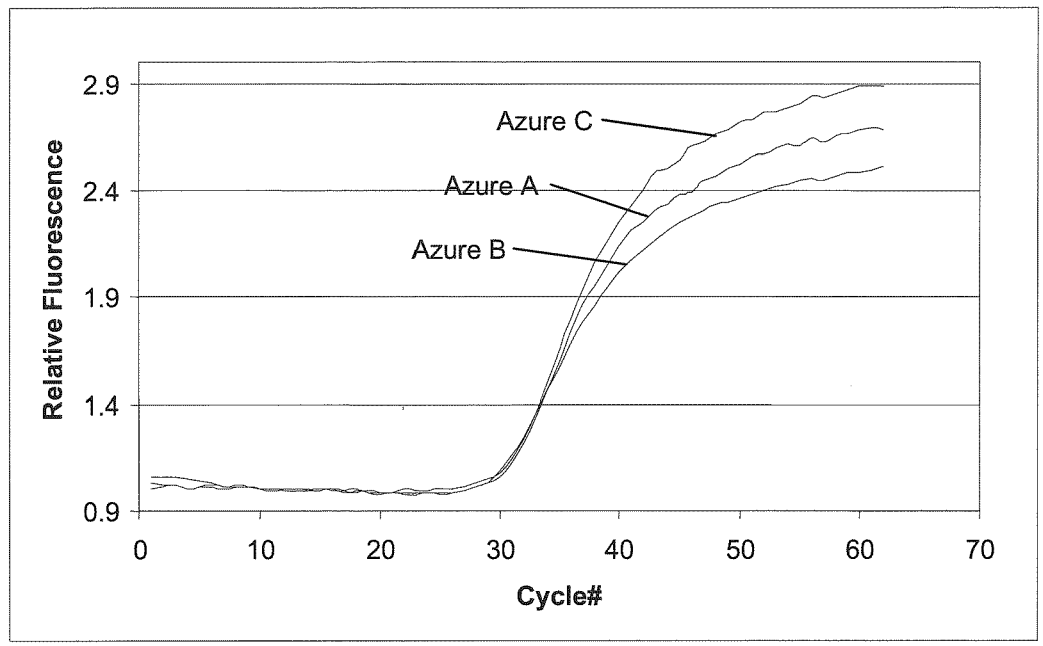
FIG. 20 is an amplification plot (ordinate represents relative fluorescence, abscissa represents the cycle number) that shows a comparison of azure A, azure B, and azure C in the PCR detection of HCV DNA with a single-labeled probe in the presence of 40 µg/mL concentrations of the azure dye.

Polymerase Chain Reactions Using Single Label Probes and Various Light Emission Modifiers FIG. 20 is an amplification plot (ordinate represents relative fluorescence, abscissa represents the cycle number) that shows data obtained from various 5'-nuclease reactions that included single-labeled 5'-nuclease probes and different azure dyes in HCV detection assays. The single-labeled ST650 probes (corresponding to SEQ ID NO: 5) used in these reaction mixtures were labeled at 5'-ends with FAM. The reaction mixtures represented by these traces included poly rA and 200,000 copies of a target nucleic acid from HCV. The $T_{den}$ used in these reactions was 95° C. As shown in the labels that accompany the plot, the dyes used in these analyses were azure A, azure B, and azure C, which were each present in the respective reaction mixtures at a concentration of 40 µg/mL.

Figure 21:
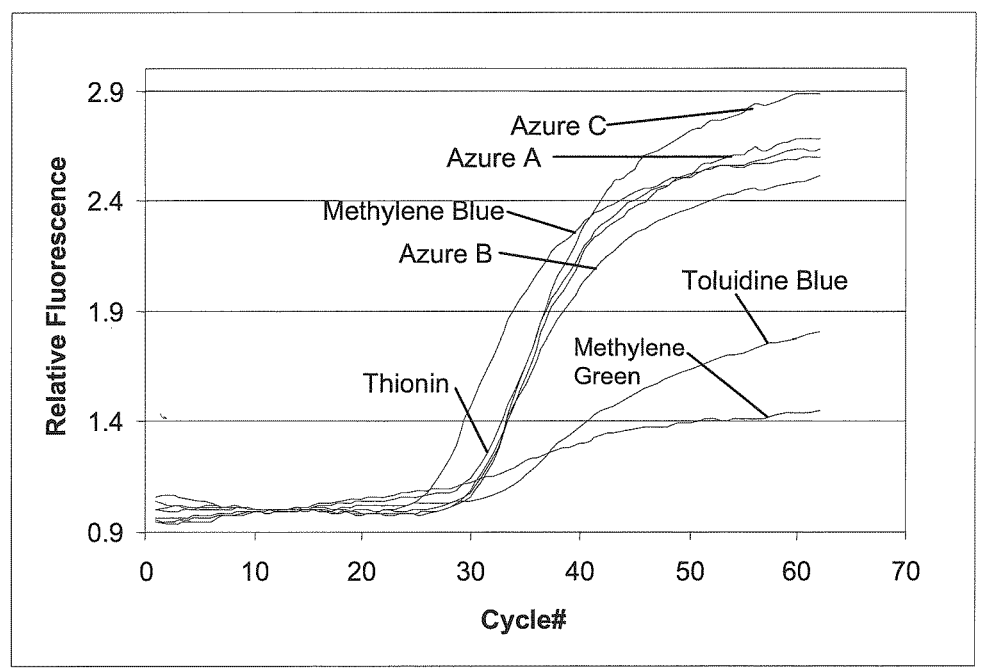
FIG. 21 is an amplification plot (ordinate represents relative fluorescence, abscissa represents the cycle number) that shows a comparison of azure A, azure B, azure C, methylene blue, toluidine blue, thionin, and methylene green in the PCR detection of HCV DNA with a single-labeled probe in the presence of 40 µg/mL concentrations of the thiazine dye.

FIG. 21 is an amplification plot (ordinate represents relative fluorescence, abscissa represents the cycle number) that shows data obtained from various 5'-nuclease reactions that included single-labeled 5'nuclease probes and various light emission modifiers in HCV detection assays. The single-labeled ST650 probes (corresponding to SEQ ID NO: 5) used in these reaction mixtures were labeled at 5'-ends with FAM. The reaction mixtures represented by these traces included poly rA and 200,000 copies of a target nucleic acid from HCV. The $T_{den}$ used in these reactions was 95° C. As shown in the labels that accompany the plot, the light emission modifiers used in these analyses were azure A, azure B, azure C, methylene blue, toluidine blue, thionin, and methylene green, which were each present in the respective reaction mixtures at a concentration of 40 µg/mL.

Example 10

Polymerase Chain Reactions Using Various Concentrations of Methylene Blue

FIG. 22 (panels A and B) is a photograph of a polyacrylamide gel analysis of PCR reactions with target HCV DNA, various probes, and various amounts of methylene blue. The numbers shown above the lanes in the gel indicate the concentrations (µg/mL) of methylene blue that were included in the particular reaction mixtures. Lanes denoted with 0(–) are those in which negative controls were run. The reaction mixtures included poly rA and 20,000 copies of the target HCV DNA. In addition, the $T_{den}$ used in these reactions was 95° C. As shown, the probes utilized were ST650_5'-FAM & ST2325_5'-HEX, dual ST650, and dual ST2535, which are described above. Panels A and B represent duplicate reactions. This analysis showed that PCR amplification is relatively unaffected by the presence of increasing amounts of the light emission modifier.

FIG. 23 is an amplification plot (ordinate represents relative fluorescence, abscissa represents the cycle number) that shows data obtained from various 5'-nuclease reactions that included single-labeled 5'-nuclease probes and methylene blue in QS-HCV detection assays. The single-labeled ST2535 probes (corresponding to SEQ ID NO: 12) used in these reaction mixtures were labeled at 5'-ends with HEX. The reaction mixtures represented by these traces included poly rA and the $T_{den}$ used in these reactions was 95° C. 20,000 copies of QS HCV cDNA were present in each reaction mixture. The methylene blue concentration used in these reaction mixtures was 40 µg/mL. The labels that accompany the plot indicate the concentration of methylene blue used in the reaction mixtures represented by each trace. This analysis demonstrated, e.g., the ability of thiazine dyes to quench different fluorophores (e.g., other than FAM).

Figure 24:
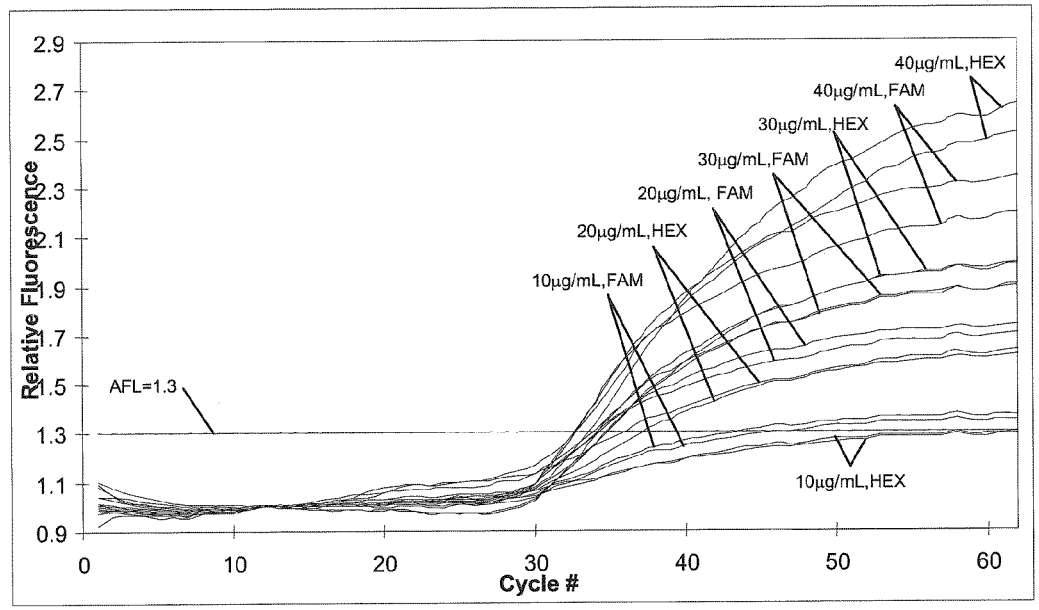
FIG. 24 is an amplification plot (ordinate represents relative fluorescence, abscissa represents the cycle number) that shows the simultaneous PCR detection of HCV and IQS DNA with a combination of FAM- and HEX-labeled single-labeled probes in the presence of various concentrations of methylene blue.

FIG. 24 is an amplification plot (ordinate represents relative fluorescence, abscissa represents the cycle number) that shows data obtained from various 5'-nuclease reactions that included multiple single-labeled nuclease probes and methylene blue in QS-HCV detection assays. The single-labeled probes used in these multiplexing analyses were 5'-FAM and 5'-HEX labeled oligonucleotides. The reaction mixtures represented by these traces included poly rA and the $T_{den}$ used in these reactions was 95° C. 20,000 copies of QS HCV cDNA were present in each reaction mixture. The methylene blue concentrations used in the reaction mixtures with these probe pairs is indicated in the labels that accompany the plot. This analysis illustrates the ability of thiazine dyes to be used in multiplex detection with single-labeled probes.

Example 11

Polymerase Chain Reactions Using Azure B

Figure 25:
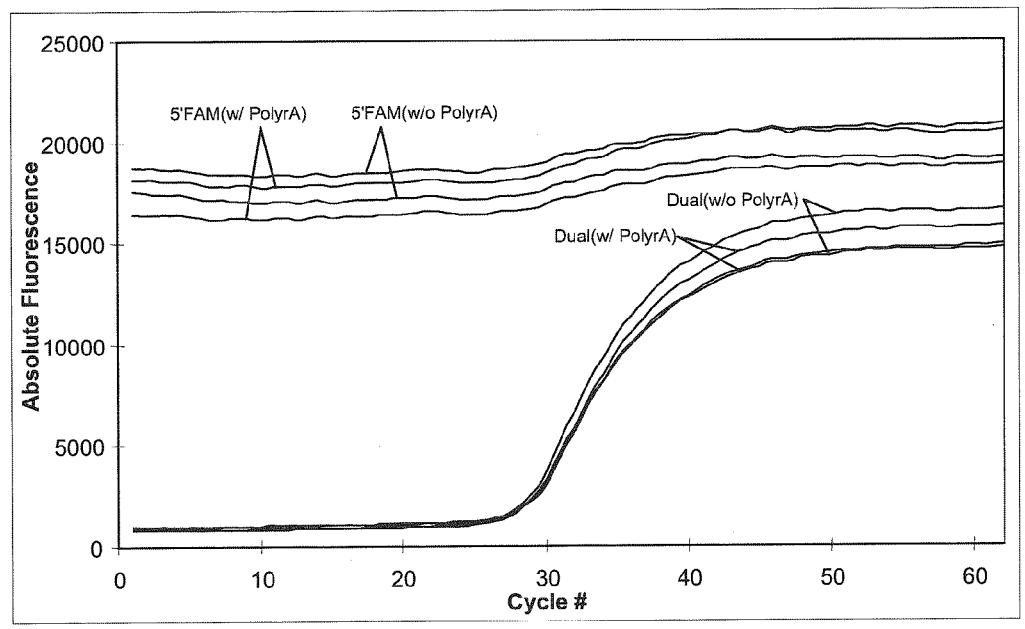
FIG. 25 is an amplification plot (ordinate represents absolute fluorescence, abscissa represents the cycle number) that shows a comparison of signals obtained from a single-labeled probe and a dual-labeled probe in the absence of a light emission modifier. The assays were performed either in the presence or in the absence of carrier nucleic acid, poly rA.

FIG. 25 is an amplification plot (ordinate represents absolute fluorescence, abscissa represents the cycle number) that shows data obtained from 5'-nuclease reactions performed in the absence of azure B in HCV detection assays. The reaction mixtures represented by these traces lacked azure B and included 20,000 copies of a target nucleic acid from HCV. The denaturing temperature ($T_{den}$) used in these reactions was 95° C. As shown in the accompanying trace labels, the reaction mixtures included either probes labeled at 5'-ends with FAM (i.e., 5'-FAM) or dual labeled probes (i.e., dual) and either included or lacked poly rA. As shown, there was a slight release of fluorescence from the unquenched single-labeled probe. This may have been due to some G-quenching in the probe. However, this signal increase is generally too insignificant to be useful in a practical assay. In contrast, the dual labeled probe generated a good signal. Further, in the presence of the soluble quencher, the single-labeled probe also generated a good signal (see, e.g., FIGS. 26 and 27, which are described below).

Figure 26:
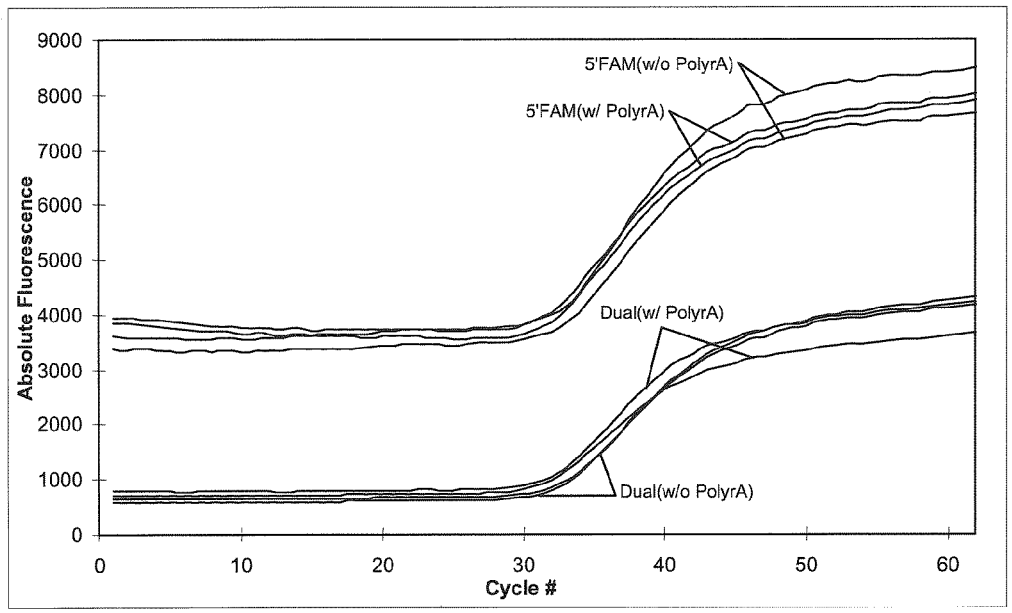
FIG. 26 is an amplification plot (ordinate represents absolute fluorescence, abscissa represents the cycle number) that shows a comparison of signals obtained from a single-labeled probe and a dual-labeled probe in the presence of 30 µg/mL of a light emission modifier, azure B. The assays were performed either in the presence or in the absence of carrier nucleic acid, poly rA.
Figure 27:
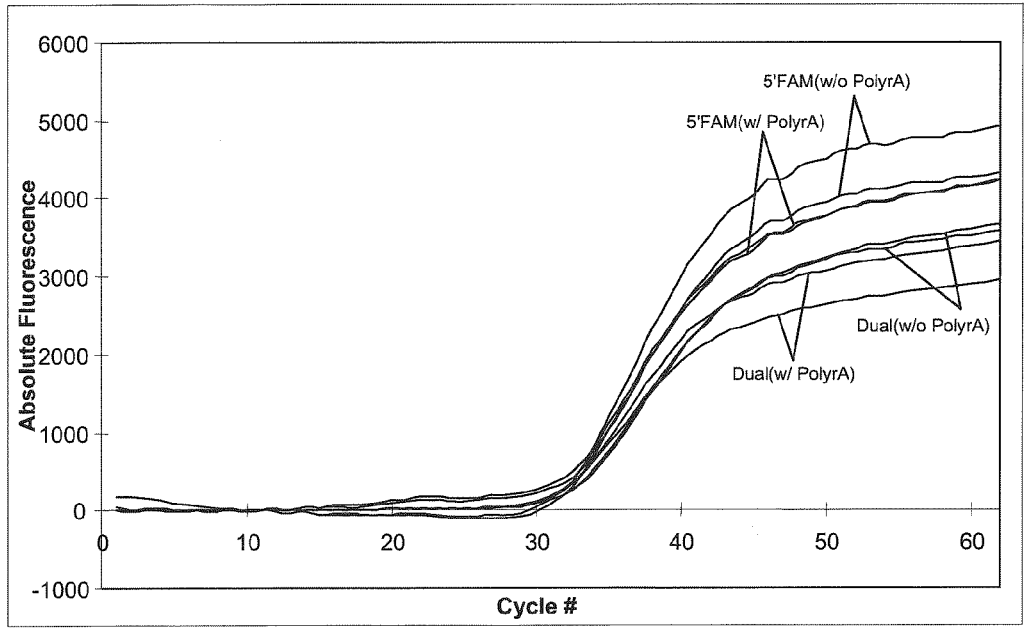
FIG. 27 is an amplification plot (ordinate represents absolute fluorescence, abscissa represents the cycle number) that shows a comparison of signals obtained from a single-labeled probe and a dual-labeled probe in the presence of 30 µg/mL of a light emission modifier, azure B. The assays were performed either in the presence or in the absence of carrier nucleic acid, poly rA.

FIGS. 26 and 27 are amplification plots (ordinate represents absolute fluorescence (FIG. 26), or normalized fluorescence (FIG. 27), abscissa represents the cycle number) that shows data obtained from various 5'-nuclease reactions that included azure B in HCV detection assays. The reaction mixtures represented by these traces included 30 µg/mL of azure B and 20,000 copies of a target nucleic acid from HCV. The $T_{den}$ used in these reactions was 95° C. As shown in the accompanying trace labels, the reaction mixtures included either probes labeled at 5'-ends with FAM (i.e., 5'-FAM) or dual labeled probes (i.e., dual) and either included or lacked poly rA.

Example 12

Additional Amplification Reactions Using Methylene Blue

Figure 28:
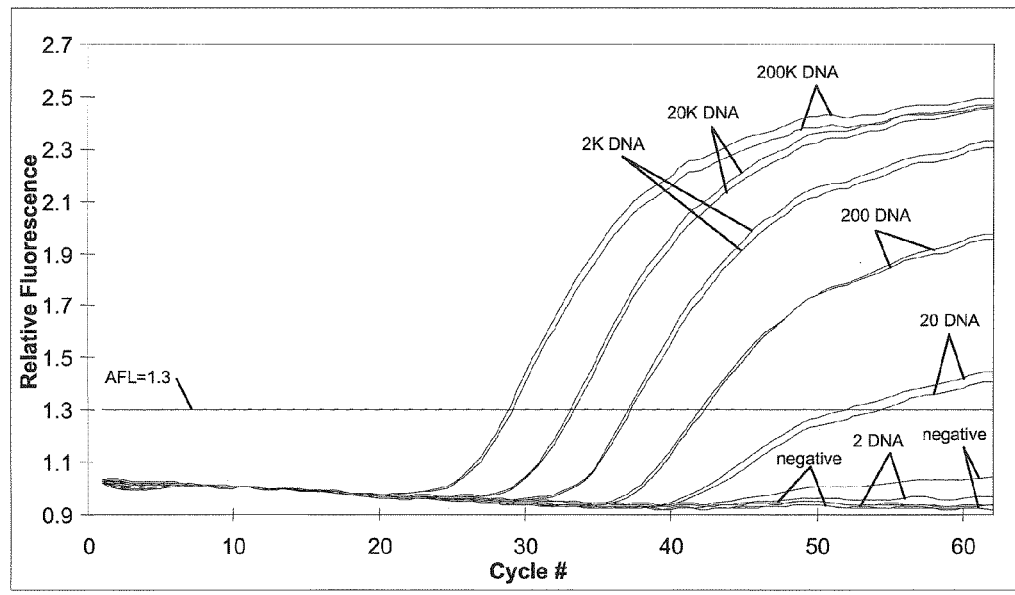
FIG. 28 is an amplification plot (ordinate represents relative fluorescence, abscissa represents the cycle number) that shows data obtained from DNA template titrations that included a single-labeled probe and methylene blue.
Figure 29:
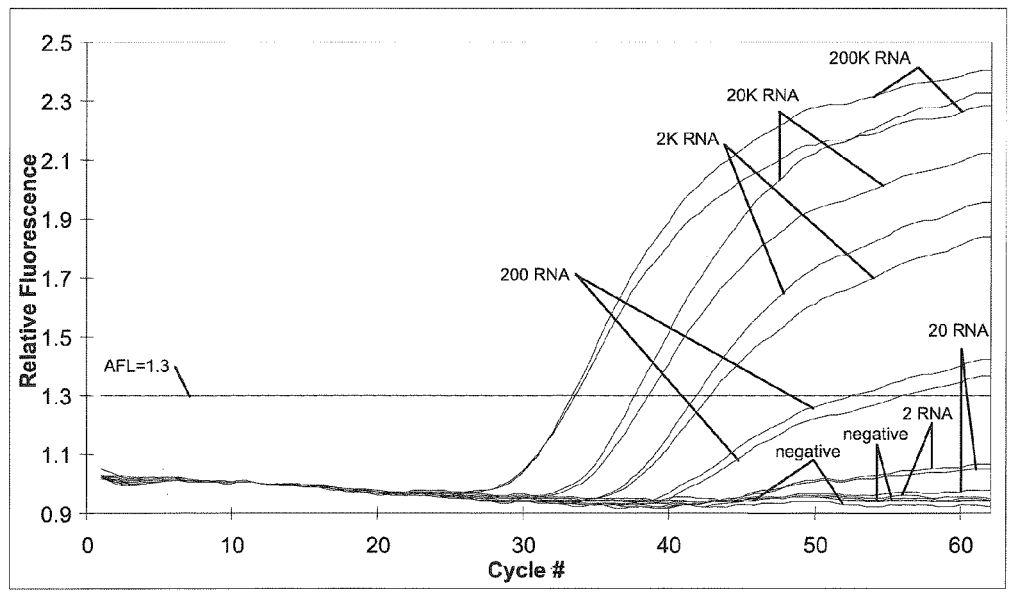
FIG. 29 is an amplification plot (ordinate represents relative fluorescence, abscissa represents the cycle number) that shows data obtained from RNA template titrations that included a single-labeled probe and methylene blue.

FIGS. 28 and 29 are amplification plots (ordinate represents relative fluorescence, abscissa represents the cycle number) that respectively show data obtained from DNA and RNA template titrations that included single-labeled nuclease probes and methylene blue in HCV detection assays. The single-labeled ST650 probes (corresponding to SEQ ID NO: 5) used in these reaction mixtures were labeled at 5'-ends with FAM. The reaction mixtures represented by these traces included poly rA and the $T_{den}$ used in these reactions was 95° C. The methylene blue concentration used in these reaction mixtures was 40 µg/mL. The labels that accompany the plots indicate the number of copies of the target cDNA or RNA from HCV along with other reaction conditions for each trace. These analyses illustrate, e.g., that highly sensitive and quantitative PCR and RT-PCR detection can be achieved using these methods.

FIG. 30 is an amplification plot (ordinate represents relative fluorescence, abscissa represents the cycle number) that shows data obtained from various 5'-nuclease reactions that included single-labeled 5'-nuclease probes and methylene blue in HIV detection assays. The single-labeled GAG108 probes (corresponding to SEQ ID NO: 9) used in these reaction mixtures were labeled at 5'-ends with FAM. In addition, the reaction mixtures represented by these traces included poly rA and the $T_{den}$ used in these reactions was 95° C. The methylene blue concentration used in the reaction mixtures was 40 µg/mL. The HCV cDNA copy number that was present in each reaction mixture is indicated in the labels that accompany the plot. This analysis illustrates, e.g., that highly sensitive and quantitative PCR detection can be achieved using this method.

FIG. 31 is a photograph of an agarose gel that shows the sensitivity of detection in 5'-nuclease assays in which target nucleic acids copy numbers were varied in the presence of methylene blue. The numbers shown above the lanes in the gel indicate the target nucleic acid copy number used for the particular run. Lanes denoted with (–) or no dye(–) are those in which negative controls were run. The reaction mixtures included poly rA and the denaturing temperature ($T_{den}$) used in these reactions was 95° C. The concentration of methylene blue in the reaction mixtures was 40 µg/mL. The target nucleic acid was from HCV and the probe was ST650 (corresponding to SEQ ID NO: 5) in the reactions shown in panel A. The target nucleic acid was from HIV and the probe was GAG108 (corresponding to SEQ ID NO: 9) in the reactions shown in panel B. These assays show, e.g., that there is no significant deleterious effect on PCR efficiency and detection sensitivity in the presence of the soluble quencher.

Example 13

Polymerase Chain Reactions Using Single-Labeled Probe and New Methylene Blue

Figure 32:
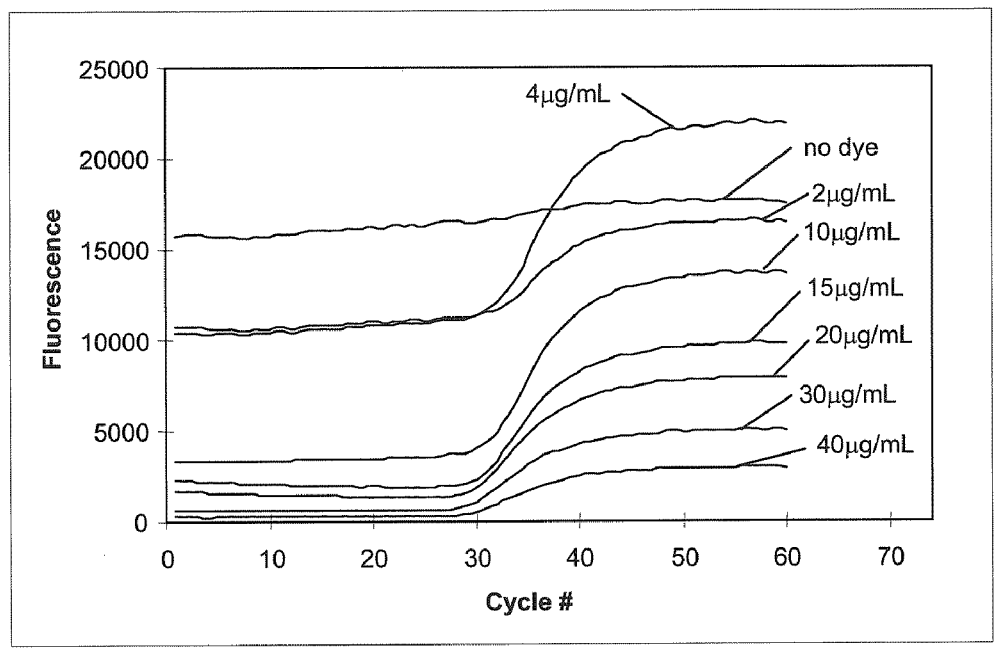
FIG. 32 is an amplification plot (ordinate represents absolute fluorescence, abscissa represents the cycle number) that shows PCR detection of HCV DNA with a single-labeled probe in the presence of various concentrations of new methylene blue when fluorescence is measured at 40° C.

FIG. 32 is an amplification plot (ordinate represents absolute fluorescence, abscissa represents the cycle number) that shows data obtained from various 5'-nuclease reactions that included single-labeled 5'-nuclease probes and new methylene blue in HCV detection assays. The single-labeled ST650 probes (corresponding to SEQ ID NO: 5) used in these reaction mixtures were labeled at 5'-ends with FAM. In addition, the reaction mixtures represented by these traces included poly rA and the $T_{den}$ used in these reactions was 95° C. 20,000 copies of HCV cDNA were present in each reaction mixture. The annealing temperature used in these reactions was 40° C. The new methylene blue concentrations used in these reaction mixtures are indicated in the labels that accompany the plot.

Figure 33:
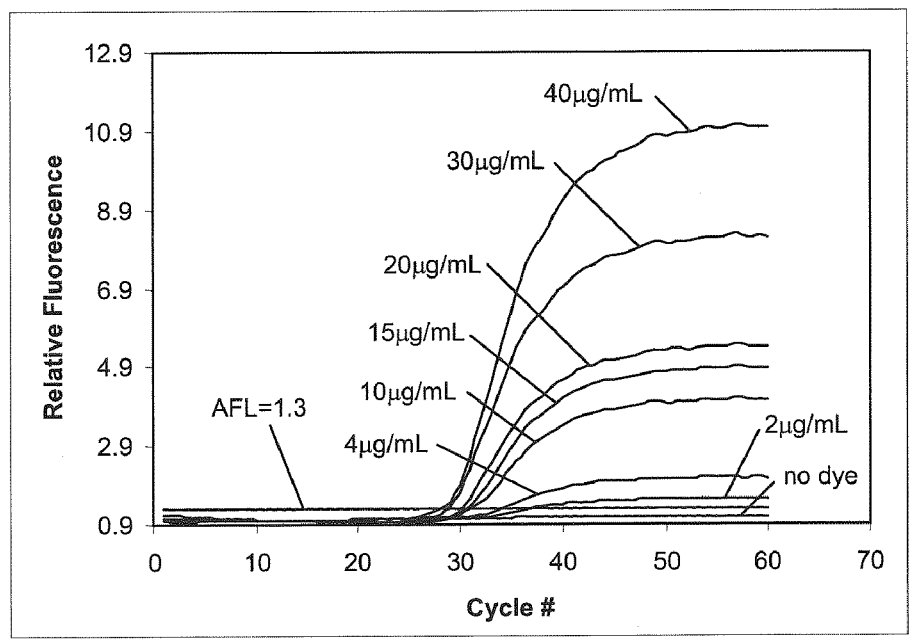
FIG. 33 is an amplification plot (ordinate represents relative fluorescence, abscissa represents the cycle number) that shows PCR detection of HCV DNA with a single-labeled probe in the presence of various concentrations of new methylene blue, when fluorescence is measured at 40° C.

FIG. 33 is an amplification plot (ordinate represents relative fluorescence, abscissa represents the cycle number) that shows data obtained from various 5'-nuclease reactions that included 5'-FAM labeled nuclease probes and new methylene blue. This plot along with others referred to herein show the relative fluorescence signal modulation with temperature. More specifically, fluorescence was detected at an annealing temperature of 40° C. in these reaction mixtures. The single-labeled ST650 probes (corresponding to SEQ ID NO: 5) used in these reaction mixtures were labeled at 5'-ends with FAM. Further, the reaction mixtures represented by these traces included poly rA and the $T_{den}$ used in these reactions was 95° C. 20,000 copies of HCV cDNA were present in each reaction mixture. The new methylene blue concentrations used in these reaction mixtures is indicated in the labels that accompany the plot.

Figure 34:
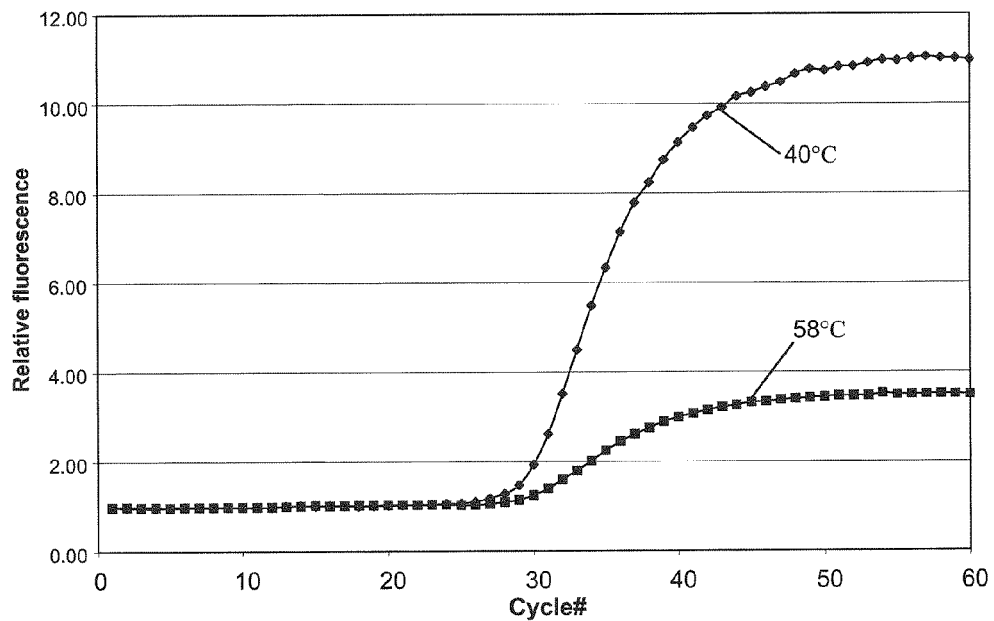
FIG. 34 is an amplification plot (ordinate represents relative fluorescence, abscissa represents the cycle number) that shows a comparison of PCR detection of HCV DNA with a single-labeled probe in the presence of 40 µg/mL new methylene blue, when fluorescence is measured at two different temperatures, 58° C., or 40° C.

FIG. 34 is an amplification plot (ordinate represents relative fluorescence, abscissa represents the cycle number) that shows data obtained from various 5'-nuclease reactions that included single-labeled 5'-nuclease probes and new methylene blue in which different anneal temperatures where utilized. The single-labeled ST650 probes (corresponding to SEQ ID NO: 5) used in these reaction mixtures were labeled at 5'-ends with FAM. In addition, the reaction mixtures represented by these traces included poly rA and the $T_{den}$ used in these reactions was 95° C. 20,000 copies of HCV cDNA were present in each reaction mixture. The new methylene blue concentrations used in the reaction mixtures was 40 µg/mL. The annealing temperature associated with each reaction mixture is indicated in the labels that accompany the plot.

Example 14

Polymerase Chain Reactions Using Multiply-Labeled Probe and Methylene Blue

This example and other examples below illustrates the modification of fluorescence in 5'-nuclease assays that included the use of multiply labeled probes. This example shows the use of methylene blue in 5'-nuclease reactions to modify the baseline emission of light from 5'-nuclease probes.

Figure 35:
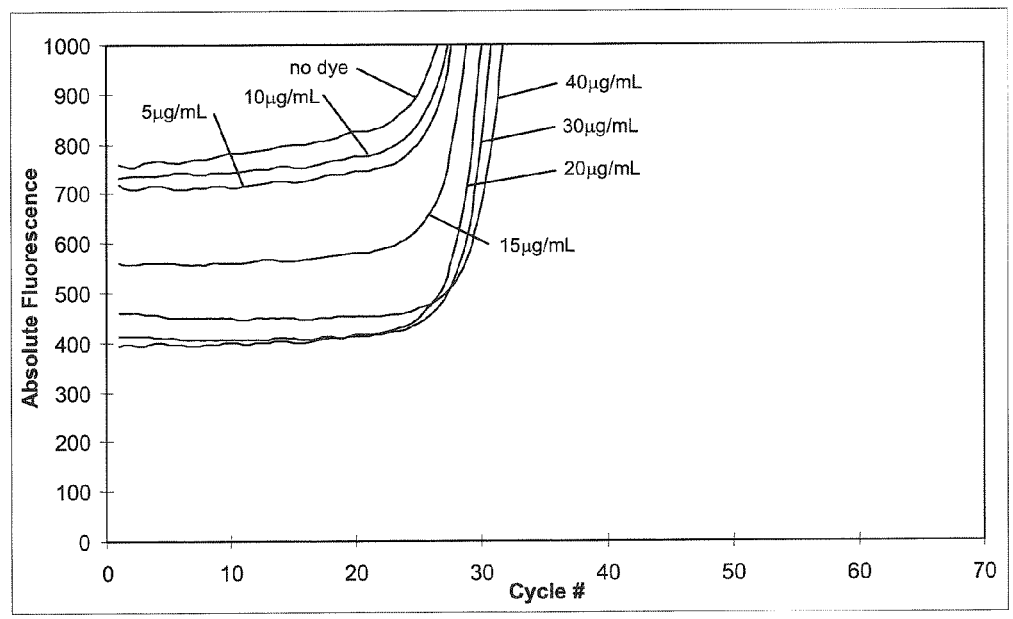
FIG. 35 is an amplification plot (ordinate represents absolute fluorescence, abscissa represents the cycle number) that shows baseline fluorescence levels obtained in 5'-nuclease assays detecting HCV with a FAM-BHQ dual-labeled probe and various amounts of methylene blue.

FIG. 35 is an amplification plot (ordinate represents absolute fluorescence, abscissa represents the cycle number) that shows data obtained from 5'-nuclease reactions performed in the presence of various methylene blue concentrations. The probes were each labeled with FAM and a BHQ™. The particular methylene blue concentrations are shown in the labels that accompany the plot.

Figure 36:
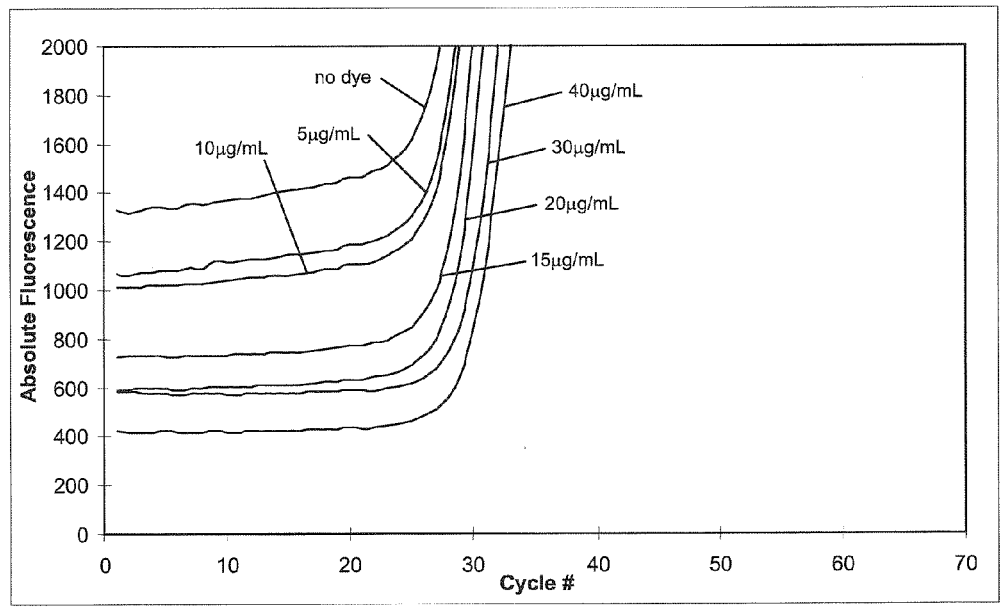
FIG. 36 is an amplification plot (ordinate represents absolute fluorescence, abscissa represents the cycle number) that shows baseline fluorescence levels obtained in 5'-nuclease assays detecting HCV with twice the amount of a FAM-BHQ dual-labeled probe than was used in the assays represented in FIG. 35 and various amounts of methylene blue.

FIG. 36 is an amplification plot (ordinate represents absolute fluorescence, abscissa represents the cycle number) that shows data obtained from 5'-nuclease reactions performed under the same conditions used for the reactions described with respect to FIG. 35 aside from doubling the concentration of probes utilized in each reaction. The particular methylene blue concentrations are shown on the plot.

Figure 37:
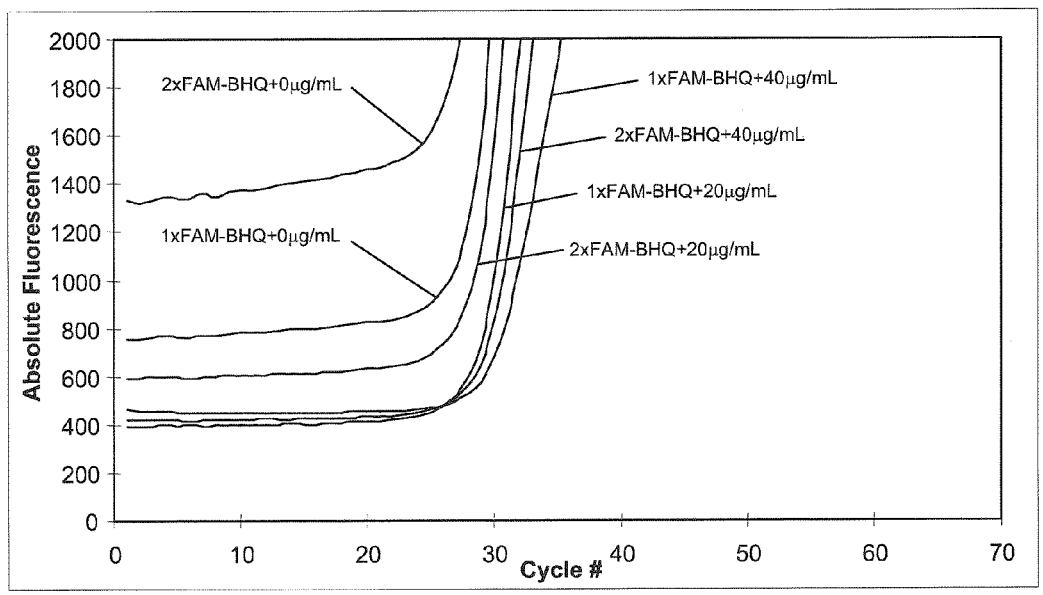
FIG. 37 is an amplification plot (ordinate represents absolute fluorescence, abscissa represents the cycle number) that shows a comparison of the baseline fluorescence levels obtained in 5'-nuclease assays detecting HCV with two different levels of a FAM-BHQ dual-labeled probe and various amounts of methylene blue.

FIG. 37 is an amplification plot (ordinate represents absolute fluorescence, abscissa represents the cycle number) that shows data obtained from 5'-nuclease reactions that simulated probe pooling. The particular methylene blue concentration and relative probe concentration associated with each trace are shown on the plot.

Figure 38:
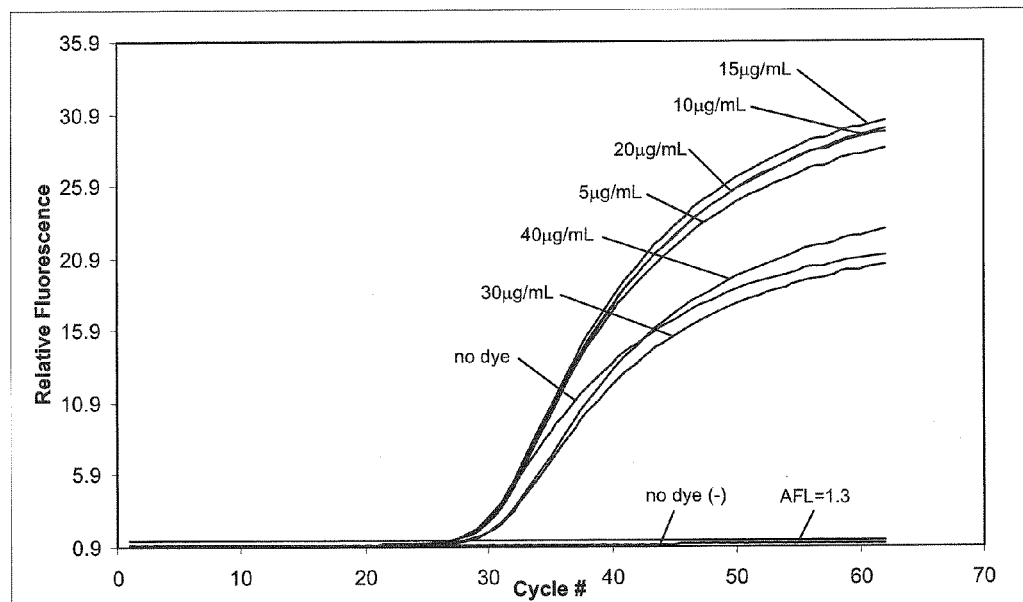
FIG. 38 is an amplification plot (ordinate represents relative fluorescence, abscissa represents the cycle number) that shows relative fluorescence levels obtained in 5'-nuclease assays detecting HCV with a FAM-BHQ dual-labeled probe and various amounts of methylene blue.

FIG. 38 is an amplification plot (ordinate represents relative fluorescence, abscissa represents the cycle number) that shows data obtained from 5'-nuclease reactions performed using a FAM-BHQ dual-labeled probe in the presence of various methylene blue concentrations. The particular methylene blue concentration associated with each trace is shown in the labels that accompany the plot.

Example 15

Polymerase Chain Reactions Using Multiply-Labeled Probe and 1,9-Dimethyl Methylene Blue This example illustrates the use of 1,9-dimethyl methylene blue in 5'-nuclease reactions to modify the baseline emission of light from 5'-nuclease probes.

Figure 39:
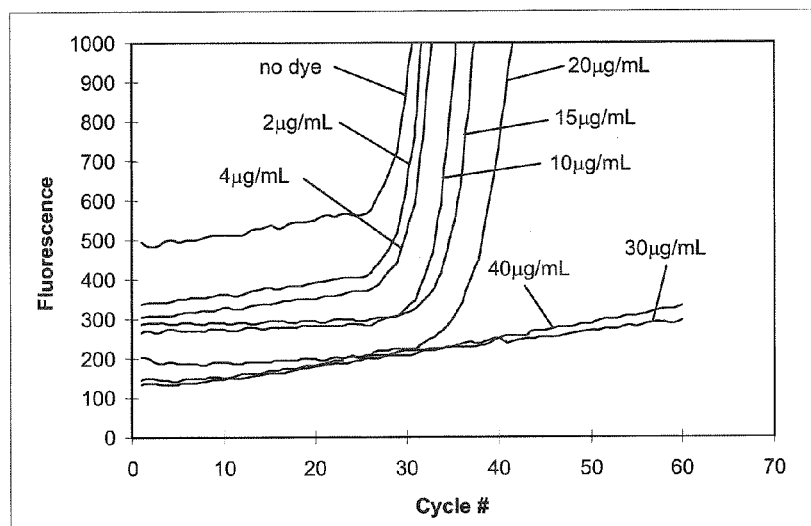
FIG. 39 is an amplification plot (ordinate represents absolute fluorescence, abscissa represents the cycle number) that shows baseline fluorescence levels obtained in 5'-nuclease assays detecting HCV with a FAM-BHQ dual-labeled probe and various amounts of dimethyl methylene blue.
Figure 40:
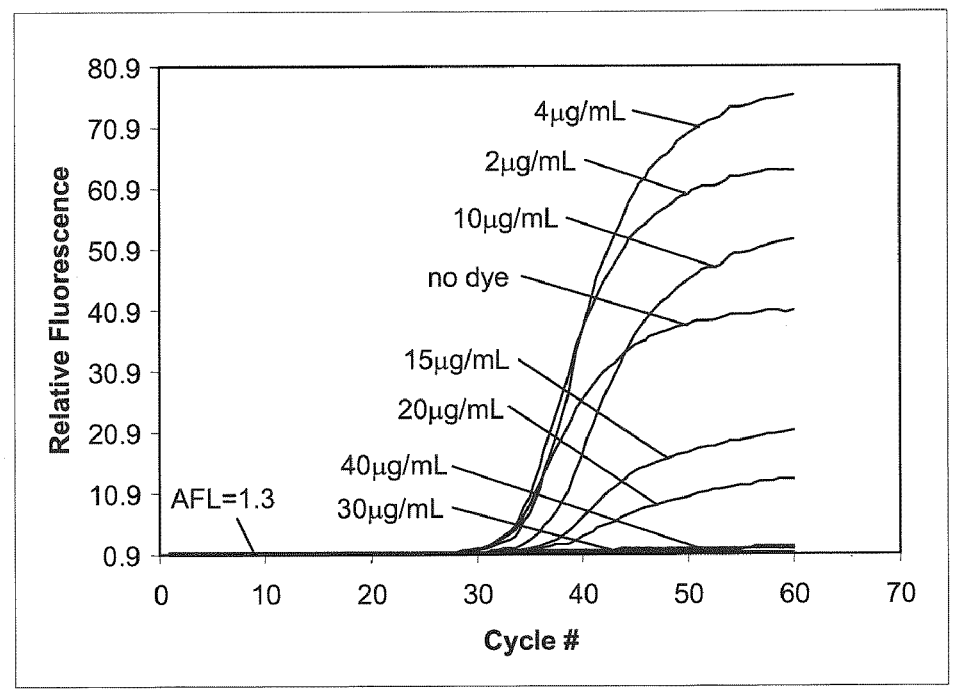
FIG. 40 is an amplification plot (ordinate represents relative fluorescence, abscissa represents the cycle number) that shows relative fluorescence levels obtained in 5'-nuclease assays detecting HCV with a FAM-BHQ dual-labeled probe and various amounts of dimethyl methylene blue.

FIG. 39 is an amplification plot (ordinate represents absolute fluorescence, abscissa represents the cycle number) that shows data obtained from 5'-nuclease reactions performed in the presence of various 1,9-dimethyl methylene blue concentrations. The reaction mixtures included poly rA and the $T_{den}$ used in these reactions was 95° C. The reaction mixtures include 20,000 copies of a target nucleic acid from HCV. The ST650 probe (corresponding to SEQ ID NO: 3) was labeled with FAM and BHQ™. The annealing temperature used in these reactions was 58° C. The particular 1,9-dimethyl methylene blue concentrations are shown in the labels that accompany the plot. The amplification plot of FIG. 40 shows the relative fluorescence for this data.

Example 16

Polymerase Chain Reactions Using Multiply-Labeled Probe and New Methylene Blue

This example illustrates the use of new methylene blue in 5'-nuclease reactions to modify the baseline emission of light from 5'-nuclease probes.

Figure 41:
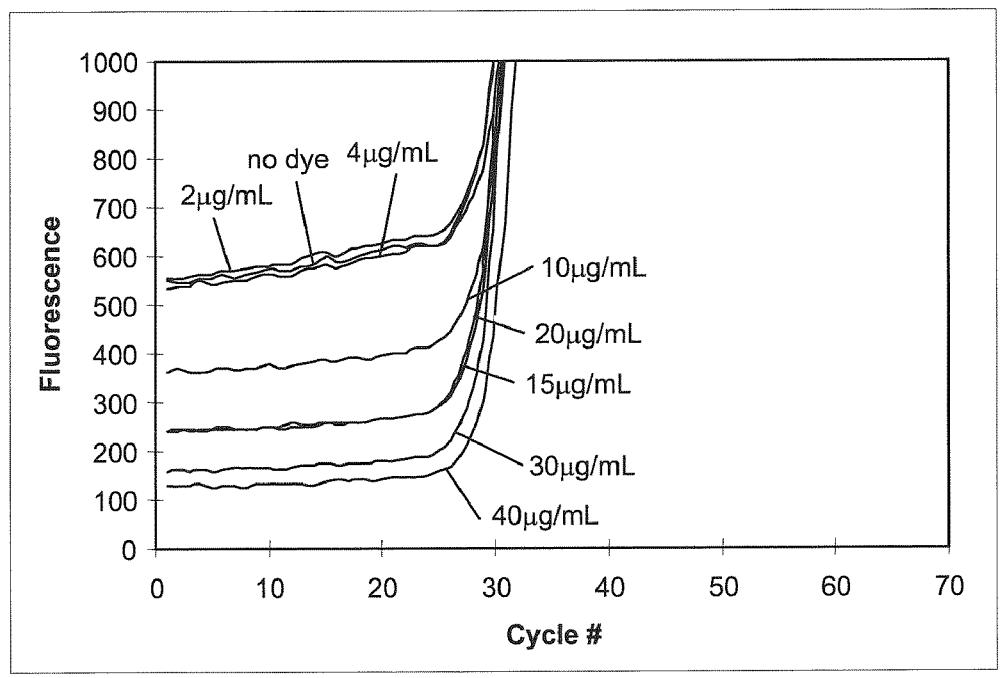
FIG. 41 is an amplification plot (ordinate represents absolute fluorescence, abscissa represents the cycle number) that shows baseline fluorescence levels obtained in 5'-nuclease assays detecting HCV with a FAM-BHQ dual-labeled probe and various amounts of new methylene blue.
Figure 42:
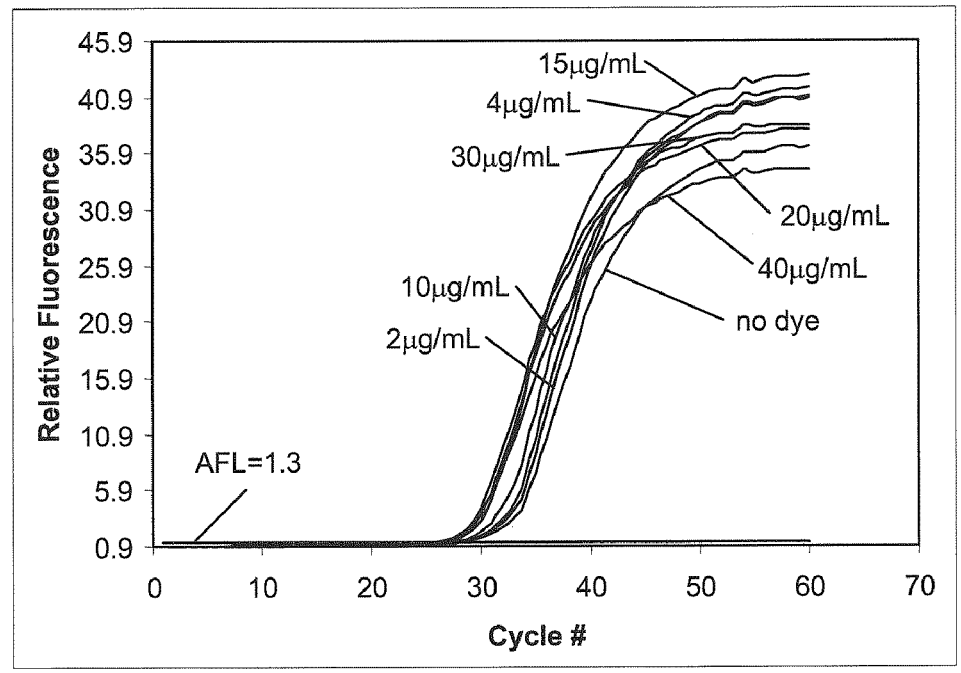
FIG. 42 is an amplification plot (ordinate represents relative fluorescence, abscissa represents the cycle number) that shows relative fluorescence levels obtained in 5'-nuclease assays detecting HCV with a FAM-BHQ dual-labeled probe and various amounts of new methylene blue.

FIG. 41 is an amplification plot (ordinate represents absolute fluorescence, abscissa represents the cycle number) that shows data obtained from 5'-nuclease reactions performed in the presence of various new methylene blue concentrations. The reaction mixtures included poly rA and the Td, used in these reactions was 95° C. The reaction mixtures include 20,000 copies of a target nucleic acid from HCV. The ST650 probe (corresponding to SEQ ID NO: 3) was labeled with FAM and a BHQ™. The particular new methylene blue concentrations are shown in the labels that accompany the plot. The annealing temperature used in these reactions was 58° C. The amplification plot of FIG. 42 shows the relative fluorescence for this data.

Example 17

Quantitation Standard Amplification and Detection Using HEX-Labeled Probe

This example illustrates the use of methylene blue to modify the baseline emission of light from a HEX labeled 5'-nuclease probe in HCV quantitation standard (HCV-QS) amplification and detection assays. The HCV QS DNA contained HCV primer binding sequences, and a unique QS-specific probe binding region. The reaction mixtures contained a primer pair that is specific for HCV and HCV QS DNA, and detection of the amplified DNA was performed by measuring the emission intensity of fluorescent reporter dyes released from the target specific QS probes during amplification, which permitted independent identification of HCV and HCV QS.

Figure 43:
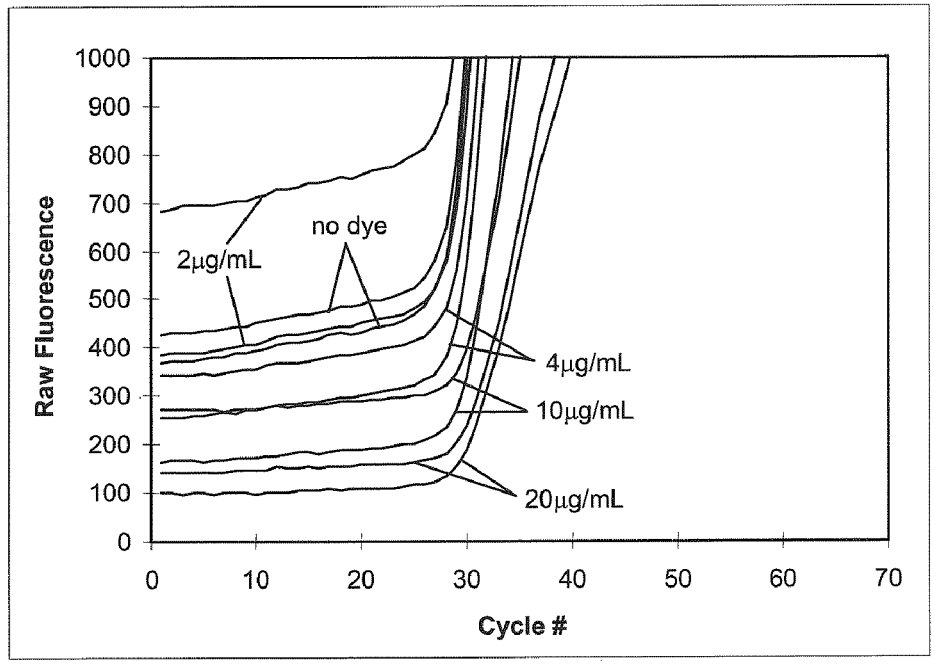
FIG. 43 is an amplification plot (ordinate represents raw fluorescence, abscissa represents the cycle number) that shows baseline fluorescence levels obtained in 5'-nuclease assays detecting IQS DNA with a HEX-CY5 dual-labeled probe and various amounts of methylene blue.
Figure 44:
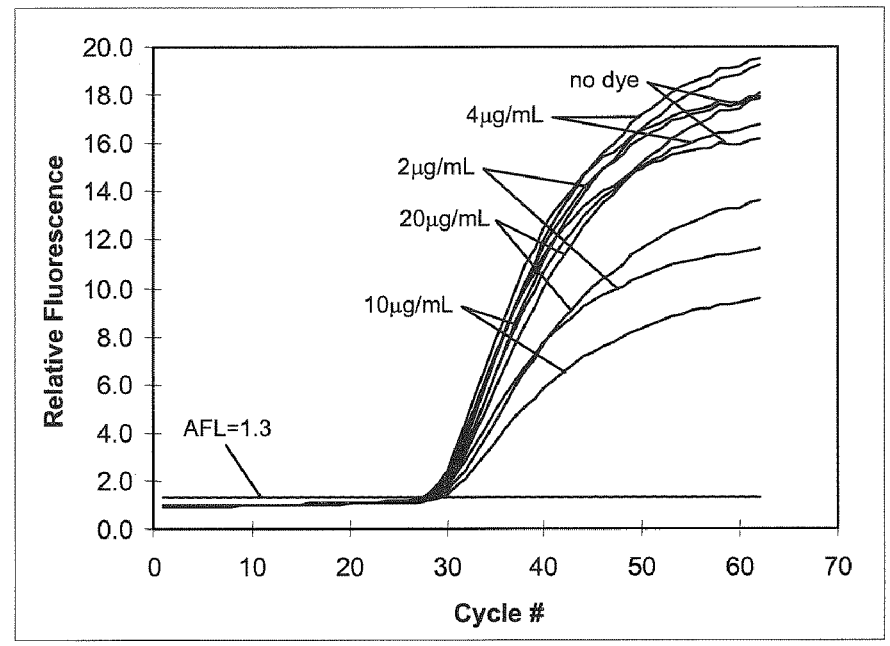
FIG. 44 is an amplification plot (ordinate represents relative fluorescence, abscissa represents the cycle number) that shows relative fluorescence levels obtained in 5'-nuclease assays detecting IQS DNA with a HEX-CY5 dual-labeled probe and various amounts of methylene blue.

More specifically, FIG. 43 is an amplification plot (ordinate represents raw fluorescence, abscissa represents the cycle number) that shows data obtained from 5'-nuclease reactions performed in the presence of various methylene blue concentrations. The reaction mixtures included poly rA and the $T_{den}$ used in these reactions was 95° C. The reaction mixtures included ST2535CY5H14 probes (corresponding to SEQ ID NO: 12) and 20,000 copies of QS-DNA. The particular new methylene blue concentrations used are shown in the labels that accompany the plot. The amplification plot of FIG. 44 shows the relative fluorescence for this data.

Example 18

Modification of Baseline Emission of Light in the Detection of HCV Nucleic Acids This example illustrates the use of various light emission modifiers to modify the baseline emission of light from 5'-nuclease probes in assays that involved the detection of HCV nucleic acids.

Figure 45:
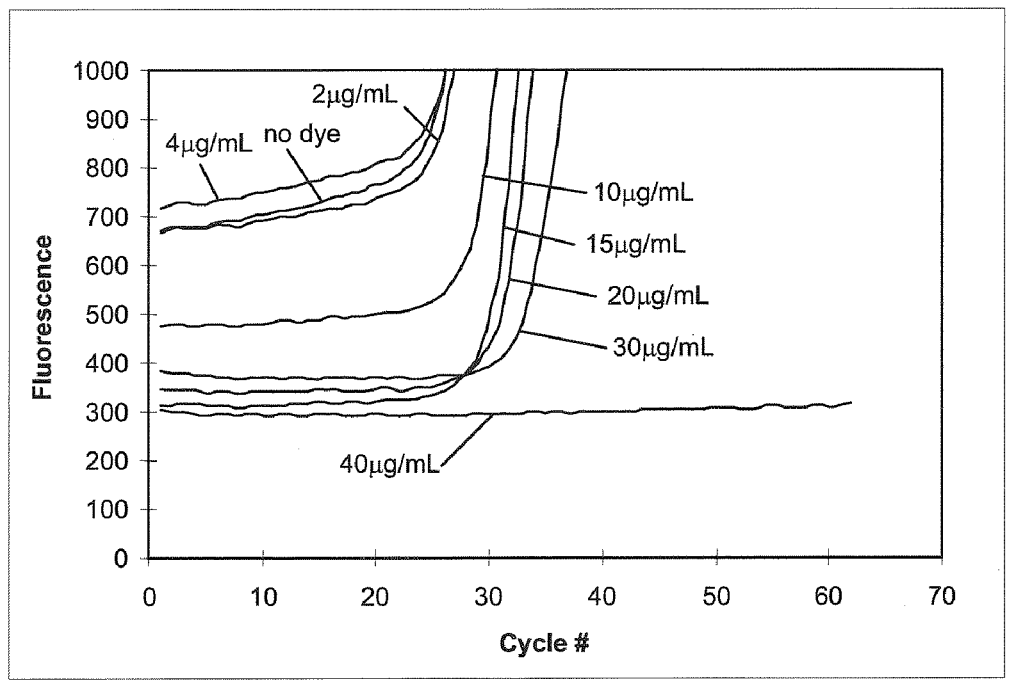
FIG. 45 is an amplification plot (ordinate represents absolute fluorescence, abscissa represents the cycle number) that shows baseline fluorescence levels obtained in 5'-nuclease assays detecting HCV with a FAM-CY5 dual-labeled probe and various amounts of Janus Green B.

FIG. 45 is an amplification plot (ordinate represents absolute fluorescence, abscissa represents the cycle number) that shows the detection of HCV nucleic acids in 5'-nuclease reactions performed in the presence of various Janus Green B concentrations. The reaction mixtures included ST650ACY5F14IN probes (corresponding to SEQ ID NO: 4) and 20,000 copies of target HCV nucleic acids. The particular Janus Green B concentrations used are shown in the labels that accompany the plot.

Figure 46:
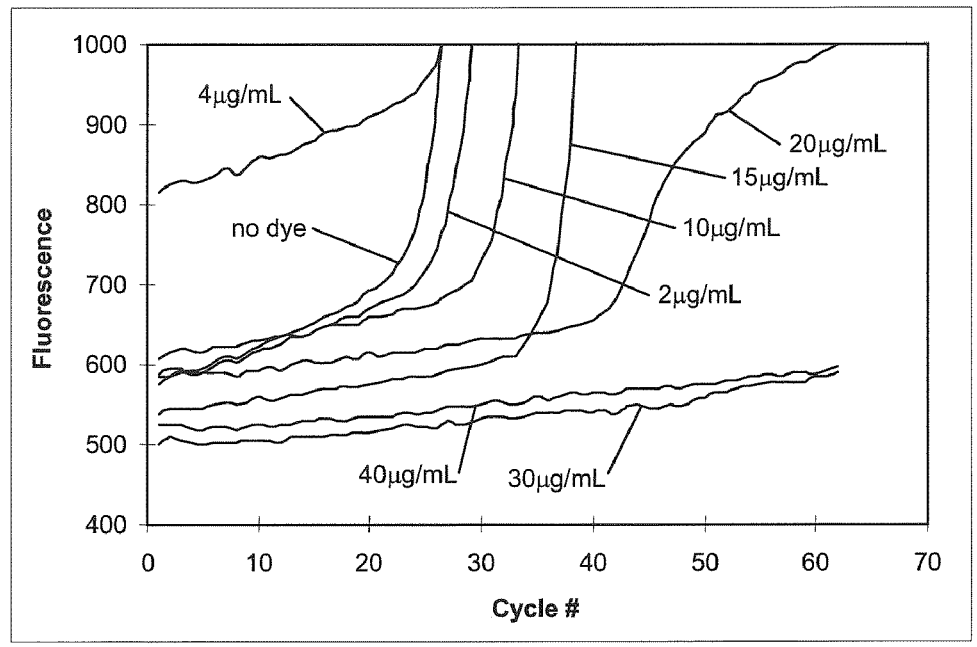
FIG. 46 is an amplification plot (ordinate represents absolute fluorescence, abscissa represents the cycle number) that shows baseline fluorescence levels obtained in 5'-nuclease assays detecting HCV with a FAM-CY5 dual-labeled probe and various amounts of toluidine blue.

FIG. 46 is an amplification plot (ordinate represents absolute fluorescence, abscissa represents the cycle number) that shows the detection of HCV nucleic acids in 5'-nuclease reactions performed in the presence of various toluidine blue concentrations. The reaction mixtures included ST650ACY5F14IN probes (corresponding to SEQ ID NO: 4) and 20,000 copies of target HCV nucleic acids. The particular toluidine blue concentrations used are shown in the labels that accompany the plot.

Figure 47:
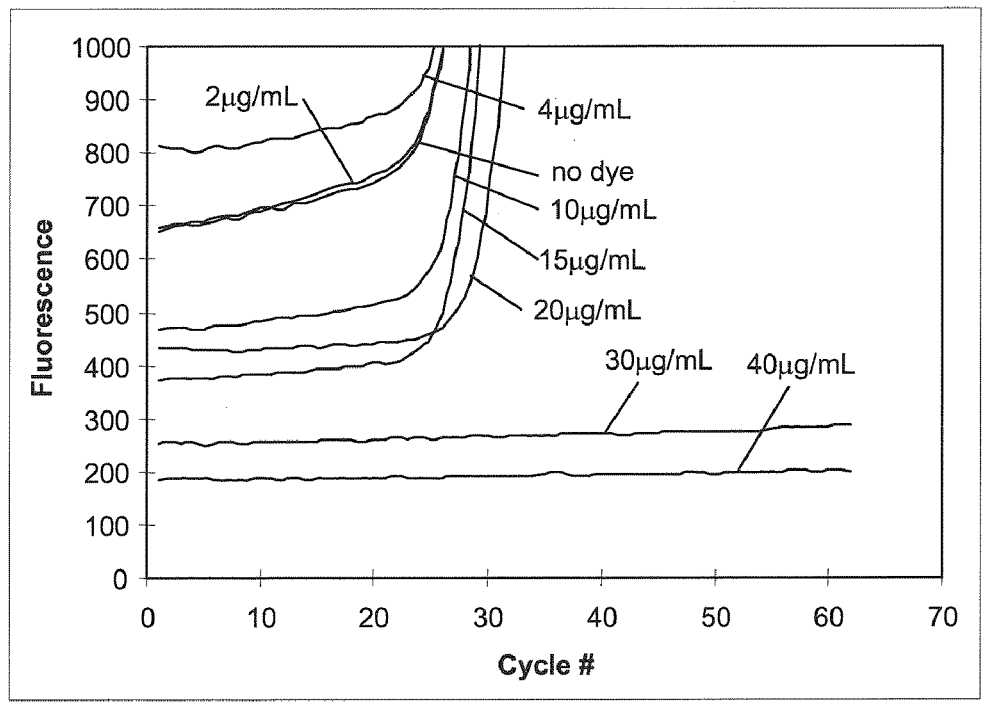
FIG. 47 is an amplification plot (ordinate represents absolute fluorescence, abscissa represents the cycle number) that shows baseline fluorescence levels obtained in 5'-nuclease assays detecting HCV with a FAM-CY5 dual-labeled probe and various amounts of Victoria Pure Blue BO.

FIG. 47 is an amplification plot (ordinate represents absolute fluorescence, abscissa represents the cycle number) that shows the detection of HCV nucleic acids in 5'-nuclease reactions performed in the presence of various Victoria Pure Blue BO concentrations. The particular Victoria Pure Blue BO concentrations used are shown in the labels that accompany the plot.

Figure 48:
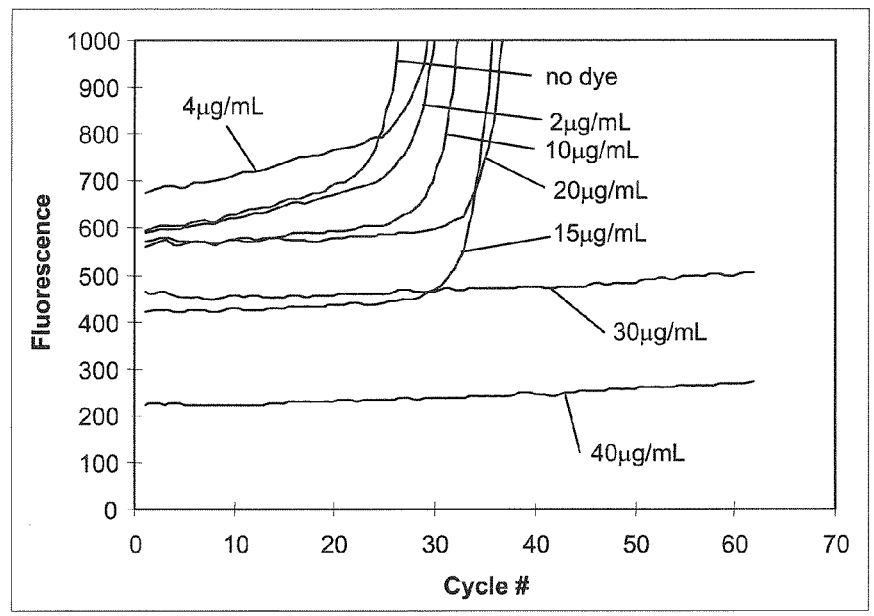
FIG. 48 is an amplification plot (ordinate represents absolute fluorescence, abscissa represents the cycle number) that shows baseline fluorescence levels obtained in 5'-nuclease assays detecting HCV with a FAM-CY5 dual-labeled probe and various amounts of azure A.

FIG. 48 is an amplification plot (ordinate represents absolute fluorescence, abscissa represents the cycle number) that shows the detection of HCV nucleic acids in 5'-nuclease reactions performed in the presence of various azure A concentrations. The particular azure A concentrations used are shown in the labels that accompany the plot.

Figure 49:
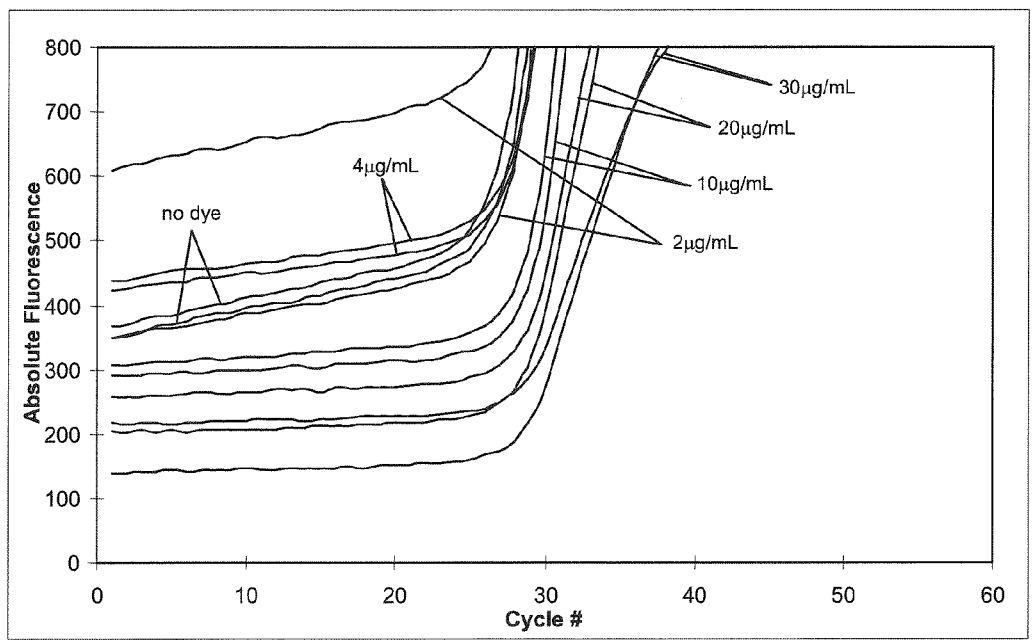
FIG. 49 is an amplification plot (ordinate represents absolute fluorescence, abscissa represents the cycle number) that shows baseline fluorescence levels obtained in 5'-nuclease assays detecting HCV with a FAM-CY5 dual-labeled probe and various amounts of methylene green.

FIG. 49 is an amplification plot (ordinate represents absolute fluorescence, abscissa represents the cycle number) that shows the detection of HCV nucleic acids in 5'-nuclease reactions performed in the presence of various methylene green concentrations. The reaction mixtures included poly rA and the $T_{den}$ used in these reactions was 95° C. The reaction mixtures included ST650ACY5F14IN probes (corresponding to SEQ ID NO: 4) and 20,000 copies of target HCV nucleic acids. The particular methylene green concentrations used are shown in the labels that accompany the plot.

Figure 50:
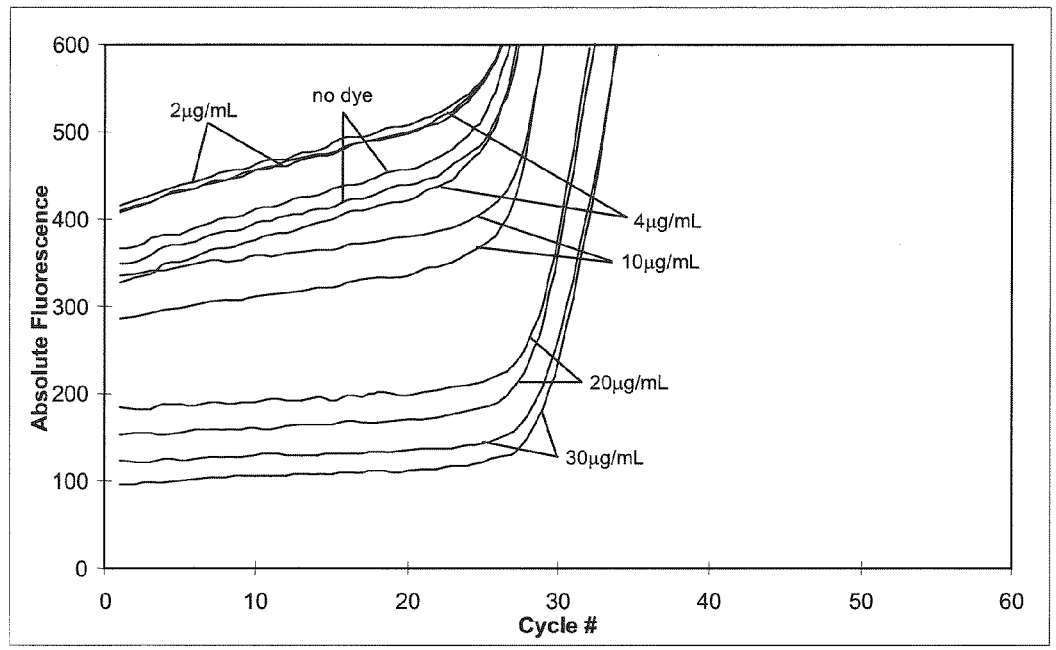
FIG. 50 is an amplification plot (ordinate represents absolute fluorescence, abscissa represents the cycle number) that shows baseline fluorescence levels obtained in 5'-nuclease assays detecting HCV with a FAM-CY5 dual-labeled probe and various amounts of thionin.

FIG. 50 is an amplification plot (ordinate represents absolute fluorescence, abscissa represents the cycle number) that shows the detection of HCV nucleic acids in 5'-nuclease reactions performed in the presence of various thionin concentrations. The reaction mixtures included poly rA and the $T_{den}$ used in these reactions was 95° C. The reaction mixtures included ST650ACY5F14IN probes (corresponding to SEQ ID NO: 4) and 20,000 copies of target HCV nucleic acids. The particular thionin concentrations used are shown in the labels that accompany the plot.

Figure 51:
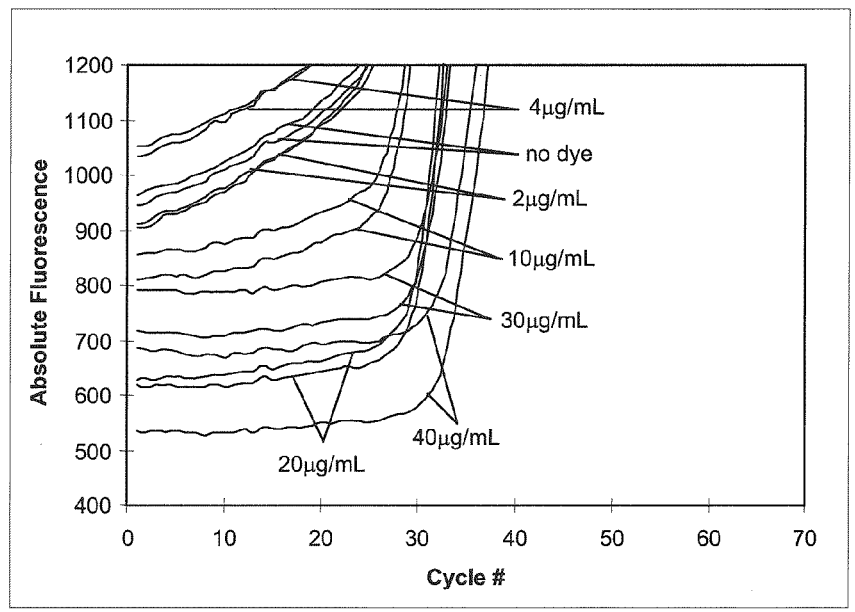
FIG. 51 is an amplification plot (ordinate represents absolute fluorescence, abscissa represents the cycle number) that shows baseline fluorescence levels obtained in 5'-nuclease assays detecting HCV with a FAM-CY5 dual-labeled probe and various amounts of azure B.

FIG. 51 is an amplification plot (ordinate represents absolute fluorescence, abscissa represents the cycle number) that shows the detection of HCV nucleic acids in 5'-nuclease reactions performed in the presence of various azure B concentrations. The reaction mixtures included poly rA and the $T_{den}$ used in these reactions was 95° C. The reaction mixtures included ST650ACY5F14IN probes (corresponding to SEQ ID NO: 4) and 20,000 copies of target HCV nucleic acids. The particular azure B concentrations used are shown in the labels that accompany the plot.

Example 19

Melting Curve Analysis (Tm Determination) Using a Single-Labeled Probe in Conjunction with a Soluble Light Emission Modifier in an HCV Model System The present example describes a melting curve analysis (i.e., Tm determination) using a single-labeled probe in conjunction with a soluble light emission modifier (i.e., soluble quencher). An HCV probe and HCV synthetic templates are used in the experimental system. The effectiveness of using the single-labeled probe with a soluble quencher is demonstrated.

An HCV typing probe was designed and synthesized (SEQ ID NO: 14), and contains a single fluorescein (FAM) label, as shown in FIG. 52A. This probe hybridizes to a domain within the heterogeneous 5'-UTR of the HCV genome. The probe was alternatively hybridized with different synthetic single-stranded templates corresponding to various HCV genotypes as listed in the table below.

| HCV/<br>Genotype/<br>Subtype | Synthetic Template | SEQ ID<br>NO: |
| --- | --- | --- |
| 1a/b | AGGACCCGGTCGTCCTGGCAATTCCGGTGTA | 15 |
| 2a/c | AGGACCCAGTCTTCCCGGCAATTCCGGTGTA | 16 |
| 4 | AGGACCCGGTCATCCCGGCGATTCCGGTGTA | 17 |
| 2b | AGGACCCGGTCTTTCCGGTAATTCCGGTGTA | 18 |
| 5 | AGGACCCGGTCATCCCGGCAATTCCGGTGTA | 19 |
| 6 | AGGACCCGGTCATCCTGGCAATTCCGGTGTA | 20 |
| 3a | AGGACCCGGTCACCCCAGCGATTCCGGTGTA | 21 |

The probe was annealed to each of the synthetic templates in separate reactions. For the melting analysis, the various hybridization mixtures were heated to 95° C. for 2 min, followed by cooling to 20° C. to allow annealing and the formation of hybridization complexes. The reactions containing the hybridization complexes were then heated in approximately 76 cycles where each cycle increases the temperature 1° C. for 30 seconds. Fluorescence was measured for 50 milliseconds at the end of each 30 second cycle. The melting reactions were run in 96 well microtiter plates, and fluorescence was monitored using an ABI PRISM® RTM 7700 Sequence Detection System (Applied Biosystems, Foster City, Calif.). Fluorescence was measured in this experiment (and all experiments that used FAM-labelled probes) using an excitation filter at 485 nm with a 20 nm bandwidth, and an emission filter at 520 nm with a 10 nm bandwidth.

The formation/dissociation of hybridization complexes in the mix was monitored using a soluble quencher system. The FAM label covalently attached to the probe provided a suitable donor emission. The quenching action was provided by the soluble quencher methylene blue. Methylene blue is a member of a family of soluble quenchers based on thiazine and diazine dye structures. The methylene blue quencher has a binding affinity for double-stranded DNA, and exhibits a quenching effect when in close proximity to the fluorescent label on the probe when the probe is in a duplex structure with the target. However, the soluble quencher has reduced affinity for single-stranded DNA. Thus, when the solution containing the hybridization complex comprising the probe is heated and eventually dissociates, the affinity of the quencher for the nucleic acid is reduced, resulting in an increase in fluorescence.

The fluorescence data can be shown graphically by plotting a raw fluorescence value as a function of temperature. In one control experiment, the methylene blue soluble quencher was omitted from the melting reaction. The results of separate experiments (a melting analysis using the probe and each HCV synthetic template) were overlaid on the same plot, and are shown in FIG. 52B. In these experiments, the results of multiple separate experiments are overlaid on the same graph. A representative set of data is shown. As might be expected in the absence of the soluble quencher, there was no significant change in FAM fluorescence indicating a transition from duplex to single stranded state in each of the examples, due to the absence of a quenching moiety, despite the temperature cycling program which would result in annealing and melting of DNA duplexes.

Figure 53:
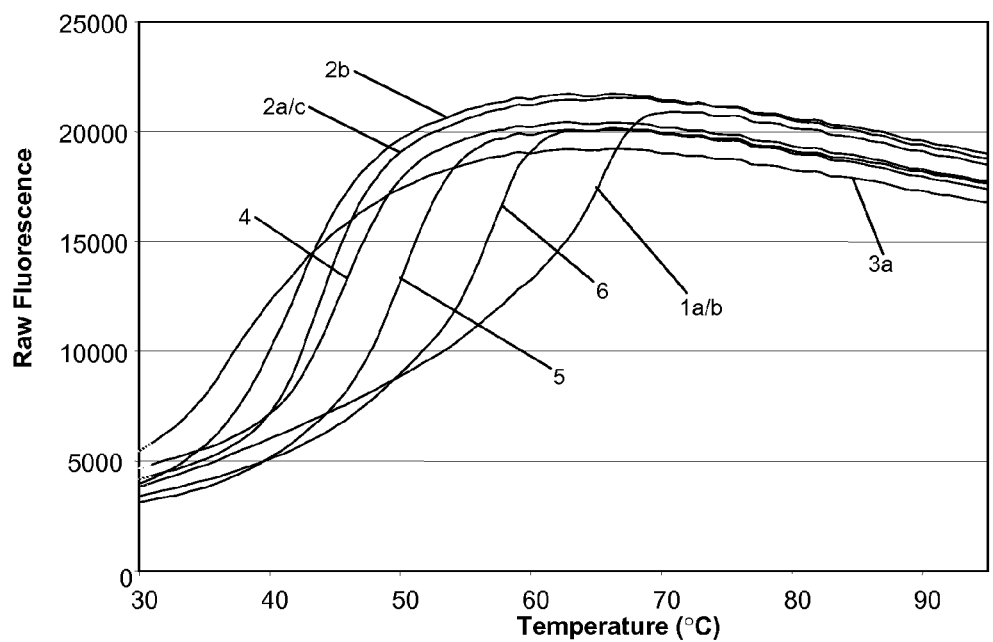
FIG. 53 provides a melting curve analysis showing raw fluorescence plotted as a function of temperature using a single-labeled HCV genotyping probe and synthetic nucleic acid targets. The experimental conditions were identical to those used in FIG. 52B, except that 10 µg/mL of soluble light emission modifier (i.e., soluble quencher) methylene blue were included in the reactions.

Next, using the same reagents in a new analysis, methylene blue was added to the melting reactions at a concentration of 10 μg/mL. The results of that melting analysis are shown in FIG. 53. As can be seen, each probe/template complex gave a distinct dissociation profile upon heating, indicating varying Tm values for the different genotypes.

Figure 54:
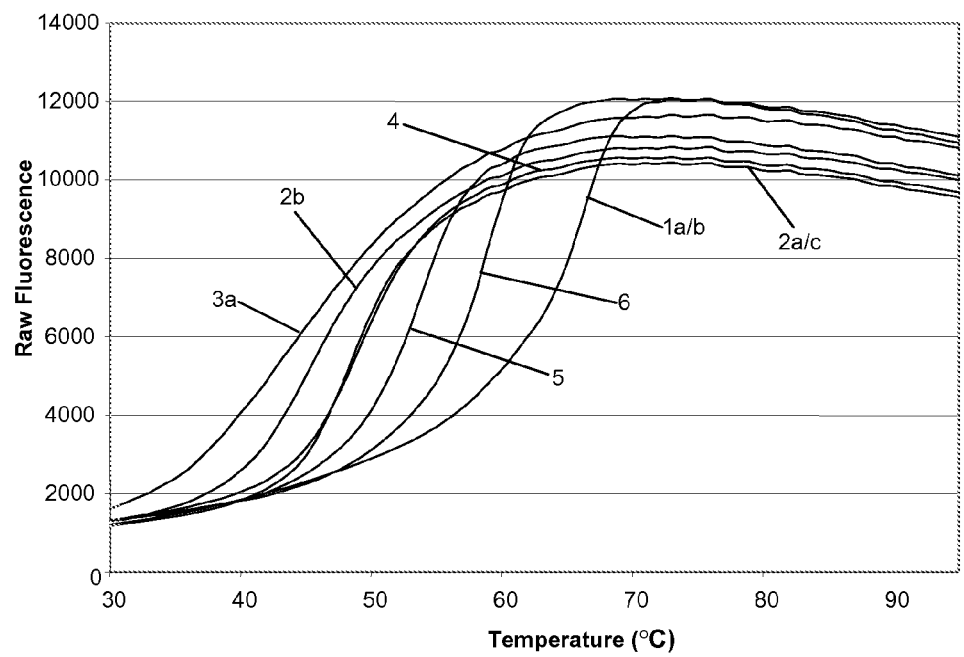
FIG. 54 provides a melting curve analysis using the same conditions used in FIG. 53, except that 20 µg/mL of soluble quencher methylene blue were included in the reactions.

In the next experiment, methylene blue was added to the melting reactions at a concentration of 20 μg/mL. The results of that melting analysis are shown in FIG. 54. As can be seen, each probe/template complex again gave a distinct dissociation profile upon heating, indicating distinct Tm values corresponding to the different HCV genotypes.

Figure 55:
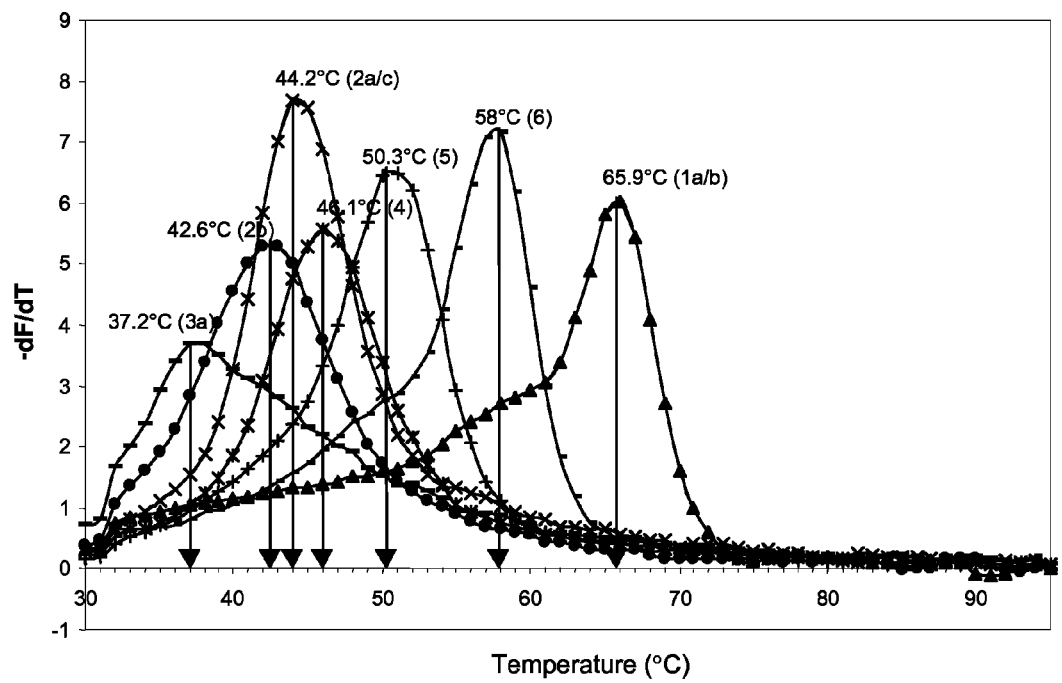
FIG. 55 provides the first derivative plot of the melting curve analysis shown in FIG. 54. The HCV genotypes and the experimentally observed Tm values are indicated.

The data in FIG. 54 can be more readily interpreted by using a first derivative plot of the same data. FIG. 55 shows the data in FIG. 54 as a first derivative plot. The peak of each curve represents the $T_m$ of the hybridization complex at those particular hybridization conditions. As can be seen, the $T_m$ for each HCV genotype can be easily distinguished on the graph. Thus, the soluble quencher thiazine dye azure B can be successfully used in a melting curve Tm determinations.

Example 20

Demonstration of Nucleic Acid Duplex Stabilization in the Presence of Thiazine Dyes Using an HCV Model System The present example illustrates the duplex stabilization properties of thiazine dyes. An HCV probe and HCV synthetic templates are used in the experimental system, and duplex stabilization is demonstrated by measuring the Tm of the various hybridization complexes that are formed.

Figure 56:
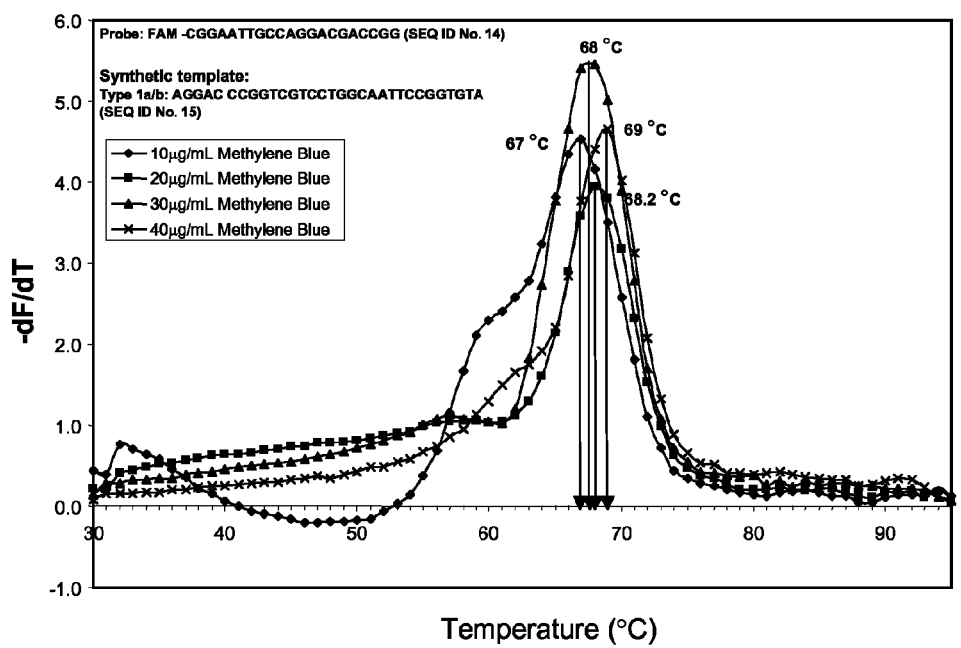
FIG. 56 provides first derivative plot of a melting curve (Tm) analysis using a FAM single-labeled HCV genotyping probe, a synthetic nucleic acid target corresponding to HCV genotype 1a/b and four increasing concentrations of methylene blue. The sequences of the probe and synthetic template are shown, which form a perfect match duplex. The results of the four separate experiments are overlaid on the same graph. A representative set of data is shown.

Melting curve reactions were established using the single-label probe (SEQ ID NO: 14) and HCV type 1a/b synthetic template (SEQ ID NO: 15) as shown in FIG. 56. This analysis used the same methodologies as described in the Example above. This particular combination of probe and HCV genotype 1a/b template produces a perfect alignment (no mismatches). These melting analysis reactions alternatively contained four increasing concentrations of the thiazine dye methylene blue ranging from 10-40 μg/mL. The melting data is shown in FIG. 56 as a first derivative plot of fluorescence versus temperature. The results of the four separate experiments are overlaid on the same graph. A representative set of data is shown. As can be seen in the figure, the increasing concentration of methylene blue resulted in increased stability of the perfect match duplexes, reflected in the higher Tm values as the concentration of methylene blue was increased.

Figure 57:
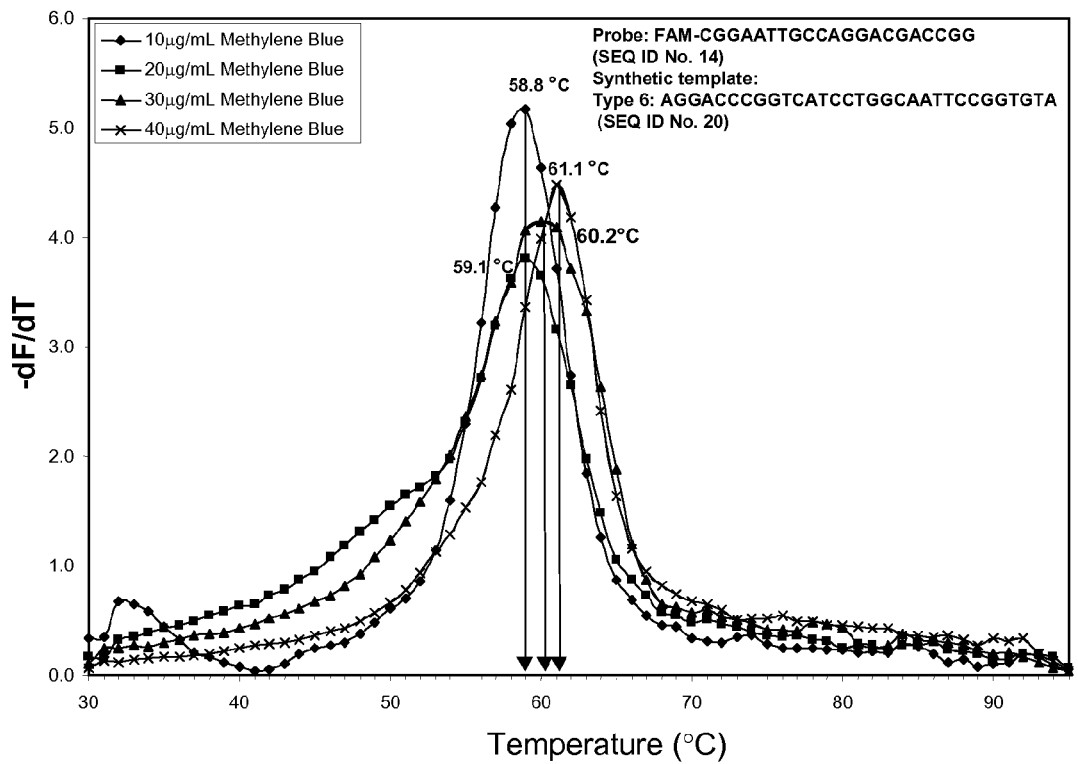
FIG. 57 provides a first derivative plot of a melting curve (Tm) analysis using a FAM single-labeled HCV genotyping probe, a synthetic nucleic acid target corresponding to HCV genotype 6 and four increasing concentrations of methylene blue. The sequences of the probe and synthetic template are shown, which form a duplex with one mismatch. The results of the four separate experiments are overlaid on the same graph. A representative set of data is shown.

Three additional experiments were run where the duplexes contain one, two or three mismatches, and the effects of methylene blue on duplex stability was assessed. In the first of these experiments, melting curve reactions were established using the same HCV genotyping probe as used in FIG. 56, and an HCV synthetic template corresponding to HCV genotype 6 (SEQ IN NO: 20), as shown in FIG. 57. This particular combination of probe and genotype 6 template produces a nucleic acid duplex containing one mismatch position. As in the previous experiment, the melting reactions contained alternatively four increasing concentrations of the thiazine dye methylene blue ranging from 10-40 μg/mL. The melting data is shown in FIG. 57 as a first derivative plot of fluorescence versus temperature. The results of the four separate experiments are overlaid on the same graph. A representative set of data is shown. As can be seen in FIG. 57, the increasing concentration of methylene blue resulted in increased stability of the duplexes containing one mismatch, reflected in the higher Tm values as the concentration of methylene blue was increased.

Figure 58:
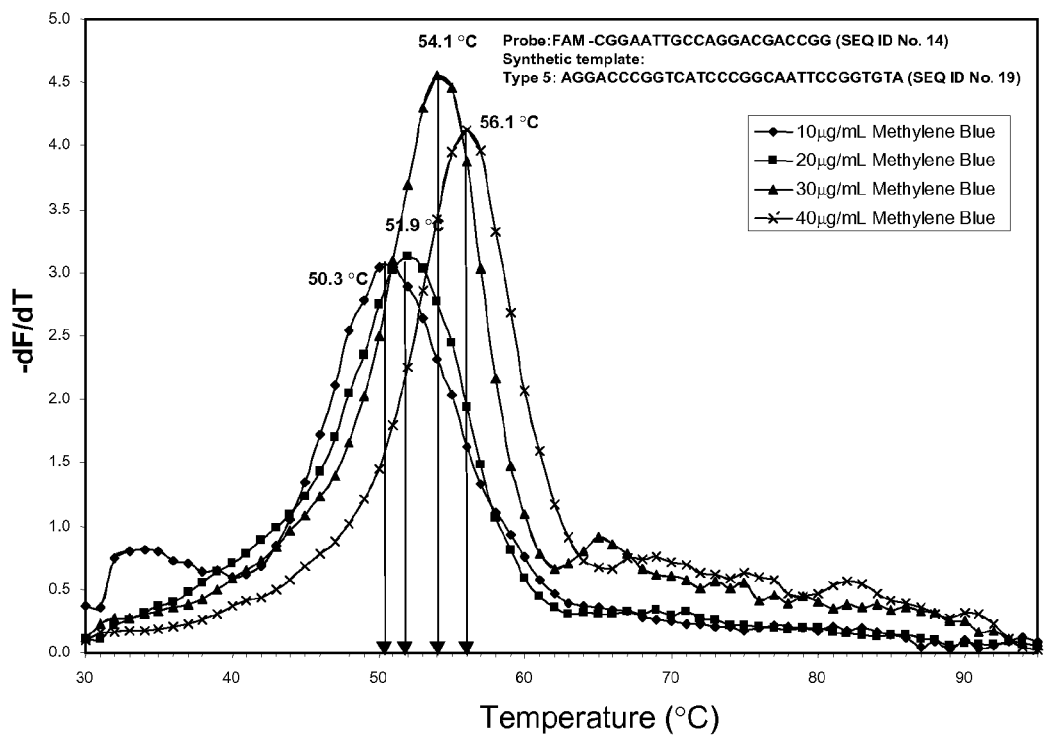
FIG. 58 provides first derivative plot of a melting curve (Tm) analysis using a FAM single-labeled HCV genotyping probe, a synthetic nucleic acid target corresponding to HCV genotype 5 and four increasing concentrations of methylene blue. The sequences of the probe and synthetic template are shown, which form a duplex with two mismatch positions.

Similarly, melting curve reactions were also established using the same HCV genotyping probe and an HCV synthetic template corresponding to HCV genotype 5 (SEQ IN NO: 19), as shown in FIG. 58. This combination of probe and genotype 5 template produces a nucleic acid duplex containing two mismatch positions. The melting reactions contained alternatively four increasing concentrations of the thiazine dye methylene blue. The melting data is shown in FIG. 58 as a first derivative plot of fluorescence versus temperature. The results of the four separate experiments are overlaid on the same graph. A representative set of data is shown. As can be seen in FIG. 58, the increasing concentration of methylene blue resulted in increased stability of the duplexes containing two mismatches, reflected in the higher Tm values as the concentration of methylene blue was increased.

Melting curve reactions were also established with HCV probe and template that resulted in nucleic acid duplexes containing three mismatch positions, as shown in FIG. 59. These reactions used an HCV synthetic template corresponding to HCV genotype 2a/c (SEQ ID NO: 16). The melting reactions contained alternatively four increasing concentrations of the thiazine dye methylene blue. The melting data is shown in FIG. 59 as a first derivative plot of fluorescence versus temperature. where the results of the four separate experiments are overlaid on the same graph. A representative set of data is shown. As can be seen in FIG. 59, the increasing concentration of methylene blue resulted in increased stability of the duplexes containing the three mismatches, reflected in the higher Tm values as the concentration of methylene blue was increased.

It is significant to note that the degree of stabilization is more pronounced with increasing concentrations of methylene blue, and furthermore, duplexes that containing increasing numbers of mismatches show larger degrees of stabilization as measured by Tm. For example, with no mismatches present in a duplex (FIG. 56), the difference in Tm values when using 10 μg/mL methylene blue versus 40 μg/mL methylene blue is 2.0° C. However, with three mismatches present in a duplex (FIG. 59), the difference in Tm values when using 10 μg/mL methylene blue versus 40 μg/mL methylene blue is much more pronounced with a 12.4° C. spread between those reaction conditions. Duplexes having one, and two mismatches present (FIGS. 57 and 58) show intermediate degrees of duplex stabilization.

Example 21

Nucleic Acid Duplex Stabilization in the Presence of Thiazine Dyes Using Multiple HCV Template Targets The duplex stabilization feature of thiazine dyes is further illustrated in the bar graph provided in FIG. 60. This bar graph provides a summary of Tm determinations using the HCV probes indicated with the various synthetic nucleic acids having nucleotide sequences corresponding to the HCV genotypes shown. This analysis examined the effects of methylene blue, where alternatively no methylene blue, 10 μg/mL methylene blue or 20 μg/mL methylene blue were used in the melting curve analysis.

These determinations were done using one of two different methodologies. In one set of experiments, Tm determinations were made in the absence of new methylene blue. In that case, a single-labeled FAM probe would be ineffective in the Tm determination, because there is not a suitable donor/quencher pair present to monitor duplex formation/dissociation. In that case, a probe was synthesized without a FAM label (SEQ ID NO: 22), and the melting curve and Tm determination were accomplished by including SYBR® Green in the reaction. SYBR® Green staining is specific for double stranded DNA, and so is an effective monitor for duplex association/dissociation. Alternatively, when methylene blue was present in the melting reactions, a single-labeled FAM probe (SEQ ID NO: 14) was used as previously described. In these experiments, the nucleotide sequences of the two different probes were identical; the only difference between the two probes was the absence/presence of the FAM label.

The resulting duplexes contained varying numbers of nucleotide mismatches, as shown below:

| HCV Genotype Template | Number of Nucleotide Mismatches Present when in a Duplex with the Probe |
|---|---|
| 1a/b | 0 |
| 2a/c | 3 |

-continued

| HCV Genotype Template | Number of Nucleotide Mismatches Present when in a Duplex with the Probe |
|---|---|
| 2b | 4 |
| 3a | 5 |
| 4 | 3 |
| 5 | 2 |
| 6 | 1 |

The results of this type of analysis using seven different synthetic templates corresponding to various HCV genotypes/subtypes, are summarized in FIG. 60, and demonstrate the general nature of the duplex stabilization effect. A representative set of data is shown. This data is also summarized in the table below.

| Treatment | Genotype | | | | | | |
|---|---|---|---|---|---|---|---|
| | 3a | 2b | 2a/c | 4 | 5 | 6 | 1a/b |
| 0 µg/mL new methylene blue + unlabeled probe + SYBR ® Green | 32 | 36 | 39 | 32 | 48.9 | 56.8 | 64.5 |
| 10 µg/mL new methylene blue + labeled probe | 34.2 | 40 | 41.1 | 45.6 | 53.7 | 58 | 66.9 |
| 20 µg/mL new methylene blue + labeled probe | 38.2 | 42.2 | 47 | 47.7 | 54 | 61.2 | 68.2 |

Two distinct trends can be observed in this figure, illustrating the duplex stabilizing effects of the methylene blue. First, in the analysis of any one HCV genotype, there is an elevation in duplex stability with the addition of increasing concentrations of methylene blue. This is true for both perfectly matched duplexes (genotype 1a/b) as well as duplexes containing one or more mismatches (all other genotypes). Second, those duplexes that contain larger numbers of mismatches generally showed the greatest degree of stabilization (as measured by the changes in the Tm) with the addition of methylene blue to the melting analysis. For example, duplexes containing HCV genotype 1a/b (perfect match, no mismatches) showed only a slight elevation in experimentally observed Tm value with the addition of methylene blue. In contrast, duplexes having one or more mismatched nucleotide positions showed greater degrees of improved duplex stability with the addition of new methylene blue. Similar effects were also observed when using the thiazine dye methylene blue.

It is significant to point out that in the case of the experiments summarized in FIG. 60, the methylene blue is serving two functions. In the case where a single FAM-labeled probe is used in the melting analysis, the new methylene blue is first serving as a soluble quencher with the FAM-labeled probe in order to monitor duplex association/dissociation. Second, as illustrated herein, the new methylene blue is acting to stabilize duplexes, and most significantly, duplexes that contain nucleotide mismatches. In this comparison, the data for the zero dye (new methylene blue) controls is obtained by using unlabeled probe and SYBR Green detection for the Tm determination.

Example 22

Demonstration of Single Nucleotide Mismatch Stabilization in the Presence of Thiazine Dyes The present example further illustrates single nucleotide mismatch stabilization properties of thiazine dyes by demonstrating a stabilizing influence on each of eight different types of nucleotide mismatches. An HCV probe and synthetic templates are used in the experimental system, and single nucleotide mismatch stabilization is demonstrated by measuring the Tm of the various hybridization complexes that are formed.

Melting curve reactions were established using the single-labeled FAM probe shown in FIG. 52A and synthetic templates that were engineered to contain various single base mismatches when hybridized with this probe. Note that these engineered templates do not correlate with any particular HCV genotypes, and were constructed for illustrative purposes only. These engineered templates are shown below. The nucleotide position that is mismatched when annealed to the probe is shown in lowercase. One of the templates was designed with no mismatches.

| Synthetic Template | SEQ ID NO: |
|---|---|
| CCGGTCGTCCTGGCAATTCCG | 26 |
| CCGGTCGTCCcGGCAATTCCG | 27 |
| CCGGTCGTCCgGGCAATTCCG | 28 |
| CCGGTCGTCCaGGCAATTCCG | 29 |
| CCGGTCGTCCTGGCcATTCCG | 30 |
| CCGGTCGTCCTGGCgATTCCG | 31 |
| CCGGTCGTCCTGGCtATTCCG | 32 |
| CCGGTCGTCCTcGCAATTCCG | 33 |
| CCGGTCGTCgTGGCAATTCCG | 34 |

These combinations of probe and template produced the single nucleotide mismatches shown in the FIG. 61. One hybridization template was included that produced no mismatches with the probe (i.e., an A:T perfect match). Each melting analysis reaction contained alternatively 10 µg/mL methylene blue or 40 µg/mL methylene blue.

This Tm melting data is summarized in the bar graph in FIG. 61. A representative set of data is shown. Also indicated on the graph is the predicted Tm of the respective hybridization complexes (in the absence of methylene blue). These calculated values were derived from Visual OMP software estimates (DNA Software, Inc., Ann Arbor, Mich.).

As can be seen in the figure, the addition of methylene blue to the melting reactions significantly stabilized the mismatched duplexes, as determined by their respective Tm values compared to the predicted Tm values in the absence of methylene blue. Furthermore, the addition of 40 µg/mL methylene blue appeared to be more effective than 10 µg/1 mL methylene blue at stabilizing the duplexes. These methylene blue stabilizing effects also were also observed in the perfect match duplex. These data demonstrate that the duplex stabilization effect is not limited to any particular mismatch types, and is a general phenomenon. In some cases, the degree of stabilization is dependent on the mismatch type.

Example 23

Demonstration of Improved Subtype Detection in the Presence of Thiazine Dyes Using an HIV Model System The present example illustrates the benefits of the duplex stabilization properties of thiazine dyes in the amplification and detection of viral targets. Because of the ability of the thiazine dyes to stabilize mismatched duplexes, it is shown herein that the detection sensitivity of polymorphic subtypes can be greatly improved due to improved amplification and/or detection efficiencies. In contrast to the previous example, this example used $C_T$ values of various TaqMan amplification reactions to demonstrate the benefits of enhanced duplex stability. HIV amplification primers, an HIV double-labeled 5'-nuclease quantitation probe and HIV synthetic templates were used in the experimental model system, as provided in FIG. 62. Beneath the primer and probe sequences in FIG. 62, the corresponding homologous domains from known HIV isolates are provided, with the variable positions indicated.

Single tube RT-PCR amplification reactions for the real-time quantitation of amplicon products were established using the amplification primers as shown below:

| Amplification primer | Sequence | SEQ ID NO |
|---|---|---|
| SK145BU | AGTGGGGGGACATCAAGCAGCCATGCAA-tBuBndA | 23 |
| GAG152BU | GGTACTAGTAGTTCCTGCTATGTCACTTC-tBuBndA | 24 | where tBuBndA = N6-t-butylbenzyl-dA

The amplification reactions also included the double-labeled 5'-nuclease quantitation probe GAG108FBHQ29I having the sequence:

(SEQ ID NO: 25)
FAM-TCTGCAGCTBHQ2TCCTCATTGATGGTATCTTTTA-PO$_4$ where FAM is the fluorescent label, PO$_4$ is a terminal phosphate and BHQ2 is the black hole quencher (BHQ™)-2. The amplification reactions also included synthetically produced HIV RNA molecules produced by in vitro transcription of subcloned isolated HIV genetic material and purified by oligo-dT-sepharose chromatography. One million copies of the specified RNA transcript were used in each reaction. The PCR reaction used the following cycling program:

50° C./5 min; 59° C./30 min; 95° C./2 min; 95° C.→58° C. (2 cycles); 91° C.→58° C. (60 cycles)

In a first experiment, an HIV RNA amplification (RT-PCR) quantitation using the SK145BU and GAG152BU amplification primers and the GAG108FBHQ29I 5'-nuclease quantitation probe was established. The experimental results are provided in FIG. 63. Various HIV RNA templates (10$^6$ copies each) were used in separate amplification reactions, as indicated. The numbers of nucleotide mismatches in the forward primer, reverse primer and the 5'-nuclease probe are shown for each HIV subtype tested in the table below. No thiazine dye is present in the reactions. A representative set of data is shown. Also indicated are the $C_T$ numbers obtained for each HIV subtype. As seen in FIG. 63 and the table, each HIV genotype tested has a distinct $C_T$ number.

The HIV RNA amplification quantitation analysis provided in FIG. 63 was repeated in the experiment shown in FIG. 64, with the exception that the reactions were supplemented with 50 µg/mL of new methylene blue. As can be seen, the addition of the new methylene blue resulted in improved levels of detection, where the $C_T$ values are lowered with the addition of the thiazine dye. These results are summarized below:

| HIV Genotype | No. of duplex mismatches in: for primer/rev primer/ nuclease probe | $C_T$ value without new methylene blue | $C_T$ value with 50 µg/mL new methylene blue |
|---|---|---|---|
| 101-15 | 0/0/3 | ND | ND |
| 105-1 | 0/0/1 | 24.8 | 24.2 |
| 106-1 | 2/1/2 | 27.7 | 25.2 |
| 108-3 | 1/1/3 | 28.3 | 27.2 |
| 109-1 | 2/2/2 | 28.2 | 27.1 |
| 110-5 | 6/0/1 | 33.0 | 23.9 |

As shown in FIGS. 63 and 64, and summarized in table above, the duplex stabilization properties of thiazine dyes are demonstrated in this model system, likely through stabilizing both the primer-template duplex as well as the amplicon-nuclease probe duplex. This stabilization leads to better detection sensitivity for polymorphic subtypes.

Example 24

Demonstration of Dose-Dependent Nucleic Acid Duplex Stabilization in the Presence of Varying Concentrations of Thiazine Dyes Using an HIV Model System The present example illustrates the duplex stabilization properties of thiazine dyes, where the dye is employed at a range of concentrations. This example uses the same HIV experimental model system and reagents as described in Example 23.

Amplification reactions for the real-time quantitation of HIV amplification products were established using the HIV amplification primers SK145BU (SEQ ID NO: 23) and GAG152BU (SEQ ID NO: 24) and the 5'-nuclease quantitation probe GAG108FBHQ29I (SEQ ID NO: 25). The amplification reactions in this Example targeted the HIV genotype 110-5 synthetic RNA template (10$^6$ copies). This particular combination of HIV genotype, amplification primers and nuclease probe results in six mismatches under the forward primer and one mismatch under the 5'-nuclease quantitation probe.

The amplification and quantitation reactions were alternatively supplemented with various concentrations of new methylene blue from 10-50 µg/mL. One reaction without any new methylene blue was also run. Results are displayed as amplicon growth curves and $C_T$ values. The results are provided in FIG. 65. A representative set of data is shown. As clearly seen in the figure, the addition of new methylene blue results in increased sensitivity of the amplification and quantitation assay, as evidenced by the decreased $C_T$ values with increasing thiazine dye concentration. This is likely through stabilizing both the primer-template duplex as well as the amplicon-nuclease probe duplex. This data clearly shows the beneficial effect of new methylene blue on the detection sensitivity of this HCV subtype as a function of increasing concentration of the dye.

Example 25

Demonstration of Nucleic Acid Duplex Stabilization by Thiazine Dyes Using SYBR® Green Amplicon Detection The present example illustrates the duplex stabilization properties of thiazine dyes, where the model system uses SYBR® Green to monitor amplicon accumulation. Amplification reactions for the real-time quantitation of HIV amplification products were established using the HIV amplification primers SK145BU (SEQ ID NO: 23) and GAG152BU (SEQ ID NO: 24). The amplification reactions in this Example targeted the HIV genotype 110-5 synthetic RNA template ($10^6$ copies). All the reactions were supplemented with SYBR® Green to monitor accumulation of the double-stranded amplicon product. A 5'-nuclease quantitation probe was not used.

The amplification reactions were alternatively supplemented with either 30 μg/mL or 50 μg/1 mL new methylene blue. A reaction was also run in the absence of new methylene blue. When no new methylene blue was used in the reaction, a 1:10,000 dilution (1× concentration) of SYBR® Green was used. When the 30 and 50 μg/mL new methylene blue were used, a dilution of 1:2,500 of SYBR® Green was (4× concentration). SYBR® Green fluorescence was measured at the same wavelength as the FAM label. The addition of new methylene blue to the reactions had the effect of reducing the fluorescence of the SYBR® Green emission. To compensate for this, the reactions containing new methylene blue used the higher concentration of SYBR® Green. The increased concentration of SYBR® Green is known to have a negative influence on the amplification efficiency. However, in spite of this detrimental effect, the beneficial effect of the new methylene blue on duplex stabilization is clearly seen.

The results of this assay are shown in FIG. 66. Results are displayed as amplicon growth curves and $C_T$ values. A representative set of data is shown. As clearly seen in the figure, the addition of new methylene blue results in improved sensitivity of the amplification and quantitation assay, as evidenced by the decreased $C_T$ values with increasing thiazine dye concentration. Presumably, the thiazine dye is stabilizing the interaction of the amplification primers with the HIV target template. Furthermore, this Example illustrates that a SYBR® Green detection system can be used in conjunction with a thiazine dye for the stabilization of DNA duplexes.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All scientific publications, patent publications of any type, issued patents, pending patent applications, and/or other documents cited in this application are incorporated by reference in their entirety for all purposes to the same extent as if each individual publication, patent, patent application, and/or other document were individually indicated to be incorporated by reference for all purposes.

---

What is claimed is:

1. A method for producing a stabilized nucleic acid duplex, the method comprising:
   (a) providing (i) a sample containing or suspected of containing a target nucleic acid molecule; (ii) an oligonucleotide complementary or partially complementary to said target nucleic acid molecule; and (iii) at least one soluble thiazine dye present at a concentration effective to stabilize a duplex formed between said target nucleic acid molecule and said oligonucleotide, wherein said target nucleic acid, said oligonucleotide and said thiazine dye are all in solution in free form; and
   (b) either (i) annealing said target nucleic acid and said oligonucleotide in the presence of said thiazine dye; or (ii) annealing said target nucleic acid and said oligonucleotide, followed by admixing with said thiazine dye; under conditions wherein base-pairing occurs to produce at least one stabilized nucleic acid duplex.

2. The method of claim 1, wherein stability of said nucleic acid duplex of (b) is improved compared to stability of a nucleic acid duplex comprising said target nucleic acid and said oligonucleotide in the absence of said thiazine dye.

3. The method of claim 1, further comprising: (c) detecting said stabilized nucleic acid duplex under conditions that provide improved stability.

4. The method of claim 1, wherein said stabilized nucleic acid duplex comprises one or more nucleobase mismatches.

5. The method of claim 1, wherein said providing said target nucleic acid molecule and said oligonucleotide comprises providing one nucleic acid molecule, wherein said nucleic acid molecule is a molecular beacon.

6. The method of claim 1, wherein said oligonucleotide is effective to prime a nucleic acid extension reaction when annealed to said target nucleic acid.

7. The method of claim 1, wherein step (a) further comprises providing a second oligonucleotide complementary or partially complementary to said target nucleic acid molecule, each of said oligonucleotides being effective to prime a nucleic acid extension reaction when annealed to said target nucleic acid.

8. The method of claim 1, wherein step (a) further comprises providing a labeled oligonucleotide complementary or partially complementary to said target nucleic acid molecule.

9. The method of claim 1, wherein said target nucleic acid molecule is an amplicon.

10. The method of claim 1, wherein said oligonucleotide comprises one or more naturally-occurring nucleotides, modified nucleotides, nucleotide analogs, one or more unnatural bases, unnatural internucleotide linkages, unnatural nucleotide backbones, or any combination thereof.

11. The method of claim 1, wherein said thiazine dye is selected from methylene blue, methylene green, thionin, sym-dimethylthionin, toluidine blue O, new methylene blue, methylene violet bernthsen, azure A, azure B, azure C and 1,9-dimethylmethylene blue.

12. The method of claim 1, wherein said at least one thiazine dye is present at a concentration of at least 10 µg/mL.

13. The method of claim 1, wherein said annealing comprises annealing in the presence of a thiazine dye at a concentration between about 10 µg/mL and 50 µg/mL.

14. The method of claim 1, wherein said annealing comprises annealing in the presence of a thiazine dye at a concentration of about 40 µg/mL.

* * * * *